US009718876B2

(12) United States Patent
Beaumont et al.

(10) Patent No.: US 9,718,876 B2
(45) Date of Patent: Aug. 1, 2017

(54) RSV G PROTEIN SPECIFIC ANTIBODIES

(71) Applicant: AIMM Therapeutics B.V., Amsterdam Zuidoost (NL)

(72) Inventors: Tim Beaumont, Ouderkerk a/d Amstel (NL); Etsuko Yasuda, Amsterdam (NL)

(73) Assignee: AIMM THERAPEUTICS B.V., Amsterdam Zuidoost (NL)

( * ) Notice: Subject to any disclaimer, the term of this patent is extended or adjusted under 35 U.S.C. 154(b) by 11 days.

(21) Appl. No.: 14/359,291

(22) PCT Filed: Nov. 16, 2012

(86) PCT No.: PCT/NL2012/050812
§ 371 (c)(1),
(2) Date: May 19, 2014

(87) PCT Pub. No.: WO2013/095091
PCT Pub. Date: Jun. 27, 2013

(65) Prior Publication Data

US 2015/0004155 A1 Jan. 1, 2015

(30) Foreign Application Priority Data

Nov. 17, 2011 (EP) .................................... 11189613

(51) Int. Cl.

| | |
|---|---|
| *C07K 16/10* | (2006.01) |
| *G01N 33/569* | (2006.01) |
| *A61K 39/00* | (2006.01) |

(52) U.S. Cl.
CPC ... *C07K 16/1027* (2013.01); *G01N 33/56983* (2013.01); *A61K 2039/505* (2013.01); *A61K 2039/507* (2013.01); *C07K 2317/21* (2013.01); *C07K 2317/30* (2013.01); *C07K 2317/34* (2013.01); *C07K 2317/76* (2013.01); *G01N 2333/135* (2013.01)

(58) Field of Classification Search
None
See application file for complete search history.

(56) References Cited

U.S. PATENT DOCUMENTS

| | | | |
|---|---|---|---|
| 2008/0226630 | A1 | 9/2008 | Lantto et al. |
| 2010/0285022 | A1 | 11/2010 | Kauvar et al. |
| 2011/0189171 | A1 | 8/2011 | Lantto et al. |

FOREIGN PATENT DOCUMENTS

| | | | |
|---|---|---|---|
| WO | 2008106980 | A2 | 9/2008 |
| WO | 2008106980 | A3 | 9/2008 |
| WO | 2008147196 | A2 | 12/2008 |
| WO | 2008147196 | A3 | 2/2009 |
| WO | 2009055711 | A2 | 4/2009 |
| WO | 2009055711 | A3 | 9/2009 |
| WO | 2010087994 | A2 | 8/2010 |
| WO | 2010087994 | A3 | 2/2011 |
| WO | 2011043643 | A1 | 4/2011 |
| WO | 2013095091 | A2 | 6/2013 |

OTHER PUBLICATIONS

Rudikoff et al. Proc Natl Acad Sci USA 1982 vol. 79 p. 1979-1983.*
PCT International Search Report, PCT/NL2012/050812, dated Jul. 11, 2013.
Haynes et al., Therapeutic monoclonal antibody treatment targeting respiratory syncytial virus (RSV) G protein mediates viral clearance and reduces the pathogenesis of RSV infection in BALB/c mice, The Journal of Infectious Diseases, Aug. 1, 2009, pp. 439-447, vol. 200, No. 3.
Martinez et al., Antigenic structure of the human respiratory syncytial virus G glycoprotein and relevance of hypermutation events for the generation of antigenic variants, Journal of General Virology, 1997, pp. 2419-2429, vol. 78, No. 10.

* cited by examiner

*Primary Examiner* — Shanon A Foley
*Assistant Examiner* — Myron Hill
(74) *Attorney, Agent, or Firm* — Gianna Julian-Arnold; Saul Ewing LLP

(57) ABSTRACT

The disclosure relates to human isolated, synthetic or recombinant antibodies or functional parts thereof, specific for the RSV G protein. Antibodies specific for the RSV G protein are particularly suitable for counteracting RSV and symptoms, such as inflammation, resulting from an RSV infection. The disclosure further relates to the use of such RSV G-specific antibodies for diagnosis of an RSV infection and as a medicament and/or prophylactic agent for, at least in part, treating or alleviating symptoms of a Respiratory Syncytial Virus infection and/or a Respiratory Syncytial Virus related disorder.

1 Claim, 11 Drawing Sheets

FIG. 1 screening on RSV native proteins

● RSV A2 infected HEp-2 cell (express F and G protein)

● RSV G protein expressing VERO cell

Select B cell culture that binds both cell lines

RSV infected HEp-2 cells expressing RSV G and F (cells are stained green)
VERO cells expressing the RSV G protein

*FIG. 2*

RSV A2 neutralization w/ B cell derived RSV G protein specific antibodies + 10% rabbit serum complement

RSV Ga sequence

| aa residue | 161 | N | D | F | H | F | E | V | F | N | F | V | P | C | S | I | 175 |
|---|---|---|---|---|---|---|---|---|---|---|---|---|---|---|---|---|---|
| 131-2G | | | | | | | | | | | | | | | | | |
| 3D3 | | | | | | | | | | | | | | | | | |
| AT40 | | | | | | | | | | | | | | | | | |
| AT44 | | | | | | | | | | | | | | | | | |

| aa residue | 186 | C | K | R | I | P | N | K | K | P | G | K | K | T | 198 |
|---|---|---|---|---|---|---|---|---|---|---|---|---|---|---|---|
| AT32 | | | | | | | | | | | | | | | |

*FIG. 7C*

RSV G PROTEIN SPECIFIC ANTIBODIES

CROSS-REFERENCE TO RELATED APPLICATIONS

This application is a national phase entry under 35 U.S.C. §371 of International Patent Application PCT/NL2012/050812, filed Nov. 16, 2012, designating the United States of America and published in English as International Patent Publication WO2013/095091 A2 on Jun. 27, 2013, which claims the benefit under Article 8 of the Patent Cooperation Treaty to European Patent Office Application Serial No. 11189613.0, filed Nov. 17, 2011, the disclosure of each of which is hereby incorporated herein in its entirety by this reference.

STATEMENT ACCORDING TO 37 C.F.R. §1.821(c) or (e)—SEQUENCE LISTING SUBMITTED AS A TXT AND PDF FILES

Pursuant to 37 C.F.R. §1.821(c) or (e), files containing a TXT version and a PDF version of the Sequence Listing have been submitted concomitant with this application, the contents of which are hereby incorporated by reference.

TECHNICAL FIELD

The disclosure relates to the fields of biology, immunology and medicine.

BACKGROUND

Respiratory Syncytial Virus (RSV) is a common cold virus belonging to the family of paramyxovirus. RSV is virulent, easily transmissible and the most common cause of lower respiratory tract disease in children of less than 2 years of age. Up to 98% of children attending day care will be infected in a single RSV season. Between 0.5% and 3.2% of children with RSV infection require hospitalization. Approximately 90,000 hospital admissions and 4500 deaths per year were reported in United States. Major risk factors for hospitalization due to RSV are premature birth, chronic lung disease, congenital heart disease, compromised immunity, and age younger than 6 weeks in otherwise healthy children.

Two subtypes of RSV have been identified, subtype A and subtype B. RSV has two major surface glycoproteins, the fusion protein (F protein) and the attachment protein (G protein). The F protein of RSV is a viral membrane protein and responsible for fusion of the virion with a host cell after attachment. In addition, infection of neighboring cells through the formation of syncytia is promoted by the F protein and its function is thought to depend on the original oligomeric structure of the protein. The G protein is a 89 kD protein, which is also known as the attachment protein. The G protein differs considerably between the two RSV subtypes, whereas the F protein is more conserved. Approximately 53% homology is present within a G protein from subtypes A and B. Although G protein is not required for infection of host cells, anti-RSV G antibodies have shown to improve symptoms in animal models and can induce virus neutralization in the presence of complement.

Antibodies against the F or G protein of RSV have been described. Palivizumab is a genetically engineered, humanized monoclonal antibody against the F protein. WO 2008/147196 discloses sequences of human RSV F protein binding molecules. A mouse monoclonal antibody (131-2G) against the G protein has been described, which is thought to bind to a CX3C (fractalkine) motif in the RSV G protein, which motif is capable of binding to the CX3CR1 (Fractalkine) receptor on NK cells, T cells and monocytes. This antibody was demonstrated to reduce migration of PBMCs towards RSV G glycoprotein (Tripp et al., 2001, Nat. Immunol. 2001, 2(8):732-8). Antibody 131-2G does not neutralize RSV in vitro, however, in an in vivo mouse model dosing at 300 mg/mouse resulted in reduced RSV A2 recovery from lungs, reduced pulmonary inflammation, and lowered IFN-gamma levels in a mouse model. Human monoclonal antibodies against RSV G protein have been described in U.S. 2010-0285022, WO 2009/055711 and Collarini et al. (Journal of Immunology, 2009, 183: 6338-6345). The antibodies bind to a conserved epitope in the G protein close to the CX3C domain, which is located in a region of the G protein corresponding to amino acid positions 164-172.

No effective treatment of RSV positive bronchiolitis beside supportive care in the form of adequate nutrition and oxygen therapy is currently available. Antiviral therapies such as Ribavirin have not been proven to be effective in RSV infection. Only monoclonal antibody palivizumab (also called Synagis), is registered for prophylaxis against RSV infection. However, palivizumab is not always effective. It is only useful and approved for prophylactic treatment of premature infants up to 4 KG body weight. Thus, palivizumab cannot be used to treat an established RSV infection. Furthermore, palivizumab is only partly effective as it reduces hospitalization of infants by approximately 50%.

Therefore, there is a need for additional antibodies and therapies against RSV.

BRIEF SUMMARY

It is an object of the present disclosure to provide additional antibodies against the G protein of RSV, or functional equivalents of such antibodies and compositions comprising antibodies. Preferably, antibodies are provided which recognize a different epitope as compared to known RSV antibodies. It is a further object to provide antibodies against the G protein of RSV, which are able to potentiate neutralizing activity of an antibody capable of binding an F protein of RSV.

The disclosure, therefore, provides a human isolated, synthetic or recombinant antibody or functional part thereof, or immunoglobulin chain or functional equivalent thereof, capable of binding an epitope of a G protein of Respiratory Syncytial Virus, which epitope is located between amino acids 51-160 and/or between amino acids 187-299 of the G protein, wherein the numbering of amino acids is based on the RSV G protein of subtype A2 and B1 as depicted in FIG. 1.

A "functional part of an antibody" is defined as a part which has at least one shared property as the antibody in kind, not necessarily in amount. The functional part is capable of binding the same antigen or epitope as the antibody, albeit not necessarily to the same extent. A functional part of an antibody preferably comprises a single domain antibody, a single chain antibody, a nanobody, an unibody, a single chain variable fragment (scFv), a Fab fragment or a F(ab')2 fragment.

A functional part of an antibody is also produced by altering an antibody such that at least one property, preferably an antigen-binding property, of the resulting compound is essentially the same in kind, not necessarily in amount.

This is done in many ways, for instance, through conservative amino acid substitution, whereby an amino acid residue is substituted by another residue with generally similar properties (size, hydrophobicity, etc.), such that the overall functioning is likely not to be seriously affected.

A "functional equivalent of an immunoglobulin chain" is defined herein as an artificial binding compound, comprising at least one CDR sequence of an immunoglobulin chain.

The term "a human isolated, synthetic or recombinant antibody or functional part thereof, or immunoglobulin chain or functional equivalent thereof" includes isolated human antibodies or functional parts or immunoglobulins or functional equivalents thereof, as well as synthetic or recombinant antibodies or functional parts or immunoglobulins or functional equivalents thereof, the sequence of which is derived from the sequence of human antibodies.

Isolated, synthetic or recombinant antibodies or functional parts thereof, or immunoglobulin chains or functional equivalents thereof, capable of binding to a G protein of Respiratory Syncytial Virus, described herein, are also referred to as "RSV G-specific antibodies, according to the disclosure."

An RSV G-specific antibody, according to the disclosure, is preferably a human antibody. The use of human antibodies for prophylaxis and therapy in humans diminishes the chance of side-effects due to an immunological reaction in a human individual against non-human sequences. In another embodiment, an RSV G-specific antibody, according to the disclosure, is a humanized antibody. Humanized antibodies are made by incorporating non-human hypervariable domains into human antibodies and, therefore, immunogenic properties are diminished as compared to fully non-human antibodies. In another embodiment, an RSV G-specific antibody, according to the disclosure, is a chimeric antibody. In a chimeric antibody, sequences of interest, such as, for instance, a binding site of interest, are included into an RSV G-specific antibody, according to the disclosure. FIG. 1 shows the amino acid sequence of RSV G protein of subtypes A2 and B1. If a part of RSV G protein is indicated herein by the amino acid residues of which the part consists, the numbering is based on the numbering shown in FIG. 1 and includes corresponding amino acid residues in G proteins of other RSV strains.

In one embodiment, RSV G-specific antibodies, according to the disclosure, are capable of binding an epitope of a G protein of RSV, which epitope is located between amino acids 51-160 and/or between amino acids 187-299 of the G protein. This provides the advantage that they bind to a different epitope as compared to previously disclosed RSV G antibodies. For instance, RSV G antibodies disclosed in U.S. 2010-0285022 bind to multiple but different epitopes of the G protein of RSV, which epitopes are located between amino acids 160-176 of the G protein. The CX3C motif is located between amino acids 182-186, as is shown in FIG. 1. Thus, several preferred RSV G-specific antibodies, according to the disclosure, bind a different epitope of the G protein than the epitope of antibodies disclosed in U.S. 2010-0285022 and the CX3C motif. RSV G-specific antibodies, according to the disclosure, that bind to a different epitope as compared to known RSV G antibodies are thus advantageously combined with such known antibodies in order to improve the treatment with antibodies. Such RSV G-specific antibodies, according to the disclosure, and such known antibodies do not compete for the same epitope in the G protein.

An RSV G-specific antibody, according to the disclosure, capable of binding an epitope of a G protein of RSV, which epitope is located between amino acids 51-160 and/or between amino acids 187-299 of the G protein is particularly suitable for combination with one or more known RSV G binding antibodies. Such preferred RSV G-specific antibodies, according to the disclosure, are also particularly suitable for combination with one or more other RSV G-specific antibodies, according to the disclosure, that are capable of binding other epitopes of RSV G protein, such as, for instance, a conformational epitope or an epitope, which comprises the CX3C motif of the RSV G protein.

RSV G-specific antibodies, according to the disclosure, which are capable of binding an epitope of a G protein of RSV, which epitope is located between amino acids 51-160 and/or between amino acids 187-299 of the G protein, and thus are particularly preferred, are the antibodies designated AT35, AT37, AT39, AT43, AT51, AT47, AT32, AT33, AT36 and AT50, which have heavy chain sequences of SEQ ID NOS:133, 115, 116, 119, 125, 122, 110, 111, 114 and 124 as depicted in table 1, respectively, and light chain sequences of SEQ ID NOS:131, 133, 134, 137, 143, 140, 128, 129, 132 and 142 as depicted in table 1, respectively. The heavy and light chain CDR sequences of these preferred antibodies are also depicted in table 1, namely SEQ ID NOS:2, 3, 5, 6, 7, 8, 11, 14, 16 and 17 being the heavy chain CDR1 sequences of these antibodies, SEQ ID NOS:20, 21, 23, 24, 25, 26, 29, 32, 34 and 35 being the heavy chain CDR2 sequences of these antibodies, SEQ ID NOS:38, 39, 41, 42, 43, 44, 47, 50, 52 and 53 being the heavy chain CDR3 sequences of these antibodies, SEQ ID NOS:56, 57, 59, 60, 61, 62, 65, 68, 70 and 71 being the light chain CDR1 sequences of these antibodies, SEQ ID NOS:74, 75, 77, 78, 79, 80, 83, 86, 88 and 89 being the light chain CDR2 sequences of these antibodies, and SEQ ID NOS:92, 93, 95, 96, 97, 98, 101, 104, 106 and 107 being the light chain CDR3 sequences of these antibodies.

The disclosure thus provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO:2, 3, 5, 6, 7, 8, 11, 14, 16 and 17, and/or a heavy chain CDR2 sequence comprising a sequence which is at least 70% identical to a sequence selected from the group consisting of SEQ ID NO: 20, 21, 23, 24, 25, 26, 29, 32, 34 and 35, and/or a heavy chain CDR3 sequence comprising a sequence which is at least 70% identical to a sequence selected from the group consisting of SEQ ID NO: 38, 39, 41, 42, 43, 44, 47, 50, 52 and 53, and/or a light chain CDR1 sequence comprising a sequence which is at least 70% identical to a sequence selected from the group consisting of SEQ ID NO: 56, 57, 59, 60, 61, 62, 65, 68, 70 and 71, and/or a light chain CDR2 sequence comprising a sequence which is at least 70% identical to a sequence selected from the group consisting of SEQ ID NO: 74, 75, 77, 78, 79, 80, 83, 86, 88 and 89, and/or a light chain CDR3 sequence comprising a sequence which is at least 70% identical to a sequence selected from the group consisting of SEQ ID NO: 92, 93, 95, 96, 97, 98, 101, 104, 106 and 107. Preferably, the antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

Of course, the six CDR sequences of one given antibody of interest (or sequences at least 70% identical thereto) are typically combined. An antibody, functional part, immunoglobulin or functional equivalent, according to the disclosure, thus preferably comprises CDR sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to the heavy chain CDR1, CDR2 and CDR3 sequences and the light chain CDR1, CDR2 and CDR3 sequences of the same antibody provided by the disclosure (as depicted in table 1).

The terms "AT35," "AT37," "AT39," "AT43," "AT51," "AT47," "AT32," "AT33," "AT36," and "AT50, as used herein, encompass all antibodies and functional equivalents with the indicated heavy chain and light chain sequences, for instance, isolated and/or purified or recombinantly produced. The indicated particularly preferred antibodies do not compete with antibody 3D3 described in US 2010-0285022 or monoclonal antibody 131-2G, which binds to the CX3C motif in the G protein, which is located at amino acid positions 173-186 of the G protein. Thus, the indicated preferred antibodies are advantageously combined with these known antibodies.

In another embodiment, the disclosure provides a human isolated, synthetic or recombinant antibody or functional part thereof, or immunoglobulin chain or functional equivalent thereof, capable of binding to a G protein of Respiratory Syncytial Virus (RSV), which antibody or functional part, or immunoglobulin chain or functional equivalent is capable of potentiating RSV neutralizing activity of an antibody capable of binding an F protein of RSV.

"An antibody capable of binding an F protein of RSV" is herein also called an RSV F-specific antibody. With the term "potentiating RSV neutralizing activity of an antibody capable of binding an F protein of RSV" is meant that the RSV neutralizing activity of the antibody capable of binding an F protein of RSV is increased if an RSV G-specific antibody, according to the disclosure, is also present. An RSV G-specific antibody, according to the disclosure, is itself not capable of neutralizing RSV in the absence of complement factors. However, it was surprisingly found that the neutralizing activity of a RSV F-specific antibody is nevertheless increased if such RSV G-specific antibody, according to the disclosure, is present. The neutralizing activity can be neutralizing activity in vitro or in vivo. An antibody capable of binding a F protein of RSV of which RSV neutralizing activity is potentiated by an RSV G-specific antibody, according to the disclosure, is preferably palivizumab, AM14, AM16, AM23 or D25, which are described in WO 2008/147196, or AM22, described in WO 2011/043643 and of which the heavy and light chain and CDR sequences are depicted in table 1.

Preferred RSV G-specific antibodies capable of potentiating RSV neutralizing activity of an RSV F-specific antibody are AT46, AT32, AT33 and AT35, which have heavy chain sequences of SEQ ID NOS:109, 110, 111 and 113 as depicted in table 1, respectively, and light chain sequences of SEQ ID NOS:127, 128, 129 and 131 as depicted in table 1, respectively. The heavy and light chain CDR sequences of these preferred antibodies are also depicted in table 1, namely SEQ ID NOS:1, 2, 3 and 5, being the heavy chain CDR1 sequences of these antibodies, SEQ ID NOS:19, 20, 21 and 23 being the heavy chain CDR2 sequences of these antibodies, SEQ ID NOS:37, 38, 39 and 41 being the heavy chain CDR3 sequences of these antibodies, SEQ ID NOS: 55, 56, 57 and 59 being the light chain CDR1 sequences of these antibodies, SEQ ID NOS:73, 74, 75 and 77 being the light chain CDR2 sequences of these antibodies, and SEQ ID NOS:91, 92, 93 and 95 being the light chain CDR3 sequences of these antibodies.

The disclosure thus provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO:1, 2, 3 and 5, and/or a heavy chain CDR2 sequence comprising a sequence which is at least 70% identical to a sequence selected from the group consisting of SEQ ID NO:19, 20, 21 and 23, and/or a heavy chain CDR3 sequence comprising a sequence which is at least 70% identical to a sequence selected from the group consisting of SEQ ID NO:37, 38, 39 and 41, and/or a light chain CDR1 sequence comprising a sequence which is at least 70% identical to a sequence selected from the group consisting of SEQ ID NO:55, 56, 57 and 59, and/or a light chain CDR2 sequence comprising a sequence which is at least 70% identical to a sequence selected from the group consisting of SEQ ID NO:73, 74, 75 and 77, and/or a light chain CDR3 sequence comprising a sequence which is at least 70% identical to a sequence selected from the group consisting of SEQ ID NO:91, 92, 93 and 95. Preferably, the antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100% identical to these sequences.

As described before, the six CDR sequences of one given antibody of interest (or sequences at least 70% identical thereto) are typically combined. Since AT46, AT32, AT33 and AT35 are preferred examples of antibodies capable of potentiating the RSV neutralizing activities of antibodies capable of binding an F protein of RSV, the disclosure thus provides a human isolated, synthetic or recombinant antibody or functional part thereof, or immunoglobulin or functional equivalent thereof, capable of binding to a G protein of Respiratory Syncytial Virus (RSV), which antibody or functional part or immunoglobulin or functional equivalent is capable of potentiating RSV neutralizing activity of an antibody capable of binding an F protein of RSV, the antibody or functional part or immunoglobulin or functional equivalent having a combination of CDR sequences selected from the group consisting of:

SEQ ID NO: 1 (heavy chain CDR1 of AT46) and SEQ ID NO: 19 (heavy chain CDR2 of AT46) and SEQ ID NO: 37 (heavy chain CDR3 of AT46) and SEQ ID NO: 55 (light chain CDR1 of AT46) and SEQ ID NO: 73 (light chain CDR2 of AT46) and SEQ ID NO: 91 (light chain CDR3 of AT46); and SEQ ID NO: 2 (heavy chain CDR1 of AT32) and SEQ ID NO: 20 (heavy chain CDR2 of AT32) and SEQ ID NO: 38 (heavy chain CDR3 of AT32) and SEQ ID NO: 56 (light chain CDR1 of AT32) and SEQ ID NO: 74 (light chain CDR2 of AT32) and SEQ ID NO: 92 (light chain CDR3 of AT32); and SEQ ID NO:3 (heavy chain CDR1 of AT33) and SEQ ID NO: 21 (heavy chain CDR2 of AT33) and SEQ ID NO: 39 (heavy chain CDR3 of AT33) and SEQ ID NO: 57 (light chain CDR1 of AT33) and SEQ ID NO: 75 (light chain CDR2 of AT33) and SEQ ID NO: 93 (light chain CDR3 of AT33); and SEQ ID NO: 5 (heavy chain CDR1 of AT35) and SEQ ID NO: 23 (heavy chain CDR2 of AT35) and SEQ ID NO: 41 (heavy chain CDR3 of AT35) and SEQ ID NO: 59 (light chain CDR1 of AT35) and SEQ ID NO: 77 (light chain CDR2 of AT35) and SEQ ID NO: 95 (light chain CDR3 of AT35); and CDR sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical to the sequences of any of these combinations.

In another preferred embodiment, the heavy and light sequences of one given antibody of interest (or sequences at least 70% identical thereto) are combined. Also provided is, therefore, a human isolated, synthetic or recombinant antibody or functional part thereof, or immunoglobulin or functional equivalent thereof, capable of binding to a G protein of Respiratory Syncytial Virus (RSV), which antibody or functional part or immunoglobulin or functional equivalent is capable of potentiating RSV neutralizing activity of an antibody capable of binding an F protein of RSV, the antibody or functional part or immunoglobulin or functional equivalent having a combination of a heavy and light chain sequence selected from the group consisting of:

SEQ ID NO: 109 (heavy chain of AT46) and SEQ ID NO: 127 (light chain of AT46); and SEQ ID NO: 110 (heavy chain of AT32) and SEQ ID NO: 128 (light chain of AT32); and SEQ ID NO: 111 (heavy chain of AT33) and SEQ ID NO: 129 (light chain of AT33); and SEQ ID NO: 113 (heavy chain of AT35) and SEQ ID NO: 131 (light chain of AT35); and heavy and light chain sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical to the sequences of any of these combinations.

The terms "AT46," "AT32," "AT33," and "AT35," as used herein, encompass all antibodies and functional equivalents with the indicated heavy chain and light chain sequences, for instance, isolated and/or purified or recombinantly produced.

An advantage of a combination of an RSV F-specific antibody and an antibody, according to the disclosure, that is capable of potentiating RSV neutralizing activity of the RSV F-specific antibody is that a lower dosis of the RSV F-specific antibody is needed in order to obtain the same neutralizing capacity. Therefore, less of the RSV F-specific antibody has to be administered to an individual for treatment and/or prevention of an RSV infection or RSV-related disorder. It is favorable to use an amount as low as possible to achieve a desired effect from both a health care of view, it is preferred to administer to a subject as less as possible of any substance, and from an economical point of view, a reduction of the amount of the therapeutic antibody needed generally reduces the cost of the treatment. Alternatively, with a similar amount of RSV F-specific antibody, a more effective treatment and/or prevention of an RSV infection and/or RSV-related disorder is achieved.

Furthermore, an RSV G-specific antibody, according to the disclosure, obviously recognizes a different epitope of RSV as an RSV F-specific antibody. By combining at least one RSV 6-specific antibody, according to the disclosure, with an RSV F-specific antibody, two or more different targets in RSV are recognized during the same therapy. This way, a more potent anti-RSV treatment is obtained. Such a combination will result in more effective treatment and/or prevention of an RSV infection and/or an RSV-related disorder.

Furthermore, in a preferred embodiment, a lower overall antibody dosage is needed, as compared to current treatment with palivizumab. As already mentioned above, a lower amount of antibody capable of binding an F protein of RSV is needed to obtain the same neutralizing capacity. However, an RSV G-specific antibody, according to the disclosure, itself is also capable of counteracting RSV. Thus, in order to obtain a desired activity in counteracting RSV a lower total amount of (RSV G-specific and RSV F-specific) antibodies is needed if an RSV G-specific antibody, according to the disclosure, is combined with an RSV F-specific antibody.

An RSV G-specific antibody, according to the disclosure, capable of potentiating RSV neutralizing activity of an RSV F-specific antibody is thus advantageously combined with such an RSV F-specific antibody. Provided is, thus, a pharmaceutical composition comprising an RSV G-specific antibody, according to the disclosure, and an antibody capable of binding an F protein of RSV, and a pharmaceutically acceptable carrier, diluent and/or excipient. Such a pharmaceutical composition is particularly suitable for use in the treatment and/or prevention of an RSV infection and/or an RSV-related disorder.

In the Examples, isolation of 17 antibodies, according to the disclosure, is described. The CDRs of these antibodies are depicted in table 1. The disclosure provides the insight that the CDRs with a sequence of SEQ ID NOS:1-17, SEQ ID NOS:19-35, SEQ ID NOS:37-53, SEQ ID NOS:55-71, SEQ ID NOS:73-89, and SEQ ID NOS:91-107 provide particularly desired RSV binding characteristics. The disclosure, therefore, provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO:1-17, and/or
a heavy chain CDR2 sequence comprising a sequence which is at least 70% identical to a sequence selected from the group consisting of SEQ ID NO:19-35, and/or
a heavy chain CDR3 sequence comprising a sequence which is at least 70% identical to a sequence selected from the group consisting of SEQ ID NO:37-53, and/or
a light chain CDR1 sequence comprising a sequence which is at least 70% identical to a sequence selected from the group consisting of SEQ ID NO:55-71, and/or
a light chain CDR2 sequence comprising a sequence which is at least 70% identical to a sequence selected from the group consisting of SEQ ID NO:73-89, and/or
a light chain CDR3 sequence comprising a sequence which is at least 70% identical to a sequence selected from the group consisting of SEQ ID NO:91-107.

Preferably, an RSV G-specific antibody, according to the disclosure, comprises a heavy and/or light chain CDR sequence which is at least 75%, more preferably at least 80%, more preferably at least 85%, more preferably at least 86%, more preferably at least 87%, more preferably at least 88%, more preferably at least 89%, more preferably at least 90% identical to a sequence selected from the group consisting of SEQ ID NO:1-17, SEQ ID NO:19-35, SEQ ID NO:37-53, SEQ ID NO: 55-71, SEQ ID NO:73-89, and SEQ ID NO:91-107. Most preferably, an RSV G-specific antibody, according to the disclosure, comprises a heavy and/or light chain CDR sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to a sequence selected from the group consisting of SEQ ID NO:1-17, SEQ ID NO:19-35, SEQ ID NO:37-53, SEQ ID NO: 55-71, SEQ ID NO:73-89, and SEQ ID NO:91-107. As described before, the six CDR sequences of one given antibody of interest (or sequences at least 70% identical thereto) are typically combined. An antibody, functional part, immunoglobulin or functional equivalent according to the disclosure thus preferably comprises CDR sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to the heavy chain CDR1, CDR2 and CDR3 sequences and the light chain CDR1, CDR2 and CDR3 sequences of antibody AT46, AT32, AT33, AT34, AT35, AT36, AT37, AT39, AT40, AT42, AT43, AT44, AT45, AT47, AT49, AT50 or AT51.

Particularly preferred RSV G-specific antibodies, according to the disclosure, are the antibodies AT46, AT32, AT33, AT34, AT35, AT36, AT37, AT39, AT40, AT42, AT43, AT44, AT45, AT47, AT49, AT50 and AT51, which have heavy chain and light chain CDR sequences as depicted in table 1, because these antibodies have been demonstrated to have particularly desired binding characteristics. In a preferred embodiment, an RSV G-specific antibody, according to the disclosure, therefore, comprises both the heavy and light chain CDR sequences of one of the above mentioned RSV G-specific antibodies.

Provided are thus RSV G-specific antibodies, according to the disclosure, which have heavy chain CDR1, CDR2 and CDR3 sequences and light chain CDR1, CDR2 and CDR3 sequences of antibody AT46, comprising the sequence of SEQ ID NO:1, SEQ ID NO:19, SEQ ID NO:37, SEQ ID NO:55, SEQ ID NO:73 and SEQ ID NO:91, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT46 does not show competitive binding with any other antibody, described herein, and can thus be advantageously combined with any other RSV G-specific antibody, described herein, and known RSV G-specific antibodies. Antibody AT46 is also preferred because it is capable of binding a conformational epitope of the RSV G protein. Conformational epitopes are generally highly conserved within different RSV strains, as described in more detail herein elsewhere. Thus, antibody AT46 has the advantage that is active against a wide range of RSV strains. Antibody AT46 is furthermore a particularly preferred antibody because it is capable of binding the G protein of both RSV A and B subtypes. Furthermore, antibody AT46 is capable of potentiating the RSV neutralizing activity of several RSV F-specific antibodies, and can thus be advantageously combined with a RSV F-specific antibody, such as palivizumab, AM14, AM16, AM22, AM23 and D25. The characteristics of antibody AT46 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT32, comprising the sequence of SEQ ID NO:2, SEQ ID NO:20, SEQ ID NO:38, SEQ ID NO:56, SEQ ID NO:74 and SEQ ID NO:92 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT32 is a preferred antibody because it has a particularly high RSV neutralizing capacity, having an IC50 of about 0.02 µg/ml. Antibody AT32 is also preferred because it is capable of binding an epitope of a G protein of RSV, which epitope is RIPNK (amino acids 188-192) of the G protein, and has a high binding affinity, having an affinity constant (KD) of about 0.6 nM for the RSV Ga protein (Table 7a). Thus, antibody AT32 binds to a different epitope as compared to previously disclosed RSV G antibodies. Antibody AT32 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. Furthermore, antibody AT32 is capable of potentiating the RSV neutralizing activity of RSV F-specific antibodies, and can thus be advantageously combined with a RSV F-specific antibody, such as palivizumab, AM14, AM16, AM22, AM23 and D25. The characteristics of antibody AT32 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT33, comprising the sequence of SEQ ID NO:3, SEQ ID NO:21, SEQ ID NO:39, SEQ ID NO:57, SEQ ID NO:75 and SEQ ID NO:93 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT33 is a preferred antibody because it has a particularly high RSV neutralizing capacity, having an IC50 of about 0.01 µg/ml. Antibody AT33 is also preferred because it is capable of binding an epitope of a G protein of RSV, which epitope is located between amino acids 51-160 and/or between amino acids 187-299 of the G protein. Thus, antibody AT33 binds to a different epitope as compared to previously disclosed RSV G antibodies. Antibody AT33 can thus be advantageously combined with such known antibodies, with RSV G-specific antibodies, disclosed herein, that are capable of binding to a conformational epitope and with RSV G-specific antibodies, disclosed herein, capable of binding the CX3C motif of the RSV G protein. Furthermore, antibody AT33 is capable of potentiating the RSV neutralizing activity of several RSV F-specific antibodies, and can thus be advantageously combined with a RSV F-specific antibody, such as palivizumab, AM14, AM16, AM22, AM23 and D25. The characteristics of antibody AT33 are summarized in Tables 4, 5 and 6.

In another embodiment an RSV G-specific antibody, according to the disclosure, comprises heavy chain CDR1, CDR2 and CDR3 sequences and light chain CDR1, CDR2 and CDR3 sequences of antibody AT34, comprising the sequence of SEQ ID NO:4, SEQ ID NO:22, SEQ ID NO:40, SEQ ID NO:58, SEQ ID NO:76 and SEQ ID NO:94 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT34 is a preferred antibody because it is capable of binding the G protein of both RSV A and B subtype. Antibody AT34 is also preferred because it is capable of binding within or close to the conserved motif and/or the CX3C motif of the RSV G protein. Antibody AT34 can thus be advantageously combined with RSV G-specific antibodies, disclosed herein, that are capable of binding to a conformational epitope and with RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT34 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT35, comprising the sequence of SEQ ID NO:5, SEQ ID NO:23, SEQ ID NO:41, SEQ ID NO:59, SEQ ID NO:77 and SEQ ID NO:95 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT35 is a preferred antibody because it has a particularly high RSV neutralizing capacity, having an IC50 of about 0.08 µg/ml. Antibody AT35 is also preferred because it is capable of binding an epitope of a G protein of RSV, which epitope is located between amino acids 51-160 and/or between amino acids 187-299 of the G protein. Thus, antibody AT35 binds to a different epitope as compared to previously disclosed RSV G antibodies. Antibody AT35 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. The characteristics of antibody AT35 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT36, comprising the sequence of SEQ ID NO:6, SEQ ID NO:24, SEQ ID NO:42, SEQ ID NO:60, SEQ ID NO:78 and SEQ ID NO:96 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT36 is a preferred antibody because it is capable of binding an epitope of a G protein of RSV, which epitope is located between amino acids 51-160 and/or between amino acids 187-299 of the G protein. Thus, antibody AT36 binds to a different epitope as compared to previously disclosed RSV G antibodies. Antibody AT36 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. The characteristics of antibody AT36 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT37, comprising the sequence of SEQ ID NO:7, SEQ ID NO:25, SEQ ID NO:43, SEQ ID NO:61, SEQ ID NO:79 and SEQ ID NO:97 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT37 is a preferred antibody because it is capable of binding an epitope of a G protein of RSV, which epitope is located between amino acids 51-160 and/or between amino acids 187-299 of the G protein. Thus, antibody AT37 binds to a different epitope as compared to previously disclosed RSV G antibodies. Antibody AT37 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. The characteristics of antibody AT37 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT39, comprising the sequence of SEQ ID NO:8, SEQ ID NO:26, SEQ ID NO:44, SEQ ID NO:62, SEQ ID NO:80 and SEQ ID NO:98 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT39 is a preferred antibody because it has a particularly high RSV neutralizing capacity, having an IC50 of about 0.10 µg/ml. Antibody AT39 is also preferred because it is capable of binding an epitope of a G protein of RSV, which epitope is located between amino acids 51-160 and/or between amino acids 187-299 of the G protein. Thus, antibody AT39 binds to a different epitope as compared to previously disclosed RSV G antibodies. Antibody AT39 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. The characteristics of antibody AT39 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT40, comprising the sequence of SEQ ID NO:9, SEQ ID NO:27, SEQ ID NO:45, SEQ ID NO:63, SEQ ID NO:81 and SEQ ID NO:99 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT40 is a preferred antibody because it is capable of binding the G protein of both RSV A and B subtype and because it has a particularly high RSV neutralizing capacity, having an IC50 of about 0.02 µg/ml. Furthermore, AT40 has a high binding affinity, having an affinity constant (KD) of about 0.2 nM for RSV-Ga and about 0.1 nM for Gb as measured by IBIS-iSPR technology (Table 7a). Antibody AT40 is also preferred because it is capable of binding the epitope FEVFNF (amino acids 165-170) of the RSV G protein. Antibody AT40 can thus be advantageously combined with RSV G-specific antibodies, disclosed herein, that are capable of binding to a conformational epitope and with RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT40 are summarized in Tables 4, 5, 6 and 7.

In another embodiment, an RSV G-specific antibody, according to the disclosure, comprises heavy chain CDR1, CDR2 and CDR3 sequences and light chain CDR1, CDR2 and CDR3 sequences of antibody AT42, comprising the sequence of SEQ ID NO:10, SEQ ID NO:28, SEQ ID NO:46, SEQ ID NO:64, SEQ ID NO:82 and SEQ ID NO:100 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT42 is a preferred antibody because it is capable of binding the G protein of both RSV A and B subtype. Antibody AT42 is also preferred because it is capable of binding a conformational epitope of the RSV G protein, which domain is at least partially within the conserved domain (amino acids 164-172) and/or the CX3C binding domain (CWAIC) because AT42 competes with antibody 131-2G and partially competes with antibody 3D3 (Table 4 and FIG. 5). Conformational epitopes are generally highly conserved within different RSV strains, as described in more detail herein elsewhere. Thus, antibody AT42 has the advantage that is active against a wide range of RSV strains. Furthermore, because it binds a conformational epitope, antibody AT42 can be advantageously combined with RSV G-specific antibodies, disclosed herein, that are capable of binding to the CX3C motif of the RSV G protein and with RSV G-specific antibodies, disclosed herein, that are capable of binding an epitope of a G protein of Respiratory Syncytial Virus, which epitope is located between amino acids 51-160 and/or between amino acids 187-299 of the G protein. Furthermore, AT42 has a high binding affinity, having an affinity constant (KD) of about 1.3 nM for RSV Ga and about 0.3 nM for Gb as measured by IBIS-iSPR technology (Table 7). The characteristics of antibody AT42 are summarized in Tables 4, 5, 6 and 7.

In another embodiment, an RSV G-specific antibody, according to the disclosure, comprises heavy chain CDR1, CDR2 and CDR3 sequences and light chain CDR1, CDR2 and CDR3 sequences of antibody AT43, comprising the sequence of SEQ ID NO:11, SEQ ID NO:29, SEQ ID NO:47, SEQ ID NO:65, SEQ ID NO:83 and SEQ ID NO:101 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT43 is a preferred antibody because it is capable of binding a conformational epitope of the RSV G protein. Conformational epitopes are generally highly conserved within different RSV strains, as described in more detail herein elsewhere. Thus, antibody AT43 has the advantage that is active against a wide range of RSV strains. Furthermore, because it binds a conformational epitope, antibody AT43 can be advantageously combined with RSV G-specific antibodies, disclosed herein, that are capable of binding to the CX3C motif of the RSV G protein and with RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT43 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT44, comprising the sequence of SEQ ID NO:12, SEQ ID NO:30, SEQ ID NO:48, SEQ ID NO:66, SEQ ID NO:84 and SEQ ID NO:102 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT44 is a preferred antibody because it is capable of binding the G protein of both RSV A and B subtype and because it has a particularly high RSV neutralizing capacity, having an IC50 of about 0.02 µg/ml. Furthermore, AT44 has a high binding affinity, having an affinity constant (KD) of about 0.1 nM for both RSV Ga and Gb as measured by IBIS-iSPR technology (Table 7a and b). Antibody AT44 is also preferred because it is capable of binding the epitope EVFNF (amino acids 166-170) of the RSV G protein. Antibody AT44 can thus be advantageously combined with RSV G-specific antibodies, disclosed herein, that are capable of binding to a conformational epitope and with RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT44 are summarized in Tables 4, 5, 6 and 7.

In another embodiment, an RSV G-specific antibody, according to the disclosure, comprises heavy chain CDR1, CDR2 and CDR3 sequences and light chain CDR1, CDR2 and CDR3 sequences of antibody AT45, comprising the sequence of SEQ ID NO:13, SEQ ID NO:31, SEQ ID NO:49, SEQ ID NO:67, SEQ ID NO:85 and SEQ ID NO:103 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT45 is a preferred antibody because it is capable of binding the G protein of both RSV A and B subtype and because it has a particularly high RSV neutralizing capacity, having an IC50 of about 0.11 µg/ml. Antibody AT45 is also preferred because it is capable of binding within or in the proximity of the CX3C motif of the RSV G protein. Antibody AT45 can thus be advantageously combined with RSV G-specific antibodies, disclosed herein, that are capable of binding to a conformational epitope and RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT45 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT47, comprising the sequence of SEQ ID NO:14, SEQ ID NO:32, SEQ ID NO:50, SEQ ID NO:68, SEQ ID NO:86 and SEQ ID NO:104 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT47 is a preferred antibody because it is capable of binding a conformational epitope of the RSV G protein. Conformational epitopes are generally highly conserved within different RSV strains, as described in more detail herein elsewhere. Thus, antibody AT47 has the advantage that is active against a wide range of RSV strains. Furthermore, because it binds a conformational epitope, antibody AT47 can be advantageously combined with RSV G-specific antibodies, disclosed herein, that are capable of binding to the CX3C motif of the RSV G protein and with RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT47 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT49, comprising the sequence of SEQ ID NO:15, SEQ ID NO:33, SEQ ID NO:51, SEQ ID NO:69, SEQ ID NO:87 and SEQ ID NO:105 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT49 is a preferred antibody because it is capable of binding the G protein of both RSV A and B subtype. Antibody AT49 is also preferred because it is capable of binding within or close to the CX3C motif of the RSV G protein. Antibody AT49 can thus be advantageously combined with RSV G-specific antibodies, disclosed herein, that are capable of binding to a conformational epitope and RSV G-specific antibodies, disclosed herein, that are capable of binding an epitope of a G protein of Respiratory Syncytial Virus, which epitope is located between amino acids 51-160 and/or between amino acids 187-299 of the G protein. The characteristics of antibody AT49 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT50, comprising the sequence of SEQ ID NO:16, SEQ ID NO:34, SEQ ID NO:52, SEQ ID NO:70, SEQ ID NO:88 and SEQ ID NO:106 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT50 is a preferred antibody because it is capable of binding an epitope of a G protein of RSV which epitope is located between amino acids 51-160 and/or between amino acids 187-299 of the G protein. Thus, antibody AT50 binds to a different epitope as compared to previously disclosed RSV G antibodies. Antibody AT50 can thus be advantageously combined with such known antibodies, with RSV G-specific antibodies, disclosed herein, that are capable of binding to a conformational epitope and with RSV G-specific antibodies, disclosed herein, that are capable of binding the CX3C motif of the RSV G protein. The characteristics of antibody AT50 are summarized in Tables 4, 5 and 6.

In another embodiment, an RSV G-specific antibody, according to the disclosure, comprises heavy chain CDR1, CDR2 and CDR3 sequences and light chain CDR1, CDR2 and CDR3 sequences of antibody AT51, comprising the sequence of SEQ ID NO:17, SEQ ID NO:35, SEQ ID NO:53, SEQ ID NO:71, SEQ ID NO:89 and SEQ ID NO:107 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical thereto. Antibody AT51 is a preferred antibody because it is capable of binding an epitope of a G protein of RSV, which epitope is located between amino acids 51-160 and/or between amino acids 187-299 of the G protein. Thus, antibody AT51 binds to a different epitope as compared to previously disclosed RSV G antibodies. Antibody AT51 can thus be advantageously combined with such known antibodies, with RSV G-specific antibodies, disclosed herein, that are capable of binding to a conformational epitope and RSV G-specific antibodies, disclosed herein, that are capable of binding the CX3C motif of the RSV G protein. The characteristics of antibody AT51 are summarized in Tables 4, 5 and 6.

Preferably, an RSV G-specific antibody, according to the disclosure, comprises heavy chain CDR1, CDR2 and CDR3 sequences and light chain CDR1, CDR2 and CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the sequences of the same antibody of the disclosure as depicted in table 1.

As is well known by the skilled person, a heavy chain of an antibody is the larger of the two types of chains making up an immunoglobulin molecule. A heavy chain comprises constant domains and a variable domain, which variable domain is involved in antigen binding. A light chain of an antibody is the smaller of the two types of chains making up an immunoglobulin molecule. A light chain comprises a constant domain and a variable domain. The variable domain is, together with the variable domain of the heavy chain, involved in antigen binding.

Complementary-determining regions (CDRs) are the hypervariable regions present in heavy chain variable domains and light chain variable domains. The CDRs of a heavy chain and the connected light chain of an antibody together form the antigen-binding site.

Based on the human RSV G-specific antibodies depicted in table 1, it is possible to produce an immunoglobulin chain or functional equivalent thereof comprising at least one CDR sequence of a human immunoglobulin variable domain depicted in table 1, which is specific for RSV G protein. Further provided, is thus an isolated, recombinant or synthetic immunoglobulin chain or functional equivalent thereof, comprising at least one CDR sequence of a human immunoglobulin variable region depicted in table 1. In a preferred embodiment, a human antibody is provided because the use of a human antibody diminishes the chance of side-effects due to an immunological reaction in a human individual. Optionally, the at least one CDR sequence is optimized, preferably in order to improve binding efficacy or stability. This is, for instance, done by mutagenesis experiments where after the stability and/or binding efficacy of the resulting compounds are preferably tested and an improved RSV G-specific antibody is selected.

A skilled person is well capable of generating variants comprising at least one altered CDR sequence, according to the disclosure. For instance, conservative amino acid substitution is applied. It is also possible to alter at least one CDR sequence depicted in table 1 in order to generate a variant antibody, or a functional part thereof, with at least one altered property as compared to the original antibody. Preferably, an antibody or functional part is provided comprising a CDR sequence, which is at least 70% identical to a CDR sequence as depicted in table 1, so that the favorable binding characteristics of an RSV G-specific antibody, according to the disclosure, are at least in part maintained or even improved. A CDR sequence, as depicted in table 1, is preferably altered such that the resulting antibody or functional part comprises at least one improved property, such as, for instance, an improved binding affinity, selectivity and/or stability, as compared to the original antibody. Variant antibodies or functional parts thereof comprising an amino acid sequence, which is at least 70% identical to a CDR sequence as depicted in table 1, are, therefore, also within the scope of the present disclosure. Various methods are available in the art for altering an amino acid sequence. For instance, a heavy chain or light chain sequence with a desired CDR sequence is artificially synthesized. Preferably, a nucleic acid sequence encoding a CDR sequence, according to the disclosure, is mutated, for instance, using random- or site-directed mutagenesis.

Besides optimizing CDR sequences in order to improve binding efficacy or stability, it is often advantageous to optimize at least one sequence in at least one of the framework regions. This is preferably done in order to improve binding efficacy or stability. Framework sequences are, for instance, optimized by mutating a nucleic acid molecule encoding such framework sequence where after the characteristics of the resulting antibody, or functional part, are preferably tested. This way, it is possible to obtain improved antibodies or functional parts. In a preferred embodiment, human germline sequences are used for framework regions in antibodies or functional parts thereof or immunoglobulin chains or functional equivalents according to the disclosure. The use of germline sequences preferably minimizes the risk of immunogenicity of the antibodies or functional parts, immunoglobulin chains or functional equivalents, because these sequences are less likely to contain somatic alterations, which are unique to individuals from which the framework regions are derived, and may cause an immunogenic response when applied to another human individual.

In a preferred embodiment, RSV G-specific antibodies, according to the disclosure, are provided that are capable of binding an epitope of a G protein of RSV, which epitope is a non-linear or conformational epitope. The term "non-linear or conformational epitope" is herein defined as an epitope, which is formed by the amino acid sequence and the three-dimensional shape of an antigen (e.g., folding). The amino acids making up the epitope can be relatively few in number and widely spread along the length of the molecule. Such epitope is brought into the correct conformation via folding of the antigen. In general, antibodies recognizing conformational epitopes afford broader specificity and, therefore, more effective therapeutic application for ameliorating or preventing RSV infection than antibodies able to bind only linear epitopes because conformational epitopes are more conserved. In order to obtain the necessary correct folding of a protein, variation within amino acids which are part of a conformational epitope is limited. Thus, the antibodies capable of binding to a conformational epitope, disclosed herein, have the advantage that they are active against a wider range of RSV strains than antibodies recognizing linear epitopes. An RSV G-specific antibody, according to the disclosure, capable of binding a conformational epitope of a G protein of RSV is particularly suitable for combination with one or more RSV G-specific antibodies, according to the disclosure, capable of binding to another epitope, such as a linear epitope of RSV G protein which epitope is located between amino acids 51-158 and/or between amino acids 189-299 of the G protein or an epitope, which comprises the CX3C motif of the RSV G protein.

Particularly preferred RSV G-specific antibodies, which bind to conformational epitopes, are the antibodies designated AT46 AT42, AT43 and AT47 which have heavy chain sequences of SEQ ID NOS:109, 118, 119 and 122 as depicted in table 1, respectively, and light chain sequences of SEQ ID NOS:127, 136, 137 and 140 as depicted in table 1, respectively. The heavy and light chain CDR sequences of these preferred antibodies are also depicted in table 1, namely SEQ ID NOS:1, 10, 11 and 14 being the heavy chain CDR1 sequences of these antibodies, SEQ ID NOS:19, 28, 29 and 32 being the heavy chain CDR2 sequences of these antibodies, SEQ ID NOS:37, 46, 47 and 50 being the heavy chain CDR3 sequences of these antibodies, SEQ ID NOS: 55, 64, 65 and 68 being the light chain CDR1 sequences of these antibodies, SEQ ID NOS:73, 82, 83 and 86 being the light chain CDR2 sequences of these antibodies, and SEQ ID NOS:91, 100, 101 and 104 being the light chain CDR3 sequences of these antibodies.

The disclosure thus provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO: 1, 10, 11 and 14, and/or a heavy chain CDR2 sequence comprising a sequence which is at least 70% identical to a sequence selected from the group consisting of SEQ ID NO: 19, 28, 29 and 32, and/or a heavy chain CDR3 sequence comprising a sequence which is at least 70% identical to a sequence selected from the group consisting of SEQ ID NO: 37, 46, 47 and 50, and/or a light chain CDR1 sequence comprising a sequence which is at least 70% identical to a sequence selected from the group consisting of SEQ ID NO: 55, 64, 65 and 68, and/or a light chain CDR2 sequence comprising a sequence which is at least 70% identical to a sequence selected from the group consisting of SEQ ID NO: 73, 82, 83 and 86, and/or a light chain CDR3 sequence comprising a sequence which is at least 70% identical to a sequence selected from the group consisting of SEQ ID NO: 91, 100, 101 and 104.

Preferably, the antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% identical to these sequences. As described before, the six CDR sequences of one given antibody of interest (or sequences at least 70% identical thereto) are typically combined. An antibody, functional part, immunoglobulin or functional equivalent, according to the disclosure, thus preferably comprises CDR sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to the heavy chain CDR1, CDR2 and CDR3 sequences and the light chain CDR1, CDR2 and CDR3 sequences of antibody AT46 AT42, AT43 or AT47.

The terms "AT46," "AT42," "AT43," and "AT47," as used herein, encompass all antibodies with the indicated heavy chain and light chain sequences, for instance, isolated and/or purified or recombinantly produced.

The disclosure also provides RSV G-specific antibodies, which are capable of binding to or close to the CX3C motif of the RSV G protein. An RSV G-specific antibody, according to the disclosure, capable of binding the CX3C motif of the RSV G protein is particularly suitable for combination with one or more RSV G-specific antibodies, according to the disclosure, capable of binding to another epitope, such as an epitope of RSV G protein, which epitope is located between amino acids 51-158 and/or between amino acids 189-299 of the G protein or an epitope capable of binding a conformational epitope of a G protein of RSV.

Particularly preferred RSV G-specific antibodies, according to the disclosure, which are capable of binding the CX3C motif of the RSV G protein are the antibodies designated AT34, AT40, AT49, AT44 and AT45, which have heavy chain sequences of SEQ ID NOS:112, 117, 123, 120 and 121 as depicted in table 1, respectively, and light chain sequences of SEQ ID NOS:130, 135, 141, 138 and 139 as depicted in table 1, respectively. The heavy and light chain CDR sequences of these preferred antibodies are also depicted in table 1, namely SEQ ID NOS:4, 9, 12, 13 and 15 being the heavy chain CDR1 sequences of these antibodies, SEQ ID NOS:22, 27, 30, 31 and 33 being the heavy chain CDR2 sequences of these antibodies, SEQ ID NOS:40, 45, 48, 49 and 51 being the heavy chain CDR3 sequences of these antibodies, SEQ ID NOS:58, 63, 66, 67 and 69 being the light chain CDR1 sequences of these antibodies, SEQ ID NOS:76, 81, 84, 85 and 87 being the light chain CDR2 sequences of these antibodies, and SEQ ID NOS:94, 99, 102, 103 and 105 being the light chain CDR3 sequences of these antibodies.

The disclosure thus provides an isolated, synthetic or recombinant antibody or functional part thereof, or immunoglobulin chain or functional equivalent thereof comprising:

a heavy chain CDR1 sequence comprising a sequence which is at least 70% identical to a sequence selected from the group consisting of SEQ ID NO: 4, 9, 12, 13 and 15, and/or a heavy chain CDR2 sequence comprising a sequence which is at least 70% identical to a sequence selected from the group consisting of SEQ ID NO: 22, 27, 30, 31 and 33, and/or a heavy chain CDR3 sequence comprising a sequence which is at least 70% identical to a sequence selected from the group consisting of SEQ ID NO: 40, 45, 48, 49 and 51, and/or a light chain CDR1 sequence comprising a sequence which is at least 70% identical to a sequence selected from the group consisting of SEQ ID NO: 58, 63, 66, 67 and 69, and/or a light chain CDR2 sequence comprising a sequence which is at least 70% identical to a sequence selected from the group consisting of SEQ ID NO: 76, 81, 84, 85 and 87, and/or a light chain CDR3 sequence comprising a sequence which is at least 70% identical to a sequence selected from the group consisting of SEQ ID NO: 94, 99, 102, 103 and 105.

Preferably, the antibody or functional part or immunoglobulin chain or functional equivalent comprises heavy chain CDR1, CDR2 and/or CDR3 sequences and/or light chain CDR1, CDR2 and/or CDR3 sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% identical to these sequences. As described before, the six CDR sequences of one given antibody of interest (or sequences at least 70% identical thereto) are typically combined. An antibody, functional part, immunoglobulin or functional equivalent, according to the disclosure, thus preferably comprises CDR sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to the heavy chain CDR1, CDR2 and CDR3 sequences and the light chain CDR1, CDR2 and CDR3 sequences of antibody AT34, AT40, AT49, AT44 or AT45.

The terms "AT34," "AT40," "AT49," "AT44," and "AT45," as used herein, encompass all antibodies with the heavy chain and light chain sequences, for instance, isolated and/or purified or recombinantly produced.

In a preferred embodiment, at least two RSV G-specific antibodies, according to the disclosure, are combined because with a combination of different antibodies RSV is more effectively counteracted. Particularly, preferred is the combination of at least two RSV G-specific antibodies, according to the disclosure, which bind to different epitopes of the G protein. By combining at least two RSV G-specific antibodies, which bind to different epitopes on the RSV G protein, two or more different epitopes of RSV G protein are recognized during the same therapy. This way, a more potent anti-RSV response is obtained. With a stronger response to RSV, such combination will result in more effective treatment and/or prevention of an RSV infection and/or an RSV-related disorder.

The disclosure, therefore, provides a composition comprising a combination of at least two RSV G-specific antibodies, according to the disclosure. In a preferred embodiment, a composition, according to the disclosure, comprises at least two RSV G-specific antibodies selected from at least two of the following groups:

1) an RSV G-specific antibody, according to the disclosure, capable of binding an epitope of a G protein of RSV, which epitope is located between amino acids 51-160 and/or between amino acids 187-299 of the G protein. Preferred antibodies are AT35, AT37, AT39, AT43, AT51, AT47, AT32, AT33, AT36 and AT50, which have heavy chain sequences of SEQ ID NOS: 113, 115, 116, 119, 125, 122, 110, 111, 114 and 124 as depicted in table 1, respectively, and light chain sequences of SEQ ID NOS:131, 133, 134, 137, 143, 140, 128, 129, 132 and 142 as depicted in table 1, respectively;

2) an RSV G-specific antibody, according to the disclosure, capable of binding a conformational epitope of an RSV G protein. Preferred antibodies are AT46, AT42, AT43 and AT47, which have heavy chain sequences of SEQ ID NOS:109, 118, 119 and 122 as depicted in table 1, respectively, and light chain sequences of SEQ ID NOS:127, 136, 137 and 140 as depicted in table 1, respectively; and 3) an RSV G-specific antibody, according to the disclosure, capable of binding the CX3C motif of the RSV G protein. Preferred antibodies are AT34, AT40, AT49, AT44 and AT45, which have heavy chain sequences of SEQ ID NOS:112, 117, 123, 120 and 121 as depicted in table 1, respectively, and light chain sequences of SEQ ID NOS:130, 135, 141, 138 and 139 as depicted in table 1, respectively.

A particularly preferred RSV G-specific antibody, according to the disclosure, is AT46, which has heavy and light chain sequences SEQ ID NO:109 and SEQ ID NO:127 as depicted in table 1. This antibody does not show competitive binding with any other antibody described herein. AT46 can thus be advantageously combined with any other RSV G-specific antibody, described herein, including other antibodies, which are capable of binding a conformational epitope, i.e., AT42, AT43 and AT47, which have heavy and light chain sequences as depicted in table 1. Thus, any combination of two RSV G-specific antibodies, according to the disclosure, which comprises at least AT46 is a combination of two antibodies binding to different epitopes of the RSV G protein. Antibody AT46 can thus be advantageously used in combination with any other RSV G-specific antibody, according to the disclosure, and any known RSV G-specific antibody. Antibody AT46 is furthermore a particularly preferred antibody, according to the disclosure, because it is capable of binding the G protein of both RSV A and B subtypes and has a high binding affinity. Furthermore, antibody AT46 is capable of potentiating the RSV neutralizing activity of several RSV F-specific antibodies. The characteristics of antibody AT46 are summarized in Tables 4, 5 and 6. Thus, in a preferred embodiment of the disclosure, a composition comprises a combination of AT46 and another RSV G-antibody, according to the disclosure.

Other preferred combinations of two RSV G-specific antibodies are depicted in tables 2 and 3. Therefore, in another preferred embodiment of the disclosure, a composition comprises a combination of two RSV G-antibodies, according to the disclosure, wherein the combination is selected from table 2. More preferably, the combination is selected from table 3. One or more RSV G-specific antibodies, according to the disclosure, that are capable of binding a conformational epitope of RSV G protein are also advantageously combined with RSV G-specific antibodies that are already known, such as antibodies disclosed in US 2010-0285022. One or more RSV G-specific antibodies, according to the disclosure, are capable of binding to an epitope of RSV G protein, which epitope is located between amino acids 51-158 and/or between amino acids 189-299 of the G protein are also advantageously combined with RSV G-specific antibodies that are already known, such as antibodies disclosed in US 2010-0285022.

The disclosure, therefore, also provides a composition comprising an RSV G-specific antibody, according to the disclosure, capable of binding an epitope of a G protein of RSV, which epitope is located between amino acids 51-160 and/or between amino acids 187-299 of the G protein (preferably, antibody AT35, AT37, AT39, AT43, AT51, AT47, AT32, AT33, AT36 or AT50, which have heavy chain sequences of SEQ ID NOS:113, 115, 116, 119, 125, 122, 110, 111, 114 and 124, as depicted in table 1, respectively, and light chain sequences of SEQ ID NOS:131, 133, 134, 137, 143, 140, 128, 129, 132 and 142, as depicted in table 1, respectively), and a known RSV G-specific antibody, which is capable of binding an epitope of a G protein of RSV, which epitope is located between amino acids 164-186 of the G protein. Also provided is a composition comprising an RSV G-specific antibody, according to the disclosure, capable of binding a conformational epitope of an RSV G protein (preferably, antibody AT46, AT42, AT43 or AT47, which have heavy chain sequences of SEQ ID NOS:109, 118, 119 and 122, as depicted in table 1, respectively, and light chain sequences of SEQ ID NOS:127, 136, 137 and 140, as depicted in table 1, respectively), and a known RSV G-specific antibody, which is capable of binding an epitope of a G protein of RSV, which epitope is located between amino acids 164-186 of the G protein.

Particularly preferred, are combinations of three RSV G-specific antibodies, according to the disclosure, which bind to different epitopes of the G protein. By combining at least three of such RSV G-specific antibodies at least three different epitopes of RSV G protein are recognized during the same therapy. This way, often an even stronger immunogenic response to RSV is obtained and a higher antibody specificity against RSV is reached as compared to the use of one antibody or a combination of two antibodies. As indicated above, with a stronger immunogenic response to and/or a higher specificity against RSV, a more effective treatment and/or prevention of an RSV infection and/or an RSV-related disorder can be achieved. A combination of three RSV G-specific antibodies, according to the disclosure, preferably comprises three antibodies that do not compete for the same or overlapping epitopes in the RSV G protein. The disclosure, therefore, provides a composition comprising a combination of three RSV G-specific antibodies, according to the disclosure, wherein the combination is selected from the group consisting of:

AT34+AT46+AT42;
AT40+AT46+AT42;
AT44+AT46+AT42;
AT45+AT46+AT42;
AT49+AT46+AT42;

which antibodies have heavy and light chain sequences as depicted in table 1.

Other preferred combinations of three RSV G-specific antibodies, according to the disclosure, are AT34, AT33 and AT46; and AT36, AT46 and AT45. These combinations of three RSV G-specific antibodies, according to the disclosure, have been proven to be able to non-competitively bind the RSV G protein using IBIS-iSPR technology (IBIS Technologies BV Hengelo, the Netherlands).

Other preferred combinations of two or three antibodies are:

AT42+AT33;
AT42+AT44;
AT40+AT46+AT32;
AT40+AT46+AT33;
AT44+AT42+AT33;
AT44+AT46+AT33.

These combinations of anti-RSV G antibodies were able to neutralize the virus without the addition of complement factors as demonstrated in example 2 and FIG. 3A.

Preferred RSV G-specific antibodies, according to the disclosure, are capable of binding the G protein of both RSV subtype A and RSV subtype B because such antibodies can be used for counteracting both RSV subtypes. However, RSV G-specific antibodies, according to the disclosure, capable of binding the G protein of RSV subtype A only are also particularly useful. For instance, RSV G-specific antibodies, according to the disclosure, that only bind the G protein of RSV subtype A, bind to a different epitope in the G protein of RSV than RSV G-specific antibodies, described herein, that bind to both subtype A and B RSV. Therefore, they are particularly suitable to be used in combination with RSV G-specific antibodies that bind to both subtype A and B RSV, as described above. Furthermore, RSV G-specific antibodies, according to the disclosure, that only bind the G protein of RSV subtype A are particularly suitable for diagnosing RSV subtype A.

Preferred RSV G-specific antibodies, according to the disclosure, have a high affinity for the RSV G protein. Measurement of the affinity constant and specificity of binding between antigen and antibody is preferred in determining the efficacy of prophylactic, therapeutic, diagnostic and research methods using anti-RSV G antibodies of the disclosure. "Binding affinity" generally refers to the strength of the sum total of the noncovalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity can generally be represented by the equilibrium dissociation constant (KD), which is calculated as the ka to kd ratio (see, e.g., Chen, Y., et al., (1999) J. Mol Biol 293:865-881, and Table 7 and FIG. 7). Affinity can be measured by common methods known in the art, such as, for instance, a surface plasmon resonance (SPR) assay such as BiaCore or IBIS-iSPR instrument at IBIS Technologies BV (Hengelo, the Netherlands) or solution phase assays, such as Kinexa. Preferably, an RSV G-specific antibody, according to the disclosure, has an affinity constant (KD) as measured by IBIS-iSPR technology of at most 10 nM, more preferably at most 5 nM, more preferably at most 2 nM, more preferably at most 1 nM, more preferably at most 0.5 nM, more preferably at most 0.3 nM, more preferably at most 0.1 nM.

Other preferred RSV G-specific antibodies, according to the disclosure, have a high RSV neutralizing activity in the presence of complement. RSV neutralizing activity is, for instance, determined in vitro in the presence of complement, for instance, rabbit serum complement. Rabbit serum complement is a mixture of complement factors prepared from the serum of rabbits and is commercially available from, for instance, GTi Diagnostics or Calbiochem. An in vitro neutralization assay in the presence of complement is, for instance, performed as described in the Examples. Preferably, an RSV G-specific antibody, according to the disclosure, is capable of neutralizing RSV in vitro in the presence of complement with an IC50<500 ng/ml, more preferably with an IC50<400 ng/ml, more preferably with an IC50<350 ng/ml, more preferably with an IC50>300 ng/ml, more preferably with an IC50<250 ng/ml, more preferably with an IC50<200 ng/ml, more preferably with an IC50<150 ng/ml, most preferably with IC50<125 ng/ml. Further provided is, therefore, an RSV G-specific antibody, according to the disclosure, which has an RSV neutralizing capacity in vitro in the presence of complement with an IC50<500 ng/ml, more preferably with an IC50<400 ng/ml, more preferably with an IC50<350 ng/ml, more preferably with an IC50>300 ng/ml, more preferably with an IC50<250 ng/ml, more preferably with an IC50<200 ng/ml, more preferably with an IC50<150 ng/ml, most preferably with IC50<125 ng/ml. In one embodiment, an RSV G-specific antibody, according to the disclosure, has RSV neutralizing capacity in vitro in the presence of complement with an IC50<100 ng/ml, such as <80 ng/ml, or <25 ng/ml.

In a preferred embodiment, an RSV G-specific antibody, according to the disclosure, comprises a heavy chain sequence and/or light chain sequence, or a sequence which has at least 70% sequence identity thereto, as depicted in table 1. Also provided is, therefore, an antibody or functional part, or immunoglobulin chain or functional equivalent, having a heavy chain sequence comprising a sequence which is at least 70% identical to a sequence selected from the group consisting of SEQ ID NO:109-125 and/or having a light chain sequence which is at least 70% identical to a sequence selected from the group consisting of SEQ ID NO:127-143.

Preferably, an RSV G-specific antibody, according to the disclosure, comprises a heavy chain sequence which is at least 75%, more preferably at least 80%, more preferably at least 85%, more preferably at least 86%, more preferably at least 87%, more preferably at least 88%, more preferably at least 89%, more preferably at least 90% identical to a sequence selected from the group consisting of SEQ ID NO:109-125 and/or a light chain which is at least 75%, more preferably at least 80%, more preferably at least 85%, more preferably at least 86%, more preferably at least 87%, more preferably at least 88%, more preferably at least 89%, more preferably at least 90% identical to a sequence selected from the group consisting of SEQ ID NO:127-143. Most preferably, an RSV G-specific antibody, according to the disclosure, comprises a heavy chain sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% identical to a sequence selected from the group consisting of SEQ ID NO:109-125 and/or a light chain sequence which is at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% identical to a sequence selected from the group consisting of SEQ ID NO:127-143. The higher the identity, the more closely an antibody resembles an antibody depicted in table 1.

An antibody or functional part or immunoglobulin chain or functional equivalent, according to the disclosure, preferably comprises a heavy chain as well as a light chain, which resemble the heavy and the light chain of the same antibody depicted in table 1. Thus, in a preferred embodiment an RSV G-specific antibody, according to the disclosure, comprises a heavy chain sequence of a given antibody, preferably antibody AT46, comprising the sequence of SEQ ID NO:109 and a light chain sequence of the same antibody, preferably AT46, comprising the sequence of SEQ ID NO:127, or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical thereto.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT32, comprising the sequence of SEQ ID NO:110 and the light chain sequence of antibody AT32, comprising the sequence of SEQ ID NO:128.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT33, comprising the sequence of SEQ ID NO:111 and a light chain sequence comprising the sequence of SEQ ID NO:129.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT34, comprising the sequence of SEQ ID NO:112 and a light chain sequence of antibody AT34, comprising the sequence of SEQ ID NO:130.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT35, comprising the sequence of SEQ ID NO:113 and a light chain sequence of antibody AT35, comprising the sequence of SEQ ID NO:131.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT36, comprising the sequence of SEQ ID NO:114 and a light chain sequence of antibody AT36, comprising the sequence of SEQ ID NO:132.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT37, comprising the sequence of SEQ ID NO:115 and a light chain sequence of antibody AT37, comprising the sequence of SEQ ID NO:133.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT39, comprising the sequence of SEQ ID NO:116 and a light chain sequence of antibody AT39, comprising the sequence of SEQ ID NO:134.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT40, comprising the sequence of SEQ ID NO:117 and a light chain sequence of antibody AT40, comprising the sequence of SEQ ID NO:135.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 100% sequence identity with the heavy chain sequence of antibody AT42, comprising the sequence of SEQ ID NO:118 and a light chain sequence of antibody AT42, comprising the sequence of SEQ ID NO:136.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT43, comprising the sequence of SEQ ID NO:119 and a light chain sequence of antibody AT43, comprising the sequence of SEQ ID NO:137.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT44, comprising the sequence of SEQ ID NO:120 and a light chain sequence of antibody AT44, comprising the sequence of SEQ ID NO:138.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT45, comprising the sequence of SEQ ID NO:121 and a light chain sequence of antibody AT45, comprising the sequence of SEQ ID NO:139.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT47, comprising the sequence of SEQ ID NO:122 and a light chain sequence of antibody AT47, comprising the sequence of SEQ ID NO:140.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT49, comprising the sequence of SEQ ID NO:123 and a light chain sequence of antibody AT49, comprising the sequence of SEQ ID NO:141.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT50, comprising the sequence of SEQ ID NO:124 and a light chain sequence of antibody AT50, comprising the sequence of SEQ ID NO:142.

In another embodiment, an RSV G-specific antibody, according to the disclosure, or functional part thereof comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain sequence of antibody AT51, comprising the sequence of SEQ ID NO:125 and a light chain sequence of antibody AT51, comprising the sequence of SEQ ID NO:143.

Preferably, an RSV G-specific antibody, according to the disclosure, or functional part thereof comprises sequences that are at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, identical to the heavy and light chain sequences of antibody AT46, AT32, AT33, AT34, AT35, AT36, AT37, AT39, AT40, AT42, AT43, AT44, AT45, AT47, AT49, AT50 or AT51 as depicted in table 1.

The disclosure further provides an isolated, synthetic or recombinant nucleic acid sequence with a length of at least 15 nucleotides, or a functional equivalent thereof, encoding at least one CDR sequence of an antibody or functional part, or immunoglobulin chain or functional equivalent, according to the disclosure. Preferably, a nucleic acid, according to the disclosure, has a length of at least 30 nucleotides, more preferably at least 50 nucleotides, more preferably at least 75 nucleotides. A nucleic acid, according to the disclosure, is, for instance, isolated from a B-cell which is capable of producing an RSV G-specific antibody, according to the disclosure. In a preferred embodiment, a nucleic acid encoding an RSV G-specific antibody, according to the disclosure, is provided.

As used herein, "an isolated, synthetic or recombinant nucleic acid sequence with a length of at least 15 nucleotides, or a functional equivalent thereof, encoding at least one CDR sequence of an antibody or functional part thereof, or immunoglobulin chain or functional equivalent thereof, according to the disclosure," is herein also referred to as "a nucleic acid sequence or functional equivalent thereof, according to the disclosure."

As used herein, a nucleic acid molecule or nucleic acid sequence of the disclosure, preferably comprises a chain of nucleotides, more preferably DNA and/or RNA. In other embodiments, a nucleic acid molecule or nucleic acid sequence of the disclosure comprises other kinds of nucleic acid structures such as, for instance, a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid sequence" also encompasses a chain comprising non-natural nucleotides, modified nucleotides and/or non-nucleotide building blocks, which exhibit the same function as natural nucleotides.

Nucleic acid sequences encoding preferred heavy chain and light chain CDRs of antibodies AT46, AT32, AT33, AT34, AT35, AT36, AT37, AT39, AT40, AT42, AT43, AT44, AT45, AT47, AT49, AT50 and AT51 are depicted in table 1. Nucleic acid sequences encoding a heavy or light chain CDR of a RSV G-specific antibody, according to the disclosure, which differ from the CDR nucleic acid sequences depicted in table 1 but have nucleic acid codons encoding for the same amino acids of the heavy or light chain CDR are also encompassed by the disclosure. Nucleic acid sequences encoding a heavy or light chain CDR of a RSV G-specific antibody depicted in table 1 which has been altered, for instance, through conservative amino acid substitution, whereby an amino acid residue is substituted by another residue with generally similar properties (size, hydrophobicity, etc.), are also encompassed by the disclosure, as long as the resulting CDR has at least 70% sequence identity with a CDR depicted in table 1.

A preferred nucleic acid sequence, according to the disclosure, comprises:
  a heavy chain CDR1 encoding sequence which has at least 70% sequence identity to a sequence which is selected from the group consisting of SEQ ID NO:145-161, and/or
  a heavy chain CDR2 encoding sequence which has at least 70% sequence identity to a sequence which is selected from the group consisting of SEQ ID NO:163-179, and/or
  a heavy chain CDR3 encoding sequence which has at least 70% sequence identity to a sequence which is selected from the group consisting of SEQ ID NO:181-197, and/or
  a light chain CDR1 encoding sequence which has at least 70% sequence identity to a sequence which is selected from the group consisting of SEQ ID NO:199-215, and/or
  a light chain CDR2 encoding sequence which has at least 70% sequence identity to a sequence which is selected from the group consisting of SEQ ID NO:217-233, and/or
  a light chain CDR3 encoding sequence which has at least 70% sequence identity to a sequence which is selected from the group consisting of SEQ ID NO:235-251.

A nucleic acid sequence, according to the disclosure, preferably comprises a sequence which has at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity to the sequence. Preferably, the nucleic acid sequence comprises at least one CDR encoding sequence. Further provided is a nucleic acid sequence or functional equivalent thereof comprising a sequence which has at least 70% sequence identity, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity to a nucleic acid sequence selected from the group consisting of SEQ ID NO:145-161, SEQ ID NO:163-179, SEQ ID NO: 199-215, SEQ ID NO: 199-215, SEQ ID NO: 217-233, and SEQ ID NO: 235-251, the nucleic acid sequence or functional equivalent having at least 15 nucleotides. As described before, the six CDR sequences of one given antibody of interest (or sequences at least 70% identical thereto) are typically combined. A preferred nucleic acid sequence, according to the disclosure, therefore, comprises CDR encoding sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably 100%, identical to the heavy chain CDR1, CDR2 and CDR3 encoding sequences and the light chain CDR1, CDR2 and CDR3 encoding sequences of antibody AT46, AT32, AT33, AT34, AT35, AT36, AT37, AT39, AT40, AT42, AT43, AT44, AT45, AT47, AT49, AT50 or AT51.

A nucleic acid sequence or functional equivalent thereof, according to the present disclosure, preferably encodes a region which has at least 70% sequence identity to a heavy chain and/or a light chain as depicted in table 1. Thus, a preferred nucleic acid sequence or a functional equivalent comprises a sequence which has at least 70% sequence identity to a sequence selected from the group consisting of SEQ ID NO:253-269 and/or a sequence which has at least 70% sequence identity to a sequence selected from the group consisting of SEQ ID NO:271-287. More preferably, a nucleic acid sequence or a functional equivalent, according to the disclosure, comprises a heavy chain encoding sequence as well as a light chain encoding sequence, which resemble the heavy and the light chain encoding sequences of the same antibody depicted in table 1. Thus, in a preferred embodiment, a nucleic acid or functional equivalent, according to the disclosure, comprises a heavy chain encoding sequence of antibody AT46, comprising the sequence of SEQ ID NO:253 and a light chain encoding sequence of antibody AT46, comprising the sequence of SEQ ID NO:271 or sequences that are at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, most preferably at least 99% identical thereto.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT32, comprising the sequence of SEQ ID NO:254 and the light chain encoding sequence of antibody AT32, comprising the sequence of SEQ ID NO:272.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT33, comprising the sequence of SEQ ID NO:255 and a light chain encoding sequence comprising the sequence of SEQ ID NO:273.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT34, comprising the sequence of SEQ ID NO:256 and a light chain encoding sequence of antibody AT34, comprising the sequence of SEQ ID NO:274.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT35, comprising the sequence of SEQ ID NO:257 and a light chain encoding sequence of antibody AT35, comprising the sequence of SEQ ID NO:275.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT36, comprising the sequence of SEQ ID NO:258 and a light chain encoding sequence of antibody AT36, comprising the sequence of SEQ ID NO:276.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT37, comprising the sequence of SEQ ID NO:259 and a light chain encoding sequence of antibody AT37, comprising the sequence of SEQ ID NO:277.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT39, comprising the sequence of SEQ ID NO:260 and a light chain encoding sequence of antibody AT39, comprising the sequence of SEQ ID NO:278.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT40, comprising the sequence of SEQ ID NO:261 and a light chain encoding sequence of antibody AT40, comprising the sequence of SEQ ID NO:279.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT42, comprising the sequence of SEQ ID NO:262 and a light chain encoding sequence of antibody AT42, comprising the sequence of SEQ ID NO:280.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT43, comprising the sequence of SEQ ID NO:263 and a light chain encoding sequence of antibody AT43, comprising the sequence of SEQ ID NO:281.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT44, comprising the sequence of SEQ ID NO:264 and a light chain encoding sequence of antibody AT44, comprising the sequence of SEQ ID NO:282.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT45, comprising the sequence of SEQ ID NO:265 and a light chain encoding sequence of antibody AT45, comprising the sequence of SEQ ID NO:283.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT47, comprising the sequence of SEQ ID NO:266 and a light chain encoding sequence of antibody AT47, comprising the sequence of SEQ ID NO:284.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT49, comprising the sequence of SEQ ID NO:267 and a light chain encoding sequence of antibody AT49, comprising the sequence of SEQ ID NO:285.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT50, comprising the sequence of SEQ ID NO:268 and a light chain encoding sequence of antibody AT50, comprising the sequence of SEQ ID NO:286.

In another embodiment, a nucleic acid or functional equivalent, according to the disclosure, comprises a sequence which has at least 70%, preferably at least 75%, more preferably at least 80%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, most preferably at least 100% sequence identity with the heavy chain encoding sequence of antibody AT51, comprising the sequence of SEQ ID NO:269 and a light chain encoding sequence of antibody AT51, comprising the sequence of SEQ ID NO:287.

The term "% sequence identity" is defined herein as the percentage of residues in a candidate amino acid of nucleic acid sequence that is identical with the residues in a reference sequence after aligning the two sequences and introducing gaps, if necessary, to achieve the maximum percent identity. Methods and computer programs for the alignment are well known in the art.

Further provided is a vector comprising a nucleic acid sequence or functional equivalent, according to the disclosure. As used herein "a vector comprising a nucleic acid sequence or functional equivalent, according to the disclosure," is also referred to as "a vector, according to the disclosure." Methods for constructing a vector with a nucleic acid sequence or functional equivalent, according to the disclosure, are well known in the art. Non-limiting examples of vectors suitable for generating a vector of the disclosure, are retroviral and lentiviral vectors. Such vector is suitable for a variety of applications. For instance, a vector of the disclosure comprising a therapeutically beneficial nucleic acid sequence is suitable for prophylactic or therapeutic applications. Administration of such vector to an individual, preferably a human, in need thereof results in expression of the prophylactic or therapeutic nucleic acid sequence in vivo. The vector can also be used in applications involving in vitro expression of a nucleic acid sequence of interest, for instance, for (commercial) production of antibodies or functional equivalents, according to the disclosure. Also provided is, therefore, an isolated or recombinant cell comprising a nucleic acid sequence or functional equivalent a vector, according to the disclosure.

A nucleic acid sequence or vector, according to the present disclosure, is particularly useful for generating antibodies or functional parts, or immunoglobulin chains or functional equivalents, which are specific for RSV G protein. This is, for instance, done by introducing such nucleic acid sequence or vector into a cell so that the cell's nucleic acid translation machinery will produce the encoded antibodies or functional parts, or immunoglobulin chains or functional equivalents. In one embodiment, a nucleic acid sequence or vector encoding a heavy and/or light chain, according to the disclosure, is expressed in so called producer cells, such as, for instance, cells of a Chinese hamster ovary (CHO), NSO (a mouse myeloma) or 293(T) cell line, some of which are adapted to commercial antibody production. Proliferation of the producer cells results in a producer cell line capable of producing RSV G-specific antibodies, according to the disclosure. Preferably, the producer cell line is suitable for producing antibodies for use in humans. Hence, the producer cell line is preferably free of pathogenic agents such as pathogenic micro-organisms. Most preferably, RSV G-specific antibodies consisting of human sequences are generated using at least one nucleic acid sequence or vector, according to the disclosure.

An isolated or recombinant antibody producing cell capable of producing an RSV G-specific antibody, according to the disclosure, is, therefore, also provided. An antibody producing cell is defined herein as a cell, which is capable of producing and/or secreting antibodies or functional equivalents thereof, and/or which is capable of developing into a cell, which is capable of producing and/or secreting antibodies or functional equivalents thereof. An antibody producing cell, according to the disclosure, is preferably a producer cell, which is adapted to commercial antibody production. Preferably, the producer cell is suitable for producing antibodies for use in humans. A method for producing an RSV G-specific antibody, according to the disclosure, is also provided, the method comprising providing a cell, preferably an antibody producing cell, with a nucleic acid sequence or functional equivalent, or a vector, according to the disclosure, and allowing the cell to translate the nucleic acid sequence or functional equivalent, or vector, thereby producing RSV G-specific antibodies, according to the disclosure. A method, according to the disclosure, preferably further comprises a step of harvesting, purifying and/or isolating RSV G-specific antibodies, according to the disclosure. Obtained RSV G-specific antibodies, according to the disclosure, are preferably used in human therapy, optionally after additional purifying, isolation or processing steps.

In one embodiment, an RSV G-specific antibody, according to the disclosure, is coupled to another moiety to form an antibody-drug conjugate. An RSV G-specific antibody, according to the disclosure, is, for instance, coupled to an antiviral agent, such as acyclovir, penciclovar, lamivudine, ribavirin, zanamivir, laninamivir, peramivir, idoxuridine, amantadine, remantidine, maxamine or thymalfasin. The term "antiviral agent," as used herein, refers to any substance that reduces or blocks the function, or growth, of a virus and/or causes destruction of a virus. In another embodiment, a moiety that is coupled to an RSV G-specific antibody, according to the disclosure, is an antimicrobial peptide. The term "antimicrobial peptide," as used herein, refers to small amphipathic peptides of variable length (typically 6 to 100 aminoacids), sequence and structure with activity against microorganisms such as, for instance, bacteria, protozoa, yeast, fungi and/or viruses. Antimicrobial peptides usually act through relatively non-specific mechanisms resulting in membranolytic activity but several antimicrobial peptides can also stimulate the innate immune response. In a preferred embodiment, the antimicrobial peptide has anti-viral activity. Non-limiting examples of suitable antimicrobial peptides are magainins, PGLa, cathelicidins (such as LL-37 and cathelicidin-related antimicrobial peptide (CRAMP)), alamethicin, mellitin and cecropin, hydramacin-1, pexiganan, MSI-78, MSI-843, MSI-594, polyphemusin, human antimicrobial peptide, defensins, protegrins and indolicidin. In yet another embodiment, a moiety that is coupled to an RSV G-specific antibody, according to the disclosure, is an immunomodulatory molecule such as an CD3 antibody. Such CD3 antibody is capable of binding T cells and, if coupled to an RSV G-specific antibody, according to the disclosure, targeting T cells to RSV infected cells.

The other moiety, for example, a cytotoxic agent, is preferably coupled to an RSV G-specific antibody, according to the disclosure, via a linker such as an acid-labile hydrazone linker, via a peptide linker like citruline-valine, through a thioether linkage, or by sortase catalized transamidation, which is described in detail in WO 2010/087994.

Sortase catalyzed transamidation involves engineering of a sortase recognition site (LPETGG) on the heavy chain of an antibody, preferably on the C-terminal part of the heavy chain, and on the moiety to be coupled to the antibody. The antibody and the moiety further typically contain a GGGGS sequence and a tag for purification purposes, such as a HIS tag. Subsequently, sortase mediated transamidation is performed followed by click chemistry linkage. In a sortase catalized transaminidation, "click chemistry linkage" typically involves chemical coupling of, for instance, an alkyne-containing reagent and, for instance, an azide-containing reagent, which are added by sortase through addition of glycines to the sortase motif on the heavy chain of the antibody and to a sortase motif on the moiety (such as a protein, peptide or antibody) to be coupled to the antibody. In one embodiment, the disclosure, therefore, provides an RSV G-specific antibody, according to the disclosure, wherein a sortase recognition site (LPETGG) is engineered on the heavy chain of the antibody, preferably on the C-terminal part of the heavy chain, the antibody further containing a GGGGS sequence and a purification tag, such as a HIS tag.

In another embodiment, an RSV G-specific antibody, according to the disclosure, is coupled to another moiety via a thioether linkage. In such case, one or more cysteines are preferably incorporated into an RSV G-specific antibody, according to the disclosure. Cysteines contain a thiol group and, therefore, incorporation of one or more cysteines into, or replacement of one or more amino acids by one or more cysteines of an RSV G-specific antibody, according to the disclosure, enable coupling of the RSV G-specific antibody to another moiety. The one or more cysteines are preferably introduced into an RSV G-specific antibody, according to the disclosure, at a position where it does not influence folding of the antibody, and does not alter antigen binding or effector function. The disclosure, therefore, also provides an RSV G-specific antibody, according to the disclosure, wherein at least one amino acid other than cysteine has been replaced by a cysteine.

As described herein before, an RSV G-specific antibody, according to the disclosure, preferably AT46, AT32, AT33 or AT35, and an RSV F-specific antibody, such as palivizumab, AM14, AM16, AM23, AM22 or D25 can be advantageously used in combination. Furthermore, it is also advantageous to combine an RSV G-specific antibody, according to the disclosure, with another RSV G-specific antibody, according to the disclosure, recognizing a different epitope or with a known RSV G-specific antibody recognizing a different epitope. In another embodiment, however, the disclosure provides an RSV bispecific antibody with specificity for both an RSV G protein and an RSV F protein, or with specificity to different epitopes within an RSV G protein. An "RSV bispecific antibody," as used herein, is defined as an antibody capable of simultaneously binding two different epitopes, which epitopes may be located within the same antigen, i.e., the RSV G protein, or located within different antigens, i.e., the RSV G and F protein, and is also referred to as "an RSV bispecific antibody, according to the disclosure." The term "RSV bispecific antibody" also encompasses functional parts of such RSV bispecific antibodies, which has retained its capability of binding a least two different epitopes simultaneously, such as bispecific single chain variable fragments (scFv), bispecific Fab fragments and a bispecific F(ab')2 fragment. Also provided is a pharmaceutical composition comprising an RSV bispecific antibody, according to the disclosure.

In one embodiment, a bispecific antibody, according to the disclosure, comprises two non-identical heavy chain-light chain combinations, thus having two antigen-binding regions, which recognize two different epitopes within the RSV G protein or which recognize one epitope in an RSV G protein and one epitope within an RSV F protein. For instance, in one embodiment, an RSV bispecific antibody comprises a heavy and light chain of an RSV G-specific antibody, according to the disclosure, as depicted in table 1, and a heavy and light chain of another RSV G-specific antibody, according to the disclosure, as depicted in table 1. In another embodiment, an RSV bispecific antibody comprises a heavy and light chain of an RSV G-specific antibody, according to the disclosure, as depicted in table 1, and a heavy and light chain of an RSV F-specific antibody. Bispecific single chain variable fragments (scFv), bispecific Fab fragments and a bispecific F(ab')2 fragment comprise, for instance, a scFv or Fab fragment of an RSV G-specific antibody, according to the disclosure, and a scFv or Fab fragment of another RSV G-specific antibody, according to the disclosure. Alternatively, bispecific single chain variable fragments (scFv), bispecific Fab fragments and a bispecific F(ab')2 fragment comprise a scFv or Fab fragment of an RSV G-specific antibody and a scFv or Fab fragment of an RSV F-specific antibody. In a preferred embodiment, an RSV bispecific antibody, according to the disclosure, comprises a heavy and light chain of antibody AT46, AT32, AT33 or AT35 as depicted in Table 1, or a scFv or Fab fragment thereof, and a heavy and light chain of an RSV F-specific antibody such as palivizumab, AM14, AM16, AM23, D25 (WO 2008/147196), or AM22 (WO 2011/043643) or a scFv or Fab fragment thereof. In another preferred embodiment, an RSV bispecific antibody, according to the disclosure, comprises two heavy and light chains of two different RSV G-specific antibodies, according to the disclosure, as depicted in Table 1, or a scFv or Fab fragment thereof, whereby the different RSV G-specific antibodies preferably form a combination depicted in Table 2 or 3.

In another embodiment, an RSV G-specific antibody, according to the disclosure, is coupled to an RSV F-specific antibody or another RSV G-specific antibody by sortase catalized transamidation, which is described herein before and in detail in WO 2010/087994. For this purpose, sortase catalized transamidation involves engineering of a sortase recognition site (LPETGG) on heavy chain of both antibodies to be coupled, preferably on the C-terminal part of the heavy chain. The antibodies further typically contain a GGGGS sequence and a purification tag, such as a HIS tag. Thus, if an RSV G-specific antibody, according to the disclosure, and an RSV F-specific antibody are coupled, both the RSV G-specific and the RSV F-specific antibodies are engineered, as described herein before and in detail in WO 2010/087994. If two RSV G-specific antibodies recognizing different epitopes in the G protein are coupled, both the RSV G-specific antibodies are engineered, as described herein before and in detail in WO 2010/087994. Subsequently, sortase mediated transamidation is preferably performed followed by click chemistry linkage to couple both antibodies via their heavy chains. As herein explained before, "click chemistry linkage" involves chemical coupling of, for instance, an alkyne-containing reagent and, for instance, an azide-containing reagent which are added by sortase through addition of glycines to the sortase motif on the heavy chain of a first antibody and to the heavy chain of a second antibody to be coupled to the first antibody. In a preferred embodiment, antibody AT46, AT32, AT33 or AT35, as depicted in Table 1, is coupled by sortase catalized transamidation to an RSV F-specific antibody, such as palivizumab, AM14, AM16, AM23, D25, or AM22. In another preferred embodiment, two RSV G-specific antibodies are coupled to each other by sortase catalized transamidation, whereby the RSV G-specific antibodies preferably form a combination depicted in Table 2 or 3.

RSV G-specific antibodies, according to the disclosure, are capable of counteracting Respiratory Syncytial Virus. RSV G-specific antibodies, according to the disclosure, are, therefore, particularly suitable for use as a medicine or prophylactic agent. Preferably, RSV G-specific antibodies, according to the disclosure, are used which consist of human sequences, in order to reduce the chance of adverse side effects when human individuals are treated. Such human sequences can be isolated from a human or synthetically or recombinantly produced based on the sequence of human antibodies. Provided is, therefore, an RSV G-specific antibody, according to the disclosure, or a composition comprising a combination of at least two RSV G-specific antibodies, according to the disclosure, for use as a medicament and/or prophylactic agent. Also provided is a nucleic acid sequence or functional equivalent thereof, according to the disclosure, or a vector, according to the disclosure, comprising such nucleic acid or functional equivalent for use as a medicament and/or prophylactic agent. When a nucleic acid or functional equivalent, according to the disclosure, is administered, it will be translated in situ by the host's machinery into an RSV G-specific antibody, according to the disclosure. Produced RSV G-specific antibodies, according to the disclosure, are capable of preventing and/or counteracting an RSV infection or RSV related disorder. RSV G-specific antibodies, according to the disclosure, are particularly suitable for use as a medicament because they are capable of counteracting RSV after an individual has been infected. On the contrary, palivizumab, the only anti-RSV antibody currently registered, is only useful for prophylactic treatment of premature infants and is thus not able to treat an established RSV infection. In a particularly preferred embodiment, the antibody comprises antibody AT46, or a functional part thereof. Provided is, thus, antibody AT46, comprising a heavy chain sequence of SEQ ID NO:109 and a light chain sequence of SEQ ID NO:127, for use as a medicament and/or prophylactic agent.

An RSV G-specific antibody, according to the disclosure, or a nucleic acid sequence or functional equivalent thereof, according to the disclosure, or a composition comprising a combination of at least two RSV G-specific antibodies, according to the disclosure, or an RSV bispecific antibody or a cell, according to the disclosure, is preferably used for at least in part treating and/or preventing an RSV infection and/or an RSV related disorder. As used herein, "at least in part treating an RSV infection" includes counteracting an RSV infection, alleviating symptoms resulting from an RSV infection and/or counteracting inflammation resulting from an RSV infection. Also provided is, therefore, an RSV G-specific antibody, according to the disclosure, or a nucleic acid sequence or functional equivalent thereof, according to the disclosure, or a composition comprising a combination of at least two RSV G-specific antibodies, according to the disclosure, or a vector, according to the disclosure, or a cell, according to the disclosure, or a RSV bispecific antibody, according to the disclosure, for use in a method of at least in part treating and/or preventing an RSV infection and/or an RSV related disorder. Examples of such RSV related disorders are bronchiolitis, pneumonia and tracheobronchitis resulting from an RSV infection. Further provided is a use of an RSV G-specific antibody, according to the disclosure, or a composition, according to the disclosure, or a vector, according to the disclosure, or a cell, according to the disclosure, or an RSV bispecific antibody, according to the disclosure, for the preparation of a medicament and/or prophylactic agent for at least in part treating and/or preventing an RSV infection and/or an RSV related disorder.

The disclosure further provides a method for at least in part treating and/or preventing an RSV infection and/or an RSV related disorder comprising administering to an individual, preferably a human, in need thereof, a therapeutically effective amount of an RSV G-specific antibody, according to the disclosure, and/or a nucleic acid sequence or functional equivalent thereof, according to the disclosure, and/or a composition comprising a combination of at least two RSV G-specific antibodies, according to the disclosure, and/or a vector, according to the disclosure, and/or a pharmaceutical composition, according to the disclosure, and/or a cell, according to the disclosure. In order to at least in part treat or prevent a disorder related to RSV, an RSV G-specific antibody, a nucleic acid sequence or functional equivalent thereof, an RSV bispecific antibody, a composition comprising a combination of at least two RSV G-specific antibodies, a vector, a pharmaceutical composition and/or a cell, according to the disclosure, is preferably administered to an individual before an RSV infection has taken place. Alternatively, an RSV G-specific antibody, a nucleic acid sequence or functional equivalent thereof, an RSV bispecific antibody, a composition comprising a combination of at least two RSV G-specific antibodies, a vector, a pharmaceutical composition and/or a cell, according to the disclosure, is administered when an individual is already infected. In that case, an RSV infection is counteracted, symptoms resulting from an RSV infection are alleviated and/or inflammation resulting from an RSV infection is counteracted. The antibody, nucleic acid sequence, functional equivalent, composition, vector, pharmaceutical composition and/or cell is preferably administered to individuals with an increased risk of complications, such as hospitalized individuals, for instance, infants, individuals with compromised immunity and/or elderly people. An RSV G-specific antibody, a nucleic acid sequence or functional equivalent thereof, a composition comprising a combination of at least two RSV G-specific antibodies, a vector, a pharmaceutical composition and/or a cell, according to the disclosure, is preferably administered via one or more injections. Typical doses of administration of an RSV G-specific antibody, according to the disclosure, or combinations of at least two thereof, or of an RSV bispecific antibody are between 0.1 and 10 mg per kg body weight. For prophylactic or therapeutic application RSV G-specific antibodies, according to the disclosure, or RSV bispecific antibodies, according to the disclosure, are preferably combined with a pharmaceutically acceptable carrier, diluent and/or excipient.

The disclosure further provides a pharmaceutical composition comprising an RSV G-specific antibody, according to the disclosure, or a composition comprising a combination of at least two RSV G-specific antibodies, according to the disclosure, and a pharmaceutical acceptable carrier, diluent and/or excipient. Also provided, is a pharmaceutical composition comprising an RSV bispecific antibody, according to the disclosure, and a pharmaceutical composition comprising an RSV G-specific antibody, according to the disclosure, coupled to an antiviral agent, antimicrobial peptide or immunomodulatory molecule, as described herein. Further provided, is a pharmaceutical composition comprising a nucleic acid sequence or functional equivalent, according to the disclosure, or a vector or a cell, according to the disclosure, comprising such nucleic acid or functional equivalent, and a pharmaceutical acceptable carrier, diluent and/or excipient. Examples of suitable carriers, for instance, comprise keyhole limpet haemocyanin (KLH), serum albumin (e.g., BSA or RSA) and ovalbumin. In one preferred embodiment, the suitable carrier comprises a solution, like, for example, saline. A pharmaceutical composition, according to the disclosure, is preferably suitable for human use. In one embodiment, the pharmaceutical composition further comprises at least one other RSV specific antibody, preferably an RSV F protein specific antibody such as palivizumab, D25, AM14, AM16, AM22 and/or AM23.

An RSV G-specific antibody, according to the present disclosure, is also particularly suitable for diagnostic uses. For instance, if an individual, preferably a human, is suspected of suffering from an RSV infection, a sample, such as a saliva, sputum, blood, or tissue sample, can be obtained from the individual. Subsequently, the sample can be tested for the presence of G protein of RSV, using an RSV G-specific antibody, according to the disclosure. Preferably, the sample is mixed with an RSV G-specific antibody, according to the disclosure, which will specifically bind to a G protein of RSV. The presence of G proteins of RSV in a sample is indicative for the presence of an RSV infection. G proteins of RSV and/or RSV comprising a G protein bound to an RSV G-protein, according to the disclosure, can be isolated from the sample and/or detected using any method known in the art, for example, but not limited to, isolation using magnetic beads, streptavidin-coated beads, or isolation through the use of secondary antibodies immobilized on a column. Alternatively, or additionally, an RSV G-specific antibody, according to the disclosure, is labeled in order to be able to detect the antibody, for instance, but not limited to, fluorescently labeled, or radioactively labeled. Alternatively, an RSV G-specific antibody, according to the disclosure, is detected using a labeled secondary antibody which is directed against the antibody. If binding of the antibody is detected, G protein of RSV is present, which is indicative for the presence of an RSV infection. The disclosure thus provides an RSV G-specific antibody, according to the disclosure, or a composition comprising a combination of at least two RSV G-specific antibodies, according to the disclosure, for use in diagnosis of an RSV infection.

The disclosure thus further provides a method for determining whether an RSV G protein is present in a sample comprising:

contacting the sample with an RSV G-specific antibody, according to the disclosure, or a composition comprising a combination of at least two RSV G-specific antibodies, according to the disclosure, allowing the antibody or an antibody component of the composition to bind the RSV G protein, if present, and determining whether RSV G protein is bound to the antibody, or to an antibody component of the composition, thereby determining whether an RSV G protein is present.

In a preferred embodiment, it is determined whether an individual is suffering from an RSV infection. Provided is, therefore, a method for determining whether an individual is suffering from an RSV infection comprising:

contacting a sample from the individual with an RSV G-specific antibody, according to the disclosure, or a composition comprising a combination of at least two RSV G-specific antibodies, according to the disclosure, allowing the antibody, or an antibody component of the composition to bind the RSV, if present, and determining whether RSV is bound to the antibody, or to an antibody component of the composition, thereby determining whether the individual is suffering from an RSV infection. Preferably, the individual is a human.

The disclosure is further explained in the following examples. These examples do not limit the scope of the disclosure, but merely serve to clarify the disclosure.

TABLE 1

Preferred RSV G-specific antibodies according to the disclosure.

| SEQ ID NO | Antibody | Identity | Sequence |
|---|---|---|---|
| 1 | AT46 | Heavy chain CDR1 | SRYVMS |
| 2 | AT32 | Heavy chain CDR1 | ELSIH |
| 3 | AT33 | Heavy chain CDR1 | SLAIS |
| 4 | AT34 | Heavy chain CDR1 | HYGMH |
| 5 | AT35 | Heavy chain CDR1 | TYWVS |
| 6 | AT36 | Heavy chain CDR1 | YNFIDHSVS |
| 7 | AT37 | Heavy chain CDR1 | SGGYSWN |
| 8 | AT39 | Heavy chain CDR1 | TYAVH |
| 9 | AT40 | Heavy chain CDR1 | DRHALH |
| 10 | AT42 | Heavy chain CDR1 | SNVYYWG |
| 11 | AT43 | Heavy chain CDR1 | NYGVS |
| 12 | AT44 | Heavy chain CDR1 | SGHYWA |
| 13 | AT45 | Heavy chain CDR1 | GHAIS |
| 14 | AT47 | Heavy chain CDR1 | NYGIC |
| 15 | AT49 | Heavy chain CDR1 | SLALN |
| 16 | AT50 | Heavy chain CDR1 | NYGIS |

TABLE 1-continued

Preferred RSV G-specific antibodies according to the disclosure.

| SEQ ID NO | Antibody | Identity | Sequence |
|---|---|---|---|
| 17 | AT51 | Heavy chain CDR1 | KYGIN |
| 18 | AM22 | Heavy chain CDR1 | KLSIH |
| 19 | AT46 | Heavy chain CDR2 | SITGSGATTYYADSVKGRFTIS |
| 20 | AT32 | Heavy chain CDR2 | GFEPEDGEYIYPQKSQG |
| 21 | AT33 | Heavy chain CDR2 | GIIPKFNRRDYAQKFQG |
| 22 | AT34 | Heavy chain CDR2 | VISYDGDKKYYADSVKG |
| 23 | AT35 | Heavy chain CDR2 | NINQDGSEKSYVDSVEG |
| 24 | AT36 | Heavy chain CDR2 | WISPYNHRTVYAEKFQG |
| 25 | AT37 | Heavy chain CDR2 | YIYQNDITYYNPSLMS |
| 26 | AT39 | Heavy chain CDR2 | WINPDNGDTKYSQRFQGRVVIT |
| 27 | AT40 | Heavy chain CDR2 | ILSYDGTTDYYADSVKG |
| 28 | AT42 | Heavy chain CDR2 | SIFHSGITHYTPSLNS |
| 29 | AT43 | Heavy chain CDR2 | WISTYNGNTWYSQKFQA |
| 30 | AT44 | Heavy chain CDR2 | GIHHSGSTYTNPPLKS |
| 31 | AT45 | Heavy chain CDR2 | GIIPGLGTTRYARKFQD |
| 32 | AT47 | Heavy chain CDR2 | WISGYNGNTYYAQNFQG |
| 33 | AT49 | Heavy chain CDR2 | GIIPLFGTQNYAQKFQG |
| 34 | AT50 | Heavy chain CDR2 | WISAYNGNTYYRQELQG |
| 35 | AT51 | Heavy chain CDR2 | WISAYNGNTYYAQKFQG |
| 36 | AM22 | Heavy chain CDR2 | GYEGEVDEIFYAQKFQ |
| 37 | AT46 | Heavy chain CDR3 | CGRAGQIFDD |
| 38 | AT32 | Heavy chain CDR3 | EARYCDNSRCSPNFDH |
| 39 | AT33 | Heavy chain CDR3 | DAEWAAGSDYFFDY |
| 40 | AT34 | Heavy chain CDR3 | QGAKGGHELSFYCALDV |
| 41 | AT35 | Heavy chain CDR3 | EVFVTQVEPAQWGF |
| 42 | AT36 | Heavy chain CDR3 | DRVQQGEGNFFDH |
| 43 | AT37 | Heavy chain CDR3 | GAYGSGTYYSADALDI |
| 44 | AT39 | Heavy chain CDR3 | GRIFDI |
| 45 | AT40 | Heavy chain CDR3 | GRALDDFADYGGYYFDY |
| 46 | AT42 | Heavy chain CDR3 | HWAGLYFDS |
| 47 | AT43 | Heavy chain CDR3 | HGSGNYYGEANYFDH |
| 48 | AT44 | Heavy chain CDR3 | DLYDLSTGPFWFDP |
| 49 | AT45 | Heavy chain CDR3 | VAGGYFDSATRG |
| 50 | AT47 | Heavy chain CDR3 | GFHYHSADQRIFDP |
| 51 | AT49 | Heavy chain CDR3 | FLWFGDQTSDDGFDV |
| 52 | AT50 | Heavy chain CDR3 | GGAQEMVRIHYYYYGMDV |
| 53 | AT51 | Heavy chain CDR3 | PATSYDDLRSGYLNYCDY |
| 54 | AM22 | Heavy chain CDR3 | LGVTVTEAGLGIDDY |

TABLE 1-continued

Preferred RSV G-specific antibodies according to the disclosure.

| SEQ ID NO | Antibody | Identity | Sequence |
|---|---|---|---|
| 55 | AT46 | Light chain CDR1 | TLSSGHRNYAIA |
| 56 | AT32 | Light chain CDR1 | KSSQSVLYDSNNKNYLA |
| 57 | AT33 | Light chain CDR1 | SADAFSDQYAY |
| 58 | AT34 | Light chain CDR1 | RASQGIGSWLA |
| 59 | AT35 | Light chain CDR1 | RASQSIDNYLN |
| 60 | AT36 | Light chain CDR1 | KSSQSLLHSSNNKIYLA |
| 61 | AT37 | Light chain CDR1 | RASQSVSASNLA |
| 62 | AT39 | Light chain CDR1 | QASQDISNFLN |
| 63 | AT40 | Light chain CDR1 | RASQGISTWLA |
| 64 | AT42 | Light chain CDR1 | RASQTVSSSHLA |
| 65 | AT43 | Light chain CDR1 | RASESVSRNYLA |
| 66 | AT44 | Light chain CDR1 | RASQSVSTKVV |
| 67 | AT45 | Light chain CDR1 | RSSQSLLHSNGYNYLD |
| 68 | AT47 | Light chain CDR1 | RASESISTWLA |
| 69 | AT49 | Light chain CDR1 | RSSQSLLHGNGYKYLH |
| 70 | AT50 | Light chain CDR1 | RASQVISSYLA |
| 71 | AT51 | Light chain CDR1 | RASQGITSYLA |
| 72 | AM22 | Light chain CDR1 | RASQIVSRNHLA |
| 73 | AT46 | Light chain CDR2 | TNGSHYPGD |
| 74 | AT32 | Light chain CDR2 | WASTRES |
| 75 | AT33 | Light chain CDR2 | KDTERPS |
| 76 | AT34 | Light chain CDR2 | NASGLES |
| 77 | AT35 | Light chain CDR2 | LASTLQS |
| 78 | AT36 | Light chain CDR2 | WASTRES |
| 79 | AT37 | Light chain CDR2 | GASRTAT |
| 80 | AT39 | Light chain CDR2 | DASKLQT |
| 81 | AT40 | Light chain CDR2 | SASRLQS |
| 82 | AT42 | Light chain CDR2 | GSSSRAT |
| 83 | AT43 | Light chain CDR2 | GASSRAI |
| 84 | AT44 | Light chain CDR2 | GASTRAT |
| 85 | AT45 | Light chain CDR2 | GSNRAP |
| 86 | AT47 | Light chain CDR2 | KASSLES |
| 87 | AT49 | Light chain CDR2 | LGSNRAS |
| 88 | AT50 | Light chain CDR2 | GASTLQT |
| 89 | AT51 | Light chain CDR2 | AASTLQS |
| 90 | AM22 | Light chain CDR2 | GASSRAT |
| 91 | AT46 | Light chain CDR3 | QTWGAGI |

TABLE 1-continued

Preferred RSV G-specific antibodies according to the disclosure.

| SEQ ID NO | Antibody | Identity | Sequence |
|---|---|---|---|
| 92 | AT32 | Light chain CDR3 | QQYYDPL |
| 93 | AT33 | Light chain CDR3 | QSTDTSGPL |
| 94 | AT34 | Light chain CDR3 | QQYNSHT |
| 95 | AT35 | Light chain CDR3 | QQSHSSP |
| 96 | AT36 | Light chain CDR3 | QQYYTTHP |
| 97 | AT37 | Light chain CDR3 | QQYGSSP |
| 98 | AT39 | Light chain CDR3 | QKFDNLL |
| 99 | AT40 | Light chain CDR3 | QQANTFP |
| 100 | AT42 | Light chain CDR3 | QYYGDSP |
| 101 | AT43 | Light chain CDR3 | QQYTIFP |
| 102 | AT44 | Light chain CDR3 | QQYNKWP |
| 103 | AT45 | Light chain CDR3 | MQALQTP |
| 104 | AT47 | Light chain CDR3 | QQYKSYP |
| 105 | AT49 | Light chain CDR3 | MQALQSP |
| 106 | AT50 | Light chain CDR3 | QQLNTYP |
| 107 | AT51 | Light chain CDR3 | QQFHTYP |
| 108 | AM22 | Light chain CDR3 | LSSDSSI |
| 109 | AT46 | Heavy chain | EVQLVESGGGLVQPGGSLRLSCAASGFTFSRYVMSWVRQAPGRGLEWVSSITGSGA TTYYADSVKGRFTISRDNSKNTVYLQMNRLRAEDTAIYYCANCGRAGQIFDDWGQ GTLVTVSS |
| 110 | AT32 | Heavy chain | QVQLVQSGAEMKKPGASVKVSCQVAGYTLTELSIHWVRQTPGNGLEWMGGFEPE DGEYIYPQKSQGRVTMTEDTSTGTAYMELRSLRSDDTAVYYCAAEARYCDNSRCS PNFDHWGQGTLVAVSS |
| 111 | AT33 | Heavy chain | QVQLVQSGAEVKKPGSSVKVSCKASGDSFNSLAISWVRQAPGQGLEWMGGIIPKFN RRDYAQKFQGRVTITADDSASTAYIELSSLTSDDTALYYCARDAEWAAGSDYFFDY WGQGTLVIVSS |
| 112 | AT34 | Heavy chain | QVQLMESGGGVVQPGKSLRLSCAASGFTFSHYGMHWVRQAPGKGLEWVAVISYD GDKKYYADSVKGRFTISRDNSKNTLHLHMNSLRHEDTAVYFCASQGAKGGHELSF YCALDVWGQGTTAVSS |
| 113 | AT35 | Heavy chain | EVQLVESGGGLVQPGGSLRLSCAASGFTFSTYWVSWVRQTPGKGLEWVARFTISNI NQDGSEKSYVDSVEGRDNAKNSLYLQMNSLRADDTAVYYCAREVFVTQVEPAQW GFWGQGTPVIVSS |
| 114 | AT36 | Heavy chain | QVQVVQSGAEVKKPGASVKVSCKTSGYNFIDHSVSWVRQAPGQGLEWMGWISPY NHRTVYAEKFQGRVTMTTDTSTRTVSMELRRLTSDDTAVYFCARDRVQQGEGNFF DHWGQGTPVTVTSA |
| 115 | AT37 | Heavy chain | QLQLQESGSRLVKPSQTLSLTCGVSGGSISSGGYSWNWIRQPPGKGLEWVGYIYQN DITYYNPSLMSRVTISADTSKNQFSLKLSSVTAADTAVYYCARGAYGSGTYYSADA LDIWGQGTMVTVSS |
| 116 | AT39 | Heavy chain | QVQLVQSGPEVKKPGASVRLSCTASGNTFRTYAVHWVRQASGQRLEWMGWINPD NGDTKYSQRFQGRVVITRDTSARIIYLDLSSLTSEDTAVFYCFSGRIFDIWGQGTTITV SS |
| 117 | AT40 | Heavy chain | QVQLVESGGGVVQPGMSHRLSCAASTLIFDRHALHWVRQAPGAGLEWVAILSYDG TTDYYADSVKGRFTVSRDTSKNTVFLQMNGLRPQDTAVYYCARGRALDDFADYG GYYFDYWGQGILVTVSS |
| 118 | AT42 | Heavy chain | QVQLQESGPGLVQPSETLSLTCTVSGDSITSNVYYWGWIRQPPGKGLEWIGSIFHSGI THYTPSLNSRVTISVDTSKNQFSLRLSSATAADTAVYYCARHWAGLYFDSWGQGAL VAVSS |

TABLE 1-continued

Preferred RSV G-specific antibodies according to the disclosure.

| SEQ ID NO | Antibody | Identity | Sequence |
|---|---|---|---|
| 119 | AT43 | Heavy chain | QVQVVQSGPEVKKPGASVRVSCKASGYTFTNYGVSWVRQAPGQGLEWMGWISTY NGNTWYSQKFQARVTMTTDTSTSTAYMEVRSLRSDDTAIYYCACHGSGNYYGEAN YFDHWGQGTLVTVSS |
| 120 | AT44 | Heavy chain | QVQLQASGPGLVKPSETLSLTCNVSGYSVSSGHYWAWVRQSPGKGLEWIGGIHHSG STYTNPPLKSRVSISIDTSKNQFSLRLTSVTAADTAVYFCARDLYDLSTGPFWFDPW GQGTLVTVSS |
| 121 | AT45 | Heavy chain | QVHLVQSGAEVKKPGSSVKVSCKASGGTFNGHAISWIRQAPGQGLEWKGGIIPGLG TTRYARKFQDRVTITADESTRTAYMELSSLRSEDTAVYYCARVAGGYFDSATRGW GQGTLVTVSS |
| 122 | AT47 | Heavy chain | QVQLVQSGGEVKKPGASVKVSCKASGYTFTNYGICWVRQAPGQGLEWMGWISGY NGNTYYAQNFQGRVTMTTDTSTSTAYMELRSLRSDDTAVYYCARGFHYHSADQRI FDPWGQGTLVTVSS |
| 123 | AT49 | Heavy chain | QVLLVQSGAEIKKPGSSVKISCKASGGTFSSLALNWVRQAPGQGLQWMGGIIPLFGT QNYAQKFQGRVTITADESTSTAYMELSGLRPEDTAVYYCALFLWFGDQTSDDGFD VWGQGTVVTVSS |
| 124 | AT50 | Heavy chain | QVQLVQSGTEVKKPGASVKVSCKASGYTFSNYGISWVRQAPGQGLEWMGWISAY NGNTYYRQELQGRVTMTTDTSTSTAYMELRSLRSDDTAVYYCARGGAQEMVRIHY YYYGMDVWGQGTTVTVSS |
| 125 | AT51 | Heavy chain | QVQLVQSGAEVKKPGASMTVSCKASGYTFSKYGINWVRQAPGQGLEWLGWISAY NGNTYYAQKFQGRVTMTTDTATSTAYMDVRNLRSDDTAMYYCARPATSYDDLRS GYLNYCDYWGQGTLVTVSS |
| 126 | AM22 | Heavy chain | QVQLVQSGAEVKKPGATVKVSCKISGHTLIKLSIHWVRQAPGKGLEWMGGYEGEV DEIFYAQKFQHRLTVIADTATDTVYMELGRLTSDDTAVYFCGTLGVTVTEAGLGID DYWGQGTLVTVSS |
| 127 | AT46 | Light chain | QPVLTQSPSASASLGASVKLTCTLSSGHRNYAIAWHQQRPEKGPRYLMKIYTNGSH YPGDGTPDRFSGSSSGAERYLTISSLQSEDEADYYCQTWGAGIWVFGGGTKLTVLG QPK |
| 128 | AT32 | Light chain | DIVMTQSPDSLAVSLGERATFSCKSSQSVLYDSNNKNYLAWYQQRPGQPPKLLIYW ASTRESGVPDRFSGSGSGTDFTLTISSLQPEDVAVYYCQQYYDPLITFGQGTRLEIKR TV |
| 129 | AT33 | Light chain | SYELTQPPSVSVSPGQTARITCSADAFSDQYAYWYQQKPGQAPVLVIYKDTERPSGI PERISGSSSGTTATLSISGVQAEDEADYYCQSTDTSGPLFGGGTKLTLLGQPK |
| 130 | AT34 | Light chain | DIQMTQSPSTLSASVGDRVTITCRASQGIGSWLAWYQQKPGKAPKLLIYNASGLESG VPSGFSGSGSGTEFTLTISSLQPDDSATYYCQQYNSHTWTFGQGTKVEFKRTV |
| 131 | AT35 | Light chain | AIQMTQSPSSLSASVGDRVTISCRASQSIDNYLNWYQQKPGKAPKLLLFLASTLQSG VPSRFTGSGSGTDFTLTISSLQPEDFATYYCQQSHSSPYSFGQGTKLEIKRTV |
| 132 | AT36 | Light chain | DIVMTQSPDSLAVSLGERATINCKSSQSLLHSSNNKIYLAWYQQKPGQPPKLLLYW ASTRESGVPDRFTGSGSGTDFTLTINSLQAEDVAVYYCQQYYTTHPFTGQGTRLEIK RTV |
| 133 | AT37 | Light chain | KIVLTQSPGTLSLSPGERATLSCRASQSVSASNLAWYQQKPGQAPRLLIYGIPDRFSG SGSGTDFTLSISRLEPEDFAVYYCGASRTATQQYGSSPLTFGGGTKVEIKRTV |
| 134 | AT39 | Light chain | DIQMTQSPSSLSASVGDRVTITCQASQDISNFLNWYQQKPGQAPKLLIYDASKLQTG VPSRFSGSGSETDFTFTISSLQPEDVATYYCQKFDNLLLTFGGGTKVELKRTV |
| 135 | AT40 | Light chain | DIQMTQSPSSVSASVGDKVTITCRASQGISTWLAWYQQKPGKAPALLIYSASRLQSG VPSRFSGSGSGTDFTLTISSLQPEDYATYYCQQANTFPFTFGPGTKVDIKRTV |
| 136 | AT42 | Light chain | EIVLTQSPGTLSLSPGERATLSCRASQTVSSSHLAWYQQKPGQAPRLLIHGSSSRATG IPERFSGSGSGPDFTLTISRLKPEDFAVYYCQYYGDSPGSFGEGTKVEIKRTV |
| 137 | AT43 | Light chain | DIVLTQSPGTLSLSPGEGATLSCRASESVSRNYLAWYQQKPGQAPRLLIYGASSRAIG IPDRFSGSGSGTDFTLTISRLEPEDFAVYCCQQYTIFPLTFGGGTKVEIKRTV |
| 138 | AT44 | Light chain | EIVMTQSPATLSVSPGERVTLSCRASQSVSTKVVWYQQKFGQAPRLLIYGASTRATG IPVRFSGSGSGTEFTLTISSLQSEDLAVYFCQQYNKWPMYTFGQGTKLEIKRTV |
| 139 | AT45 | Light chain | DIVMTQSPLSLPVTPGESASISCRSSQSLLHSNGYNYLDWYLQKPGQSPQLLIYLGSN RAPGVPDRFSGSGSGTDFTLKISRVEAEDVGVYYCMQALQTPTFGQGTKVEIKRTV |

TABLE 1-continued

Preferred RSV G-specific antibodies according to the disclosure.

| SEQ ID NO | Antibody | Identity | Sequence |
|---|---|---|---|
| 140 | AT47 | Light chain | DIQMTQSPSTLSASVGDRVTITCRASESISTWLAWYQQKPGKAPNLLIYKASSLESG VPSRFSGSGSGTEFTLAISSLQPDDFATYYCQQYKSYPYTFGQGTKLELKRTV |
| 141 | AT49 | Light chain | DIVMTQSPLSLTVTPGEPASISCRSSQSLLHGNGYKYLHWYLQKPGQSPQLLIYLGSN RASGVPARFSGSGSDTDFTLKISTVETEDVGVYYCMQALQSPTFGQGTKVEIKRTV |
| 142 | AT50 | Light chain | DIQLTQSPSFLSASVGDRVTITCRASQVISSYLAWYQQTPGRAPKLLIYGASTLQTGV PSRFSGSGSGTEFTLTISSLQPEDFATYFCQQLNTYPLTFGPGTKVEIKRTV |
| 143 | AT51 | Light chain | DIQLTQSPSFLSASVGDRVTITCRASQGITSYLAWYQQKPGRAPKLLIYAASTLQSGV ASRFSGSGSGTEFTLTISSLQPEDFATYYCQQFHTYPLTFGGGTKVEIKRTV |
| 144 | AM22 | Light chain | EIVLTQSPGTLSLSPGERATLSCRASQIVSRNHLAWYQQKPGQAPRLLIFGASSRATG IPVRFSGSGSGTDFTLTINGLAPEDFAVYYCLSSDSSIFTFGPGTKVDFK |
| 145 | AT46 | Heavy chain CDR1 | agt aga tat gtc atg agt |
| 146 | AT32 | Heavy chain CDR1 | gaa tta tee ata cac |
| 147 | AT33 | Heavy chain CDR1 | agt ctt gcc atc agt |
| 148 | AT34 | Heavy chain CDR1 | cat tat ggc atg cac |
| 149 | AT35 | Heavy chain CDR1 | acc tat tgg gtg agc |
| 150 | AT36 | Heavy chain CDR1 | tac aac ttt atc gac cat agt gtc agc |
| 151 | AT37 | Heavy chain CDR1 | agt ggt ggt tac tee tgg aac |
| 152 | AT39 | Heavy chain CDR1 | acc tat gct gta cat |
| 153 | AT40 | Heavy chain CDR1 | gat aga cat gct ctc cac |
| 154 | AT42 | Heavy chain CDR1 | agt aat gtt tac tac tgg ggc |
| 155 | AT43 | Heavy chain CDR1 | aac tat ggt gtc agc |
| 156 | AT44 | Heavy chain CDR1 | agc ggt cac tac tgg gcc |
| 157 | AT45 | Heavy chain CDR1 | ggc cat gct atc agc |
| 158 | AT47 | Heavy chain CDR1 | aac tac ggt atc tgt |
| 159 | AT49 | Heavy chain CDR1 | agc ctt gct ctc aat |
| 160 | AT50 | Heavy chain CDR1 | aac tat ggt atc agt |
| 161 | AT51 | Heavy chain CDR1 | aag tat ggc atc aac |
| 162 | AM22 | Heavy chain CDR1 | aaa tta tcc att cac |
| 163 | AT46 | Heavy chain CDR2 | agc att act gga agt ggt gct acg aca tac tat gca gac tcc gtg aag ggc cgc ttc acc atc tcc |
| 164 | AT32 | Heavy chain CDR2 | ggt ttt gag cct gag gat ggt gag tac atc tac cca cag aaa tcc cag ggc |
| 165 | AT33 | Heavy chain CDR2 | ggg atc atc cct aag ttc aat aga aga gac tac gca cag aag ttt cag ggc |
| 166 | AT34 | Heavy chain CDR2 | gtc ata tcc tat gat ggc gat aaa aaa tat tat gca gac tca gtg aag ggc |
| 167 | AT35 | Heavy chain CDR2 | aac att aac caa gat gga agt gag aag tcc tat gtg gac tct gtg gag ggc cga ttc acc atc tcc |
| 168 | AT36 | Heavy chain CDR2 | tgg atc agc cct tac aac cac aga aca gta tat gca gag aag ttc cag ggc |
| 169 | AT37 | Heavy chain CDR2 | tac atc tat cag aat gac atc acc tac tac aac ccg tcc ctc atg agt |
| 170 | AT39 | Heavy chain CDR2 | tgg atc aac cct gac aat ggt gac aca aaa tat tca cag agg ttc cag ggt aga gtc gtc att acc |

TABLE 1-continued

Preferred RSV G-specific antibodies according to the disclosure.

| SEQ ID NO | Antibody Identity | Sequence |
|---|---|---|
| 171 | AT40 | Heavy chain CDR2 att ctc tct tat gat ggg acc aca gac tac tac gca gac tcc gtg aag ggc |
| 172 | AT42 | Heavy chain CDR2 agt atc ttt cat agt ggg atc acc cac tat acc ccg tcc ctc aat agt |
| 173 | AT43 | Heavy chain CDR2 tgg atc agc act tac aat ggt aac aca tgg tat tca cag aag ttc cag gcc |
| 174 | AT44 | Heavy chain CDR2 ggt atc cat cat agt ggg agt acc tac acc aat ccg ccc ctc aag agc |
| 175 | AT45 | Heavy chain CDR2 ggg atc atc cct ggc ctt ggt aca aca agg tac gca cgg aag ttc cag gac |
| 176 | AT47 | Heavy chain CDR2 tgg atc agc ggt tac aat ggt aac aca tac tat gca cag aac ttc cag ggc |
| 177 | AT49 | Heavy chain CDR2 ggg atc atc cct ctc ttt ggc act caa aac tac gca cag aag ttc cag ggc |
| 178 | AT50 | Heavy chain CDR2 tgg atc agc gct tac aat ggt aac aca tac tat aga cag gag ctc cag ggc |
| 179 | AT51 | Heavy chain CDR2 tgg atc agc gca tac aat ggc aac aca tac tat gca cag aag ttc cag ggc |
| 180 | AM22 | Heavy chain CDR2 ggt tat gag ggt gag gtc gat gag att ttc tac gca cag aag ttc cag cac |
| 181 | AT46 | Heavy chain CDR3 tgt ggt agg gcg ggc caa att ttt gac gac |
| 182 | AT32 | Heavy chain CDR3 gag gca aga tat tgt gat aac agc aga tgt tcc cct aac ttt gac cac |
| 183 | AT33 | Heavy chain CDR3 gac gcc gag tgg gca gct ggc tcg gat tac ttc ttt gac tac |
| 184 | AT34 | Heavy chain CDR3 cag ggg gca aag ggc ggt cac gaa ctt tct ttc tac tgt gct ttg gac gtc |
| 185 | AT35 | Heavy chain CDR3 gaa gtc ttc gtg act cag gtg gag ccc gcg cag tgg ggc ttc |
| 186 | AT36 | Heavy chain CDR3 gat cga gta caa cag ggc gag gga aac ttc ttt gac cac |
| 187 | AT37 | Heavy chain CDR3 ggg gcc tat ggt tcg gga act tat tat tcc gct gat gct ctt gat ata |
| 188 | AT39 | Heavy chain CDR3 ggg aga att ttt gat ata |
| 189 | AT40 | Heavy chain CDR3 gga agg gcc cta gat gac ttc gct gac tac ggg gga tac tac ttt gac tac |
| 190 | AT42 | Heavy chain CDR3 cat tgg gct ggc ctc tac ttt gac tct |
| 191 | AT43 | Heavy chain CDR3 cac ggg agt ggc aat tac tac ggc gaa gcg aac tac ttt gac cac |
| 192 | AT44 | Heavy chain CDR3 gat ctg tac gat ctt tcg acg ggg cct ttt tgg ttc gac ccc |
| 193 | AT45 | Heavy chain CDR3 gtg gcc ggg gga tac ttc gat agt gct act cga ggc |
| 194 | AT47 | Heavy chain CDR3 ggg ttt cac tat cat agt gct gat cag aga ata ttc gac ccc |
| 195 | AT49 | Heavy chain CDR3 ttt ctt tgg ttc ggg gac caa acg agt gat gat ggt ttt gat gtc |
| 196 | AT50 | Heavy chain CDR3 ggg ggt gcc caa gag atg gtt aga ata cac tac tac tac gga atg gac gtc |
| 197 | AT51 | Heavy chain CDR3 ccc gca acc tca tat gac gat ctt cgg agt ggt tat ttg aac tac tgt gac tac |

TABLE 1-continued

Preferred RSV G-specific antibodies according to the disclosure.

| SEQ ID NO | Antibody | Identity | Sequence |
|---|---|---|---|
| 198 | AM22 | Heavy chain CDR3 | cta ggt gtg aca gtg act gag gct gga ctg ggg atc gat gac tac |
| 199 | AT46 | Light chain CDR1 | act ctg agc agt ggg cac agg aac tac gcc atc gca |
| 200 | AT32 | Light chain CDR1 | aag tcc agc cag agt gtt tta tac gac tcc aac aat aag aac tac tta gct |
| 201 | AT33 | Light chain CDR1 | tct gca gat gca ttt tca gac caa tat gct tat |
| 202 | AT34 | Light chain CDR1 | cgg gcc agt cag ggt att ggt agt tgg ttg gcc |
| 203 | AT35 | Light chain CDR1 | cgg gca agt cag agc att gac aac tat tta aat |
| 204 | AT36 | Light chain CDR1 | aag tcc agc cag agt ctt tta cac agc tcc aac aat aag atc tac tta gct |
| 205 | AT37 | Light chain CDR1 | agg gcc agt cag agt gtt agc gcc agc aac tta gcc |
| 206 | AT39 | Light chain CDR1 | cag gcg agt cag gac att agc aac ttt tta aat |
| 207 | AT40 | Light chain CDR1 | cgg gcg agt cag ggt att agt acc tgg tta gcc |
| 208 | AT42 | Light chain CDR1 | agg gcc agt cag act gta agc agc agc cac tta gcc |
| 209 | AT43 | Light chain CDR1 | agg gcc agt gag agt gtt agc cgc aac tac tta gcc |
| 210 | AT44 | Light chain CDR1 | agg gcc agt cag agt gtc agc acc aag gta gtc |
| 211 | AT45 | Light chain CDR1 | agg tct agt cag agc ctc ctg cat agt aat gga tac aac tat ttg gat |
| 212 | AT47 | Light chain CDR1 | cgg gcc agt gag agt att agt acc tgg ttg gcc |
| 213 | AT49 | Light chain CDR1 | agg tct agt cag agc ctc ctg cat ggt aat gga tac aaa tat ctg cac |
| 214 | AT50 | Light chain CDR1 | cgg gca agc cag gtc att agc agt tat tta gcc |
| 215 | AT51 | Light chain CDR1 | cgg gca agt cag ggc att acc agt tat tta gcc |
| 216 | AM22 | Light chain CDR1 | agg gcc agt cag att gtt agc agg aac cac tta gcc |
| 217 | AT46 | Light chain CDR2 | act aat ggc agc cac tac ccg ggg gac |
| 218 | AT32 | Light chain CDR2 | tgg gcg tct acc cgg gaa tcc |
| 219 | AT33 | Light chain CDR2 | aaa gac act gag agg ccc tca |
| 220 | AT34 | Light chain CDR2 | aac gcg tct ggc tta gaa agt |
| 221 | AT35 | Light chain CDR2 | ctt gcg tcc act ttg caa agt |
| 222 | AT36 | Light chain CDR2 | tgg gca tct acc cgg gag tcc |
| 223 | AT37 | Light chain CDR2 | ggt gca tcc agg acg gcc act |
| 224 | AT39 | Light chain CDR2 | gat gcg tcc aaa ttg caa aca |
| 225 | AT40 | Light chain CDR2 | tct gca tcc aga ttg cag agt |
| 226 | AT42 | Light chain CDR2 | ggt tca tct agc agg gcc aca |
| 227 | AT43 | Light chain CDR2 | ggt gca tcc agc agg gcc att |
| 228 | AT44 | Light chain CDR2 | ggt gca tcc acc agg gcc act |
| 229 | AT45 | Light chain CDR2 | ggt tct aat cgg gcc ccc |
| 230 | AT47 | Light chain CDR2 | aag gcg tct agt tta gaa agt |
| 231 | AT49 | Light chain CDR2 | ttg ggt tct aat cgg gcc tcc |
| 232 | AT50 | Light chain CDR2 | ggt gca tcc acg tta caa act |

TABLE 1-continued

Preferred RSV G-specific antibodies according to the disclosure.

| SEQ ID NO | Antibody | Identity | Sequence |
|---|---|---|---|
| 233 | AT51 | Light chain CDR2 | gct gca tcc act ttg caa agt |
| 234 | AM22 | Light chain CDR2 | ggt gcg tcc agt cgg gcc act |
| 235 | AT46 | Light chain CDR3 | cag acc tgg ggc gct ggc att |
| 236 | AT32 | Light chain CDR3 | caa caa tat tat gat cct ctc |
| 237 | AT33 | Light chain CDR3 | caa tca aca gac acc agt ggt cct tta |
| 238 | AT34 | Light chain CDR3 | caa caa tac aat agt cac acg |
| 239 | AT35 | Light chain CDR3 | caa cag agc cac tct tcc ccc |
| 240 | AT36 | Light chain CDR3 | cag caa tat tat act act cat ccc |
| 241 | AT37 | Light chain CDR3 | caa cag tat ggt agc tca ccg |
| 242 | AT39 | Light chain CDR3 | caa aag ttt gat aat ctc ctt |
| 243 | AT40 | Light chain CDR3 | caa cag gct aac act ttc ccc |
| 244 | AT42 | Light chain CDR3 | cag tac tat ggt gac tca ccc |
| 245 | AT43 | Light chain CDR3 | tgt cag cag tat act atc ttc cct |
| 246 | AT44 | Light chain CDR3 | cag cag tat aat aag tgg ccc |
| 247 | AT45 | Light chain CDR3 | atg caa gct cta caa act cct |
| 248 | AT47 | Light chain CDR3 | caa cag tat aaa agt tac ccg |
| 249 | AT49 | Light chain CDR3 | atg caa gct cta caa agt ccg |
| 250 | AT50 | Light chain CDR3 | caa cag ctt aat act tac ccc |
| 251 | AT51 | Light chain CDR3 | caa cag ttt cat act tac ccg |
| 252 | AM22 | Light chain CDR3 | ctg tcc tct gat tcc tcc ata |
| 253 | AT46 | Heavy chain | gag gtg cag ctg gtg gag tct ggg gga ggc ttg gta cag cct ggg ggg tcc ctg cga ctc tcc tgt gca gcc tct gga ttc acc ttt agt aga tat gtc atg agt tgg gtc cgc cag gct cca ggg agg ggc ctg gag tgg gtc tca agc att act gga agt ggt gct acg aca tac tat gca gac tcc gtg aag ggc cgc ttc acc atc tcc aga gac aat tcc aag aac acg gtg tat ctg caa atg aac agg ctg aga gcc gag gac acg gcc ata tat tac tgt gcg aat tgt ggt agg cgc ggc caa att ttt gac gac tgg ggc cag gga acc ctg gtc acc gtc tcc tca |
| 254 | AT32 | Heavy chain | cag gtc cag ctg gta caa tct ggg gct gag atg aag aag cct ggg gcc tca gtg aag gtc tcc tgc agg gtt gcc gga tac acc ctc act gaa tta tcc ata cac tgg gtg cga cag act cct gga aac ggg ctt gag tgg atg gga ggt ttt gag cct gag gat ggt gag tac atc tac cca cag aaa tcc agg ggc aga gtc acc atg acc gag gac aca tct aca ggc aca gcc tac atg gaa ctg agg agc ctg aga tct gac gac acg gcc gtg tat tac tgt gca gcc gag gca aga tat tgt gat aac agc aga tgt tcc cct aac ttt gac ac tgg ggc cag gga acc ctg gtc gcc gtc tcc tca |
| 255 | AT33 | Heavy chain | cag gtg cag ttg gtg cag tct ggg gct gag gtg aag aag cct ggg tcc tcg gtg aag gtc tcc tgc aag gct tct gga ttc acc ttc aac agt ctt gcc atc agt tgg gtg cga cag gcc cct gga caa gga ctc gag tgg atg gga ggg atc atc cct aag ttc aat aga aga gac tac gca cag aag ttt cag ggc aga gtc acg att acc gcg gac gac tcc gcg agc aca gcc tac ata gag ttg agc agc ctg aca tct gac gac aca gcc ctg tat tac tgt gcg aga gac gcc gag tgg gca gct ggc tcg gat tac ttc ttt gac tac tgg ggc cag gga acc ctg gtc atc gtc tcc tca |
| 256 | AT34 | Heavy chain | cag gtg caa ttg atg gag tct ggg gga ggc gtg gtc cag cct ggg aag tcc ctg aga ctc tcc tgt gca gcc tct gga ttc acc ttc agt cat tat ggc atg cac tgg gtc cgc cag gct cca ggc aag ggg ctg gag tgg gtg gca gtc ata tcc tat gat ggc gat aaa aaa tat tat gca gac tca gtg aag ggc cga ttc acc atc tcc aga gac aat tcc |

TABLE 1-continued

Preferred RSV G-specific antibodies according to the disclosure.

| SEQ ID NO | Antibody Identity | Sequence |
|---|---|---|
| | | aag aac acg ctg cat ctc cac atg aat agc ctg aga cat gag gac acg gct gtc tat ttc tgt gcc tcc cag ggg gca aag ggc ggt cac gaa ctt tct ttc tac tgt gct ttg gac gtc tgg ggc caa ggg acc acg gtc gcc gtc tcc tca |
| 257 | AT35 Heavy chain | gag gtg cag ctg gtg gag tct ggg gga ggc ttg gtc cag ccg ggg ggg tcc ctg aga ctc tcc tgt gca gcc tct gga ttc acc ttt agt acc tat tgg gtg agc tgg gtc cgc cag act cca ggg aag gga ctg gag tgg gtg gcc aac att aac caa gat gga agt gag aag tcc tat gtg gac tct gtg gag ggc cga ttc acc atc tcc aga gac aac gct aag aac tcg ctg tat ctg caa atg aac agc ctg aga gcc gac gac acg gct gta tat tat tgt gcg aga gaa gtc ttc gtg act cag gtg gag ccc gcg cag tgg ggc ttc tgg ggc cag gga acc ccg gtc atc gtc tcc tcc |
| 258 | AT36 Heavy chain | cag gtt cag gtg gtg cag tct gga gcc gag gtg aag aag cct ggg gcc tca gtc aag gtc tct tgc aag act tct ggt tac aac ttt atc gac cat agt gtc agc tgg gtg cga cag gcc ccc ggc caa ggg ctt gag tgg atg gga tgg atc agc cct tac aac cac aga aca gta tat gca gag aag ttc cag ggc aga gtc acc atg acc aca gac aca tcg acg agg aca gtc tcc atg gag ttg agg agg ctg aca tct gac gac acg gcc gtc tac ttc tgt gcg cga gat cga gta caa cag ggc gag gga aac ttc ttt gac cac tgg ggc cag gga acc ccg gtc acc gtc acc tca gcc |
| 259 | AT37 Heavy chain | cag ctg cag ctg cag gag tcc ggc tcc aga ctg gtg aag cct tca cag acc ctg tcc ctc acc tgc ggt gtc tct ggt ggc tcc atc agc agt ggt ggt tac tcc tgg aac tgg atc cgg cag cca cca ggg aag ggc ctg gag tgg gtt ggg tac atc tat cag aat gac atc acc tac tac aac ccg tcc ctc atg agt cga gtc acc ata tca gca gac acg tcc aag aac cag ttc tcc ctg aag ttg agc tct gtg acc gcc gcg gac acg gcc gtg tat tac tgt gcc cga ggg gcc tat ggt tcg gga act tat tat tcc gct gat gct ctt gat ata tgg ggc caa ggg aca atg gtc acc gtc tct tca |
| 260 | AT39 Heavy chain | cag gtc cag ctt gtg cag tct ggg cct gag gtg aag aag cct ggg gcc tca gtg agg ctt tcc tgt acg gcc tct gga aac acc ttc cgt acc tat gct gta cat tgg gtg cgc cag gcc tcc gga caa aga ctt gag tgg atg gga tgg atc aac cct gac aat ggt gac aca aaa tat tca cag agg ttc cag ggt aga gtc gtc att acc agg gac aca tcc gcg agg ata atc tac ttg gac ctg agc agc ctg aca tct gaa gac acg gct gtg ttc tat tgt ttc agc ggg aga att ttt gat ata tgg ggc caa ggg aca acg atc acc gtc tct tca |
| 261 | AT40 Heavy chain | cag gtg cag ctg gtg gag tcc ggg gga ggc gtg gtc cag cct ggg atg tcc cac aga ctc tcc tgt gca gcc tct aca ttg atc ttc gat aga cat gct ctc cac tgg gtc cgc cag gct cca ggc gcg ggc ctg gag tgg gtg gcg att ctc tct tat gat ggg acc aca gac tac tac gca gac tcc gtg aag ggc cga ttc acc gtc tcc aga gac acc tcc aag aac aca gtg ttt cta caa atg aac ggc ctg aga cct caa gac acg gct gtt tat tac tgt gcg aga gga agg gcc cta gat gac ttc gct gac tac ggg gga tac tac ttt gac tac tgg ggc cag gga atc ctg gtc acc gtc tcc tca |
| 262 | AT42 Heavy chain | cag gtg cag ctg cag gag tcc ggc cca gga ctg gtg cag cct tcg gag acc ctg tcc ctc act tgc act gtt tct ggt gac tcc atc acc agt aat gtt tac tac tgg tcc tgg atc cgc cag ccc cca ggg aag ggg ctg gag tgg att ggg agt atc ttt cat agt ggg atc acc cac tat acc ccg tcc ctc aat agt cga gtc acc ata tcc gtc gac acg tcc aag aac cag ttc tcc ctg aga ctg agt tct gcg acc gcc gca gac acg gct gta tat tat tgt gcg agg cat tgg gct ggc ctc tac ttt gac tct tgg ggc cag gga gcc ctg gtc gcc gtc tcc tca |
| 263 | AT43 Heavy chain | cag gtt cag gtg gtg cag tct gga cct gag gtg aag aag cct ggg gcc tca gtg agg gtc tcc tgc aag gct tct ggt tac acc ttt acc aac tat ggt gtc agc tgg gtg cga cag gcc cct gga caa ggg ctt gag tgg atg gga tgg atc agc act tac aat ggt aac aca tgg tat tca cag aag ttc cag gcc aga gtc acc aca aca gcc tac atg gag gtg agg agc ctg aga tct gac gac acg gcc ata tat tac tgt gcg tgc cac ggg agt ggc aat tac tac ggc gaa gcg aac tac ttt gac cac tgg ggc cag gga acc ctg gtc acc gtc tcc tcc |

TABLE 1-continued

Preferred RSV G-specific antibodies according to the disclosure.

| SEQ ID NO | Antibody | Identity | Sequence |
|---|---|---|---|
| 264 | AT44 | Heavy chain | cag gtg cag ctg cag gcg tcg ggc cca gga ctg gtg aag cct tcg gag acc ctg tcc ctc acc tgt aat gtc tct ggc tac tcc gtc agt agc ggt cac tac tgg gcc tgg gtc cgg cag tcc cca ggg aag ggg ctg gag tgg att ggg ggt atc cat cat agt ggg agt acc tac acc aat ccg ccc ctc aag agc cga gtc tcc ata tca ata gac acg tcc aag aac cag ttc tct ttg agg ttg acc tct gtg acc gcc gca gac acg gcc gtg tat ttc tgt gcg aga gat ctg tac gat ctt tcg acg ggg cct ttt tgg ttc gac ccc tgg ggc cag gga acc ctg gtc acc gtc tcc tca |
| 265 | AT45 | Heavy chain | cag gtg cac ctg gtg cag tct ggg gct gag gtg aag aag cct ggg tcc tcg gtg aag gtc tcc tgc aag gct tct gga acc ttc aac ggc cat gct atc agc tgg ata cga cag gcc cct gga caa gga ctt gag tgg aag gga ggg atc atc cct ggc ctt ggt aca aca agg tac gca cgg aag ttc cag gac aga gtc acg att acc gcg gac gaa tcc acg agg aca gcc tac atg gag ctg agc agg ctg aga tct gag gac acg gcc gtc tat tac tgt gcg aga gtg gcc ggg gga tac ttc gat agt gct act cga ggc tgg ggc cag gga acc ctg gtc acc gtc tcc tca |
| 266 | AT47 | Heavy chain | cag gtt cag ctg gtg cag tct gga ggt gag gtg aag aag cct ggg gcc tca gtg aag gtc tcc tgt aag gct tct ggt tac acc ttt acc aac tac ggt atc tgt tgg gtg cga cag gcc cct gga caa ggg ctt gaa tgg atg gga tgg atc agc ggt tac aat ggt aac aca tac tat gca cag aac ttc cag ggc aga gtc acc atg acc aca gac aca tcc acg agc aca gcc tac atg gag ctg agg agc ctg aga tct gac gac acg gcc gta tat tac tgt gcg aga ggg ttt cac tat cat agt gct gat cag aga ata ttc gac ccc tgg ggc cag gga acc ctg gtc acc gtc tcc tca |
| 267 | AT49 | Heavy chain | cag gtg ctt ctg gtg cag tct ggg gct gag ata aag aag cct ggg tcc tcg gtg aaa atc tcc tgc aag gcc tct gga ggg acc ttc agc agc ctt gct ctc aat tgg gtg cga cag gcc cct gga cag ggg ctt cag tgg atg gga ggg atc atc cct ctc ttt ggc act caa aac tac gca cag aag ttc cag ggc aga gtc acc att acc gcg gac gaa tcc acg agc aca gcc tac atg gag ctg agc ggc ctg cga ccc gag gac acg gcc gtc tat tac tgt gcc cta ttt ctt tgg ttc ggg gac caa acg agt gat gat ggt ttt gat gtc tgg ggc caa ggg aca gtg gtc acc gtg tct tca |
| 268 | AT50 | Heavy chain | cag gtt cag ctg gtg cag tct gga act gag gtg aag aag cct ggg gcc tca gtg aag gtc tcc tgc aag gct tct ggt tac acc ttt agc aac tat ggt atc agt tgg gtg cga cag gcc cct gga caa ggg ctt gag tgg atg gga tgg atc agc gct tac aat ggt aac aca tac tat aga cag gag ctc cag ggc aga gtc acc atg acc aca gac aca tcc acg agc aca gcc tac atg gag ctg agg agc ctg aga tct gac gac acg gcc gtg tat tac tgt gcg aga ggg ggt gcc caa gag atg gtt aga ata cac tac tac tac tac gga atg gac gtc tgg ggc caa ggg acc acg gtc acc gtc tcc tca |
| 269 | AT51 | Heavy chain | cag gtt cag ctg gtg cag tct gga gct gag gtg aag aag cct ggg gcc tca atg acg gtc tcc tgc aag gcc tct ggt tac acc ttt tcc aag tat ggc atc aac tgg gtg cga cag gcc cct gga caa ggg ctt gag tgg ctg ggt tgg atc agc gca tac aat ggc aac aca tac tat gca cag aag ttc cag ggc aga gtc acc atg acc aca gac aca gcc acg agc aca gcc tac atg gac gtg agg aac ctg aga tct gac gac acg gcc atg tat tac tgt gcg agg ccc gca acc tca tat gac gat ctt cgg agt ggt tat ttg aac tac tgt gac tac tgg ggc cag gga acc ctg gtc acc gtc tcc tca |
| 270 | AM22 | Heavy chain | cag gtc cag ctg gta cag tct ggg gct gag gtg aag aag ccc ggg gcc aca gtg aaa gtc tcc tgc aag gca acc ggc ctc att aaa tta tcc att cac tgg gtg cga cag gct cct gga aag ggg ctt gag tgg atg gga ggt tat gag ggt gag gtc gat gag att tcc tac gca cag aag ttc cag cac aga ctc acc gtg atc gcc gac aca gcg aca gac aca gtc tac atg gaa ctg ggc agg ctc acc tct gac gac acg gcc gtc tat ttc tgt gga aca cta ggt gtg aca gtg act gag gct gga ctg ggg atc gat gac tac tgg ggc cag gga acc ctg gtc acc gtc tcc tca |
| 271 | AT46 | Light chain | cag cct gtg ctg act caa tcg ccc tct gcc tct gcc tcc ctg gga gcc tcg gtc aag ctc acc tgc act ctg agc agt ggg cac agg aac tac gcc atc gca tgg cat cag cag cga cca gag aag ggc cct cgt tac ttg atg aag att tat act aat ggc agc cac tac ccg ggg gac ggg acc cct gat cgc ttc tca ggc tcc agc tct ggg gct gag cgc |

TABLE 1-continued

Preferred RSV G-specific antibodies according to the disclosure.

| SEQ ID NO | Antibody Identity | | Sequence |
|---|---|---|---|
| | | | tac ctc acc atc tcc agc ctc caa tct gag gat gag gct gac tat tac tgt cag acc tgg ggc gct ggc att tgg gtt ttc ggc gga ggg acc aag ctg acc gtc cta ggt cag ccc aag |
| 272 | AT32 | Light chain | gac atc gtg atg acc cag tct cca gac tcc ctg gct gtg tct ctg ggc gag agg gcc acc ttc agc tgc aag tcc agc cag agt gtt tta tac gac tcc aac aat aag aac tac tta gct tgg tac cag cag aga cca gga cag cct cct aag ttg ctc att tac tgg gcg tct acc cgg gaa tcc ggg gtc cct gac cga ttc agt ggc agc ggg tct ggg aca gat ttc act ctc acc atc agc agt ctg cag cct gaa gat gtg gca gtt tat tac tgt caa caa tat tat gat cct ctc atc acc ttc ggc caa ggg aca cga ctg gag att aaa cga act gtg |
| 273 | AT33 | Light chain | tcc tat gag ctg act cag cca ccc tcg gtg tca gtg tcc cca gga cag acg gcc agg atc acc tgc tct gca gat gca ttt tca gac caa tat gct tat tgg tac cag cag aag cca ggc cag gcc cct gtg ttg gtg ata tat aaa gac act gag agg ccc tca ggg atc cct gag cga atc tct ggc tcc agc tca ggg aca aca gcc acg ttg agc atc agt gga gtc cag gca gaa gac gag gct gac tat tac tgt caa tca aca gac acc agt ggt cct tta ttc ggc gga ggg acg aag ctg acc ctc cta ggt cag ccc aag |
| 274 | AT34 | Light chain | gac atc cag atg acc cag tct cct tcc acc ctg tct gca tct gtg gga gac aga gtc acc atc act tgt cgg gcc agt cag ggt att ggt agt tgg ttg gcc tgg tat cag cag aaa cca ggg aaa gcc cca aaa ctc ctg atc tat aac gcg tct ggt tta gaa agt ggc gtc cca tca ggg ttc agc ggc agt gga tct ggg aca gag ttc act ctc acc atc agc agc ctg cag cct gat gat tct gcg acg tat tac tgc caa caa tac aat agt cac acg tgg aca ttc ggc caa ggg acc aag gtg gaa ttc aag cga act gtg |
| 275 | AT35 | Light chain | gcc atc cag atg acc cag tct cca tcc tcc ctg tct gca tct gta gga gac aga gtc acc atc tct tgc cgg gca agt cag agc att gac aac tat tta aat tgg tat cag cag aaa ccg ggg aaa gcc cct aaa ctc ctg ctc ttt ctt gcg tcc act ttg caa agt ggt gtc cct tca agg ttc act ggc agt gga tct ggg aca gat ttc act ctc acc atc agc agt ctt caa cct gaa gat ttt gcg act tac tac tgt caa cag agc cac tct tcc ccc tac agt ttt ggc cag ggg acc aag ctt gag atc aaa cga act gtg |
| 276 | AT36 | Light chain | gac atc gtg atg acc cag tct cca gac tct ctg gct gtg tct ctg ggc gag agg gcc acc atc aac tgc aag tcc agc cag agt ctt tta cac agc tcc aac aat aag atc tac tta gct tgg tac cag cag aaa cca gga cag cct cct aag tta ctc ctt tac tgg gca tct acc cgg gag tcc ggg gtc cct gac cgc ttc act ggc agc ggg tct ggg aca gat ttc act ctc acc atc aac agc ctg cag gct gag gat gtg gct gtt tat tac tgt cag caa tat tat act act cat ccc act ttt ggc cag ggg acc agg ctg gag atc aaa cga act gtg |
| 277 | AT37 | Light chain | aaa att gtg ttg acg cag tct cca ggc acc ctg tct ttg tct cca ggg gaa aga gcc acc ctc tcc tgc agg gcc agt cag agt gtt agc gcc agc aac tta gcc tgg tac cag cag aaa cct ggc cag gct ccc agg ctc ctc atc tat ggt gca tcc agg acg gcc act ggc atc cca gac agg ttc agt ggc agt ggg tct ggg aca gac ttc act ctc tcc atc agc aga ctg gag cct gaa gat ttt gca gtg tat tac tgt caa cag tat ggt agc tca ccg ctc act ttc ggc gga ggg acc aag gtg gag atc aaa cga act gtg |
| 278 | AT39 | Light chain | gac atc cag atg acc cag tct cca tcc tcc ctg tca gca tct gtg gga gac aga gtc acc atc act tgc cag gcg agt cag gac att agc aac ttt tta aat tgg tat cag cag aaa ccg ggc caa gcc cct aaa ctc ctg atc tat gat gcg tcc aaa aca ttg caa tca ggg gtc cca tca agg ttc agt gga agt ggt tct gag aca gac ttt act ttc acc atc agc agc ctg cag cct gaa gat gtt gca aca tat tac tgt caa aag ttt gat aat ctc ctt ctc act ttc ggc gga ggg acc aag gtg gag ctc aag cga act gtg |
| 279 | AT40 | Light chain | gac atc cag atg acc cag tct cca tct tcc gta tct gcg tct gtg gga gac aaa gtc acc atc acc tgt cgg gcg agt cag ggt att agt acc tgg tta gcc tgg tat cag cag aaa cct ggg aaa gct gcc ctc ctg ata tat tct gca tcc aga ttg cag agt ggg gtc ccc tca agg ttt agc ggc agt gga tct ggg aca gat ttc act ctc acc atc agc agc ctg cag cct gaa gat tat gca acc tat tat tgt caa cag gct aac act ttc ccc ttc act ttc ggc cct ggg acc aaa gtg gac atc aaa cga act gtg |

TABLE 1-continued

Preferred RSV G-specific antibodies according to the disclosure.

| SEQ ID NO | Antibody Identity | | Sequence |
|---|---|---|---|
| 280 | AT42 | Light chain | gaa atc gtg ttg acg cag tct cca ggc acc ctg tct ctg tct cca ggg gaa aga gcc acc ctc tcc tgc agg gcc agt cag act gta agc agc agc cac tta gcc tgg tac cag cag aaa cct ggc cag gct ccc agg ctc ctc atc cat ggt tca tct agc agg gcc aca ggc atc cca gag agg ttc agt ggc agt ggg tct ggg cca gac ttc act ctc acc atc tcc aga ctg aag cct gaa gat ttt gct gtg tat tac tgt cag tac tat ggt gac tca ccc ggc tct ttc ggc gaa ggg acc aag gtg gag atc aaa cga act gtg |
| 281 | AT43 | Light chain | gac att gtg ttg acg cag tct cca ggc acc ctg tct ttg tct cca ggg gaa gga gcc acc ctc tcc tgc agg gcc agt cag agt gtt agc cgc aac tac tta gcc tgg tac cag caa aaa cct ggc cag gct ccc agg ctc ctc atc tat ggt gca tcc agc agg gcc att ggc atc cca gac agg ttc agt ggc agt ggg tct ggg aca gac ttc act ctc acc atc agc aga ctg gag cct gaa gat ttt gca gta tac tgc tgt cag cag tat act atc ttc cct ctc act ttc ggc gga ggg acc aag gtg gag atc aaa cga act gtg |
| 282 | AT44 | Light chain | gaa atc gtg atg acg cag tca cca gcc acc ctg tct gtg tct cca ggg gag aga gtc acc ctc tcc tgt agg gcc agt cag agt gtc agc acc aag gta gtc tgg tac cag cag aaa ttt ggc cag gct ccc agg ctc ctc atc tat ggt gca tcc acc agg gcc act ggt atc cca gtc agg ttc agt ggc agt ggg tct ggg aca gag ttc act ctc acc atc agc agc ctg cag tct gaa gat ctt gca gtt tat ttc tgt cag cag tat aat aag tgg ccc atg tac act ttt ggc cag ggg acc aag ttg gaa atc aaa cga act gtg |
| 283 | AT45 | Light chain | gat att gtg atg act cag tct cca ctc tcc ctg ccc gtc acc cct gga gag tcg gcc tcc atc tcc tgc agg tct agt cag agc ctc ctg cat agt aat gga tac aac tat ttg gat tgg tac ctg cag aag cca ggg cag tct cca cag ctc ctg atc tat ttg ggt tct aat cgg gcc ccc ggg gtc cct gac agg ttt agt ggc agt gga tca gga aca gat ttt aca ctg aaa atc agc aga gtg gag gct gag gat gtt ggg gtt tat tac tgc atg caa gct cta caa act cct acg ttc ggc caa ggg acc aag gtg gaa atc aaa cga act gtg |
| 284 | AT47 | Light chain | gac atc cag atg acc cag tct cct tcc acc ctg tct gca tct gta gga gac aga gtc acc atc act tgc cgg gcc agt gag agt att agt acc tgg ttg gcc tgg tat cag cag aaa cca ggg aaa gcc cct aac ctc ctg atc tat aag gcg tct agt tta gaa agt ggg gtc cca tca agg ttc agc ggc agt gga tct ggg aca gaa ttc act ctc gcc atc agc agc ctg cag cct gat gat ttt gca act tat tac tgc caa cag tat aaa agt tac ccg tac act ttt ggc cag ggg acc aag ctg gag ctg aaa cga act gtg |
| 285 | AT49 | Light chain | gat att gtg atg act cag tca ccg ctc tcc ctg acc gtc acc ccg gga gag ccg gcc tcc atc tca tgc agg tct agt cag agc ctc ctg cat ggt aat gga tac aaa tat ctg tgg tac ctg cag aag cca ggg cag tct cca cag ctc ctg atc tat ttg ggt tct aat cgg gcc tcc ggg gtc cct gcc agg ttc agc ggc agt gga tca gac aca gat ttt act ctg aaa atc agc acc gtg gag act gag gat gtt ggg gtt tat tac tgc atg caa gct cta caa agt ccg acg ttc ggc caa ggg act aag gtg gaa atc aaa cga act gtg |
| 286 | AT50 | Light chain | gac atc cag ttg acc cag tct cca tcc ttc ctg tct gca tct gta gga gac aga gtc acc atc act tgc cgg gca agc cag tcc att agc agt tat tta gcc tgg tat cag caa aca cca ggg aga gcc cct aag ctc ctg atc tat ggt gca tcc acg tta caa act ggg gtc cca tca agg ttc agc ggc agt gga tct ggg aca gaa ttc act ctc aca atc agc agc ctg cag cct gaa gat ttc gca act tat ttc tgt caa cag ctt aat act tac ccc ctc act ttc ggc cct ggg acc aaa gtg gag atc aaa cga act gtg |
| 287 | AT51 | Light chain | gac atc cag ttg acc cag tct cca tcc ttc ctg tct gca tct gta gga gac aga gtc acc atc act tgc cgg gca agc cag ggc att acc agt tat tta gcc tgg tat cag caa aaa cca ggg aga gcc cct aag ctc ctg atc tat gct gca tcc act ttg caa agt ggg gtc gca tca agg ttc agc ggc agt gga tct ggg aca gaa ttc act ctc aca atc agc agc ctg cag cct gaa gat ttt gca act tat tac tgt caa cag ttt cat act tac ccg ctc act ttc ggc gga ggg acc aag gtg gag atc aaa cga act gtg |
| 288 | AM22 | Light chain | gaa att gtg ttg aca cag tct cca ggc acc ctg tct ttg tct cca gga gaa aga gcc acc ctc tcc tgc agg gcc agt cag att gtt agc |

TABLE 1-continued

Preferred RSV G-specific antibodies according to the disclosure.

| SEQ ID NO | Antibody Identity | Sequence |
|---|---|---|
| | | agg aac cac tta gcc tgg tac cag caa aaa cct ggc cag gct ccc agg ctc ctc atc ttt ggt gcg tcc agt cgg gcc act ggc atc cca gtc cgg ttc agt ggc agt ggg tct ggg aca gac ttc act ctc acc atc aac gga ctg gcg cct gaa gat ttt gca gtt tac tac tgt ctg tcc tct gat tcc tcc ata ttc aca ttc ggc cct ggg acc aag gtg gat ttc aaa |

TABLE 2

Preferred combinations of RSV G-specific antibodies, according to the disclosure

| | | | | |
|---|---|---|---|---|
| AT43 + AT49 | AT43 + AT40 | | | |
| AT51 + AT34 | AT51 + AT40 | | | |
| AT47 + AT44 | AT47 + AT34 | AT47 + AT49 | AT35 + AT45 | AT35 + AT44 |
| AT35 + AT34 | AT35 + AT49 | AT35 + AT40 | | |
| AT37 + AT45 | AT37 + AT34 | AT37 + AT49 | AT37 + AT40 | |
| AT39 + AT45 | AT39 + AT44 | AT39 + AT34 | AT39 + AT49 | AT39 + AT40 |
| AT32 + AT45 | AT32 + AT44 | AT32 + AT34 | AT32 + AT49 | AT32 + AT40 |
| AT32 + AT31 | | | | |
| AT33 + AT45 | AT33 + AT44 | AT33 + AT34 | AT33 + AT49 | AT33 + AT40 |
| AT33 + AT42 | AT33 + AT38 | AT33 + AT50 | AT33 + AT36 | AT33 + AT46 |
| AT42 + AT44 | | | | |
| AT46 + AT38 | AT46 + AT45 | AT46 + AT44 | AT46 + AT34 | AT46 + AT49 |
| AT46 + AT40 | | | | |
| AT36 + AT45 | AT36 + AT44 | AT36 + AT34 | AT36 + AT49 | |
| AT50 + AT44 | AT50 + AT40 | | | |
| AT31 + AT44 | AT31 + AT34 | | | |

TABLE 3

Particularly preferred combinations of RSV G-specific antibodies, according to the disclosure

| | | | | |
|---|---|---|---|---|
| AT43 + AT49 | | | | |
| AT51 + AT34 | | | | |
| AT47 + AT34 | | | | |
| AT35 + AT45 | AT35 + AT44 | AT35 + AT34 | | |
| AT37 + AT45 | AT37 + AT34 | | | |
| AT39 + AT45 | AT39 + AT34 | AT39 + AT49 | AT39 + AT40 | |
| AT32 + AT45 | AT32 + AT44 | AT32 + AT34 | AT32 + AT40 | |
| AT32 + AT31 | | | | |
| AT33 + AT45 | AT33 + AT44 | AT33 + AT34 | AT33 + AT49 | AT33 + AT40 |
| AT33 + AT42 | AT33 + AT38 | AT33 + AT50 | AT33 + AT46 | |
| AT46 + AT45 | AT46 + AT44 | AT46 + AT34 | | |
| AT46 + AT40 | | | | |
| AT36 + AT45 | AT36 + AT34 | AT36 + AT49 | | |
| AT50 + AT44 | | | | |
| AT31 + AT34 | | | | |

TABLE 4

Summary of preferred RSV G-specific antibodies, according to the disclosure.

| | | | competition w/ antibodies binding the conserved RSV G domain | | |
|---|---|---|---|---|---|
| AT No. | epitope | CDC virus IC50 (ng/ml) | 131-2G | 3D3 | synergy w/D25 |
| RSV A+ 46 | non-linear | 325 | No | No | Yes |
| RSV B+ 42 | non-linear | ND | Yes | partially | No |
| 40 | | 18 | Yes | Yes | No |
| 44 | | 20 | Yes | Yes | No |
| 45 | | 108 | Yes | partially | No |
| 49 | | ND | Yes | Yes | No |
| 34 | | >1000 | Yes | Yes | No |

TABLE 4-continued

Summary of preferred RSV G-specific antibodies, according to the disclosure.

| AT No. | epitope | CDC virus IC50 (ng/ml) | competition w/ antibodies binding the conserved RSV G domain | | synergy w/D25 |
|---|---|---|---|---|---|
| | | | 131-2G | 3D3 | |
| RSV A+ 32-33-35 | | 20-10-79 | No | No | Yes |
| 36-37-39 | | 98 (AT39) | No | No | No |
| 43-47-50-51 | non-linear (43-47) | No | yes (47) | partially (51) | No |

TABLE 5

Binding of B cell supernatants containing anti-RSV G IgG to RSV infected cells expressing native viral proteins, detected with anti-huIgG-PE.

| clone name | RSV A2 | RSV X subtype A | RSV 2007-2 subtype B |
|---|---|---|---|
| AT46 | + | + | + |
| AT42 | + | + | + |
| AT40 | + | + | + |
| AT44 | + | + | + |
| AT45 | + | + | + |
| AT49 | + | + | + |
| AT34 | + | + | + |
| AT32 | + | + | neg |
| AT33 | + | + | neg |
| AT35 | + | + | neg |
| AT36 | + | + | neg |
| AT37 | + | + | neg |
| AT39 | + | + | neg |
| AT43 | + | + | neg |
| AT47 | + | + | neg |
| AT50 | + | + | neg |
| AT51 | + | + | neg |
| palivizumab | + | + | + |
| rD25 | + | + | + |
| ctrl anti IgG-PE | neg | neg | neg |

TABLE 6

Summary of antibody binding to RSV infected cell lysates by ELISA and Western Blot.

| antibody clone | ELISA | WB |
|---|---|---|
| AT46 | − | − |
| AT42 | − | − |
| AT40 | + | + |
| AT44 | + | + |
| AT45 | + | + |
| AT49 | + | + |
| AT34 | + | + |
| AT32 | + | + |
| AT33 | + | + |
| AT35 | + | + |
| AT36 | + | + |
| AT37 | + | + |
| AT39 | + | + |
| AT43 | +/− | +/− |
| AT47 | +/− | +/− |
| AT50 | + | + |
| AT51 | + | + |

TABLE 7a $k_a$, $k_d$ and $K_D$ of antibodies AT40, AT44, AT32, AT42 and AT49 to RSV Ga. $k_a$ is indicated in $10^4$ sec$^{-1}$*M$^{-1}$, kd in $10^{-4}$ sec$^{-1}$, $K_D$ in nM. Constants were fitted in Scrubber2, using a global fit to all SPR curves.

| Antibody: | $k_a$: | $k_d$: | $K_D$ (RSV A2 (G)): |
|---|---|---|---|
| AT32 | 75 (±21) | 4.3 (±0.3) | 0.6 (±0.1) |
| AT40 | 35 (±2) | 0.6 (±0.1) | 0.2 (±0.01) |
| AT42 | 64 (±11) | 7.6 (±1.7) | 1.3 (±0.4) |
| AT44 | 35 (±4) | 0.3 (±0.1) | 0.1 (±0.02) |
| AT49 | 22 (±3) | 0.3 (±0.04) | 0.1 (±0.01) |

TABLE 7b ka, kd and KD of antibodies AT40, AT44, AT42 and AT49 to RSV Gb.

| Antibody: | $k_a$: | $k_d$: | $K_D$ (RSV G (B1)): |
|---|---|---|---|
| AT40 | 34 (±10) | 0.3 (±0.15) | 0.1 (±0.07) |
| AT42 | 40 (±14) | 1.0 (±0.11) | 0.3 (±0.1) |
| AT44 | 34 (±16) | 0.4 (±0.17) | 0.1 (±0.07) |
| AT49 | 12 (±6) | 0.5 (±0.02) | 0.5 (±0.2) |

BRIEF DESCRIPTION OF THE DRAWINGS

FIG. 1. Amino acid sequence of RSV G protein of two subtypes A (Ga) A2 and Long strain and of three subtypes B (Gb) viruses from the USA (the B1 strain), Turkey and Uruguay (SEQ ID NOS 289-293, respectively). * indicate conserved/identical amino acid residues.

FIG. 2. Screening B cell supernatants for specificity to the RSV F and G protein. RSV A2 infected, PKH2 Green Fluorescent labeled HEp2 cells were mixed with PFA fixed RSV G expressing VERO cells and incubated with 20 cell/well B cell culture supernatant. IgG antibodies that bound the HEp2 or VERO cells were detected with a mouse anti-human IgG-PE. Antibodies present in the B cell culture supernatant that bound the RSV infected HEp2 cells (population 1) but not the G expressing VERO cells (population 2) presumably recognize the RSV F protein. Antibodies recognizing both cell lines most likely recognize the RSV G protein.

Figure 6:
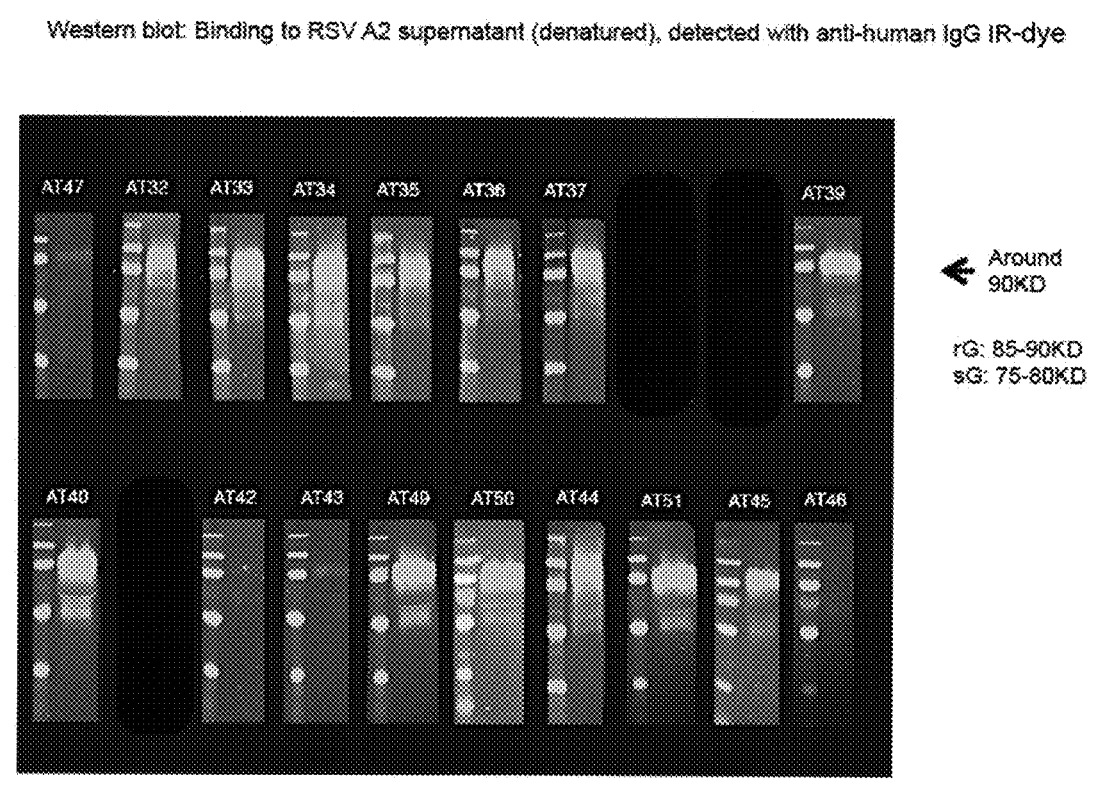

FIG. 6. Western Blots showing binding of RSV G-specific antibodies to RSV A2 supernatant (denatured), detected with anti-human IgG IR-dye.

DETAILED DESCRIPTION

Examples

Figure 3A:
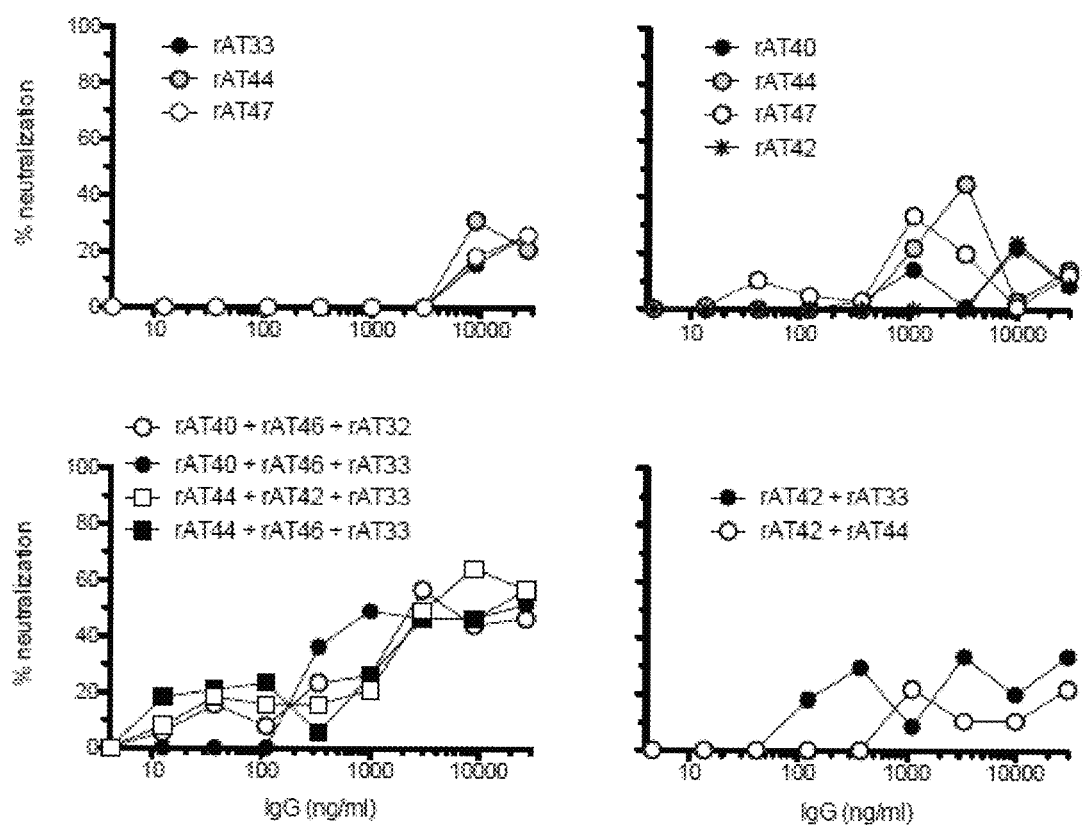
FIG. 3. Neutralization of RSV A2 by anti-RSV G protein specific human monoclonal antibodies in the absence and presence of complement. (A) Before RSV A2 was administered to HEp2 cells in 96-well plates, the virus was co-incubated with purified, recombinant AT32, AT33, AT40, AT42, AT44, AT46 and AT47 at 27 μg/ml. When combinations of 3 mAbs were tested the final concentration was 27 μg/ml, thus 9 μg/ml of each antibody. (B) Monoclonal B cell supernatant with anti-RSV G specific antibodies were first incubated with RSV virus for 1 hour at 37° C. before 10% rabbit serum complement was added for another hour in the presence of HEp2 cells. Cells were washed and cultured for 2 more days in normal culture medium.

Example 1: Generation of Human Monoclonal Antibodies Against the RSV G Protein by Transduction of Human Peripheral Blood Memory, IgG+ B Cells by BCL6 and Bcl-xL Materials and Methods
B Cell Isolation B cells were obtained from PBMCs from 40 to 50 ml Peripheral blood of three healthy adult volunteers by density gradient separation using Lymphoprep (Axis-Shield PoC, Oslo, Norway) and CD22 MACS microbeads (Miltenyi Biotech, Bergisch Gladbach, Germany). IgG memory B cells were isolated as CD19+CD3−CD27+IgM−IgA− population by FACSAria (Becton Dickinson, San Jose, Calif., USA).

The following mAbs against the human molecules CD3 (SK7), CD19 (SJ25C1), CD27 (O323; eBioscience), IgA (F(ab)2; DAKO Glostrup Denmark), IgD (IA6-2), IgG (G18-145), IgM (G20-127) (BD), Ig-kappa (F(ab)2; DAKO, G20-193), and Ig-lambda (F(ab)2; JDC12, DAKO) were directly labeled with fluorescein isothiocyanate (FITC), phycoerythrin (PE), phycoerythrin cyanine 5, (PE-Cy5), allophycocyanin (APC), phycoerythrin-indotricarbocyanine (PE-Cy7) or allophycocyanin-indotricarbocyanine (APC-Cy7) and were purchased from BD-Pharmingen (San Diego, Calif.) unless otherwise indicated. Stained cells were analyzed on an LSRII or FACSCanto (BD) and flow cytometry data were processed using FlowJo software (Tree Star, Ashland, Oreg., USA).

Retroviral Transduction

Use of the BCL6 and Bcl-xL retroviral construct has been described previously (Kwakkenbos et al. Generation of stable monoclonal antibody-producing B cell receptor-positive human memory B cells by genetic programming. Nature Medicine (2010) vol. 16 (1) pp. 123-8). Briefly, cDNAs encoding human BCL6, Bcl-xL and EGFP were cloned into the LZRS retroviral vector and retrovirus was generated by transfection Phoenix packaging cells (Shvarts et al. A senescence rescue screen identifies BCL6 as an inhibitor of anti-proliferative p19(ARF)-p53 signaling. Genes Dev (2002) 16:681-686). After enrichment (by ficoll density gradient and high speed cell sorting (FACSAria, BD)) and activation of human peripheral memory B cells on CD40L-L cells in the presence of rmIL-21, the cells were transduced. (Diehl et al. STAT3-mediated up-regulation of BLIMP1 is coordinated with BCL6 down-regulation to control human plasma cell differentiation. J Immunol (2008) 180(7):4805-15). Transduced cells express EGFP and can be sorted to enrich for cells that besides EGFP will express BCL6 and Bcl-xL.

B Cell Culture and Screening of Anti-RSV G Protein Specific B Cells

After 4 days from transduction, GFP positive cells were sorted by FACSAria, plated at 20 cells per well in ten 96-well flat-bottom tissue culture-treated plates per donor. After 14 days in culture, B cells and supernatants were harvested. B cells were frozen and supernatants were tested for binding capacity to RSV A2 virus infected HEp-2 cell. In brief, HEp-2 cell culture monolayers were infected with RSV A2 virus at a MOI of 2-3. The infected HEp-2 cells were harvested 48 hours after infection. Cells were stained with PKH2 Green Fluorescent Cell Linker Kit (Sigma-Aldrich, St. Louis, Mo., USA). In addition, B cell supernatants were screened simultaneously on paraformaldehyde (PFA) fixed RSV G protein transduced VERO cells (kindly provided by Myra Widjojoatmodjo, NVI, Bilthoven, The Netherlands) (FIG. 2). A mixture of 2.5E4 PKH2 stained RSV A2 virus infected HEp-2 cell and 2.5E4 RSV G protein expressing VERO cells were incubated for 1 hour at 4° C. with 100 µl of supernatant. Cells were washed once with IMDM supplemented with 1% FBS. IgGs binding to the target cells were detected with PE labeled anti-human IgG (SouthernBiotech, Birmingham, Ala., USA).

Double positive cells were plated at 1 cell per well in 96-well flat-bottom tissue culture-treated plates by FACSAria to obtain single clones. B cells were maintained in standard culture medium containing IMDM (Invitrogen), 8% FBS (HyClone) and penicillin/streptomycin (Roche) and were co-cultured on irradiated (50Gy) mouse L cell fibroblasts stably expressing CD40L (CD40L-L cells, 10E5 cells/ml) and recombinant mouse IL-21 (25 ng/ml, R&D systems, Minneapolis, Minn., USA). After 14 days in culture, supernatants were collected to test binding capacity to A2 virus infected HEp-2 cell by FACS. Table 4 shows an overview and some characteristics of the final 17 B cell clones of which recombinant antibodies were generated. Table 5 shows binding of the antibodies to Hep2 cells infected with RSV A2, RSV X (both subtype A viruses) and RSV 2007-2 (an RSV subtype B virus).

Cloning of Anti-RSV G Monoclonal Antibodies

Total RNA was isolated from approximately 5E5 monoclonal B cells with TRIzol® (Invitrogen). cDNA was generated and subjected to PCR to produce heavy and light chain fragments using 1U AmpliTaq Gold DNA polymerase (Applied Biosystems Inc. Foster City, Calif., USA). PCR products were run on agarose gels, purified and cloned into the pCR2.1 TA cloning vector according to manufacturers' recommendations (Invitrogen). Sequence analysis was performed using BigDye Terminator chemistry (Applied Biosystems Inc.) and Vector-NTI software (Invitrogen). To rule out reverse transcriptase and/or DNA polymerase induced mutations, several independent cDNA conversions and PCR reactions were performed and individually cloned and sequence analyzed.

IgG ELISA

Plates were coated with either anti-human IgG Fc-fragment (Jackson ImmunoResearch Laboratories, Bar Harbor, Me., USA) at 10 µg/ml in PBS for 1 hour at 37° C. or o/n at 4° C. and washed in ELISA wash buffer (PBS, 0.5% TWEEN®-20). 4% Protifar (Nutricia, Zoetermeer, The Netherlands) in PBS was used as blocking agent, before serial dilution of cell culture supernatants and enzyme-conjugated detection Abs were added (dilutions 1:2500 for HRP-conjugated anti-IgG (Jackson ImmunoResearch Laboratories, Inc.). TMB substrate/stop solution (Biosource, Carlsbad, Calif., USA) was used for development of the ELISAs.

Example 2: Functional Testing of 17 Unique, Fully Human Anti-RSV G Protein Specific Antibodies RSV Culture and Neutralization Assay An RSV A2 virus stock was obtained from supernatant of 3 day infected HEp2 cells maintained in standard culture medium. Supernatants were centrifuged and filtered (0.22 µM filter, Millipore). Subsequently aliquots were snap-frozen, stored in liquid nitrogen and virus titer was determined by standard TCID50 and PFU assay on adherent HEp2 cells. For neutralization assays 10E4 HEp2 cells were seeded in flat-bottom 96-well plates (Costar, Schiphol-Rijk, Netherlands) in standard culture medium. The next day 100TCID50 of RSV A2 and B cell culture supernatant were pre-incubated in the absence or presence of 10% rabbit complement serum (Sigma-Aldrich) before being added in triplicate to HEp2 cells for 1 hour at 37° C. After two days, cells were fixed with 80% acetone and stained with polyclonal anti-RSV-HRP (Biodesign, Kennebunk, Me., USA). 3-Amino-9-ethylcarbazole (AEC) was added for detection and visualization of RSV plaques by light microscopy (plaques were counted). In addition, RSV infected cells could also be stained with polyclonal goat anti-RSV directly labeled with-Alexa Fluor 647 (Molecular Probes). Fluorescent signal was detected with and analyzed by the automated fluorescent microscoop (Operetta, Perkin Elmer). Palivizumab (MedImmune, Gaithersburg, Md., USA) and D25 (WO 2008/147196) were used as positive control for RSV neutralization.

Results

RSV A2 neutralization experiments with antibodies derived from monoclonal B cell cultures did not result in neutralization in the absence of rabbit serum complement. In general antibody IgG concentrations in B cell supernatant vary between 600 and 2000 ng/ml, which could be too low. When we used increased concentrations of recombinant, purified monoclonal antibodies we did found that AT44 and AT47 could reduce virus infection (FIG. 3a, top panels). AT40, AT33 and AT42 did so only partially. This effect was not seen for the other 12 anti-RSV G antibodies (not shown). More interestingly, we found that combinations of anti-RSV G antibodies were able to neutralize the virus up to 50-60% without the addition of complement (FIG. 3a bottom panels).

Besides the direct neutralization we could identify a large group (9 out of 17) of monoclonal antibodies that neutralized RSV when virus and B cell culture supernatant were co-incubated with 10% rabbit serum complement thereby inducing complement dependent cytotoxicity (CDC) (FIG. 3b). IC50 values were between 10 and 325 ng/ml.

Not all antibodies did broadly recognize RSV-A and RSV-B strains. Depicted in Table 5 is the binding of antibodies to HEp2 cells infected with the RSV A2, RSV-X (subtype A) and a RSV-2007-2 strain of the B subtype (also summarized in Table 4).

Example 3: Synergistic Effect of RSV G Protein Specific Antibodies on the Neutralizing Capacity of Anti-RSV F Antibodies The role of the G protein on the surface of the RS virus is thought to be associated with target cell attachment. But also for other (unknown) process and mechanisms the G protein could be important, for example, the stabilization of the F protein trimer. It has been shown that the two proteins form a complex (Low et al., The RSV F and G glycoproteins interact to form a complex on the surface of infected cells, Biochemical and Biophysical Research Communications (2008) 366(2):308-13) and it has been shown that an anti-RSV G and RSV-F antibody in vivo can reduce virus titers in mice (Haynes et al., Therapeutic Monoclonal Antibody Treatment Targeting Respiratory Syncytial Virus (RSV) G Protein Mediates Viral Clearance and Reduces the Pathogenesis of RSV Infection in BALB/c Mice, J. Infect. Dis. (2009) 200(3):439-47). Without being bound by theory, antibodies directed against RSV G may influence the interaction between F and G and thereby induce 1) destabilization of the F trimer or 2) expose epitopes on the F trimer that become better accessible for anti-F antibodies; in either situation the F trimer may unfold to its post-fusion state and thereby become non-functional.

Figure 4A:
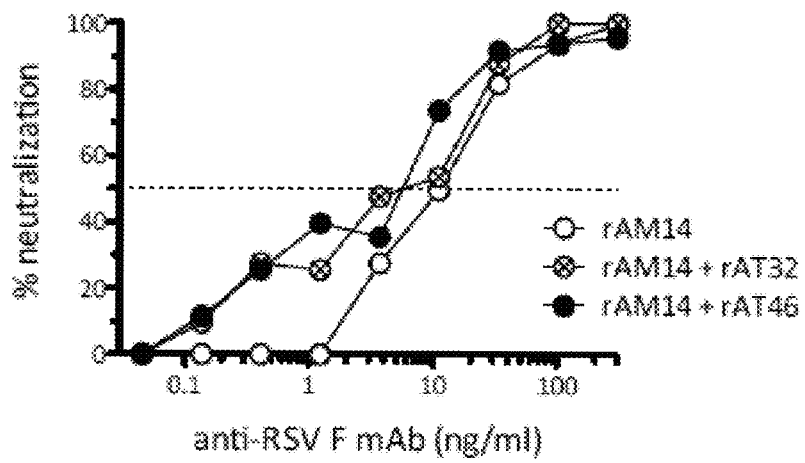
FIG. 4. Enhanced neutralization of RSV A2 virus by combinations of anti-RSV G and F protein specific antibodies. (A) Increasing amounts of RSV F specific antibodies and a fixed amount (500 ng/ml) of anti-RSV G antibody were co-incubated with 25 PFU of RSV A2 virus for 1 hour at 37° C. Subsequently, the virus antibody mixture was added to 20,000 HEp2 cells in solution in 96-well flat-bottom culture plates. After two days, the number of infected foci was determined. Antibody virus combinations were tested at least three times.
FIG. 4B shows the average increase compared to the F antibody alone.
Figure 4A:
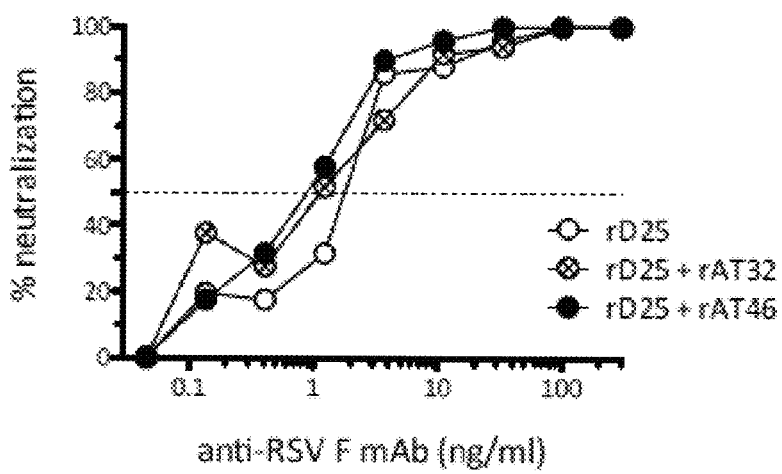
Figure 4A:
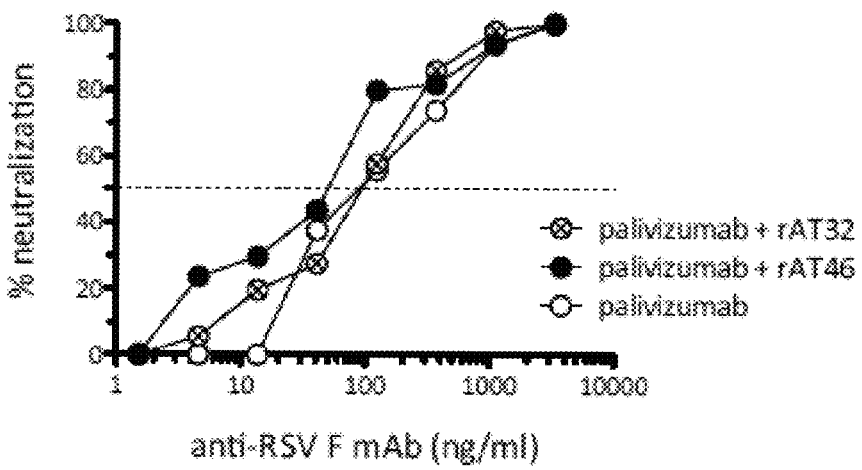
Figure 4B:
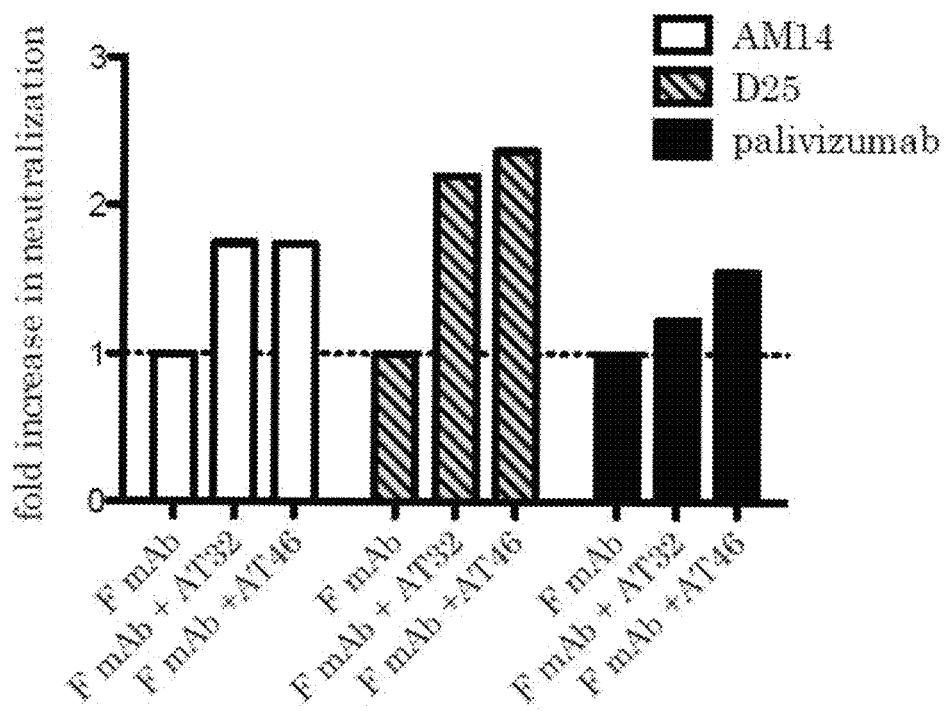
Figure 5:
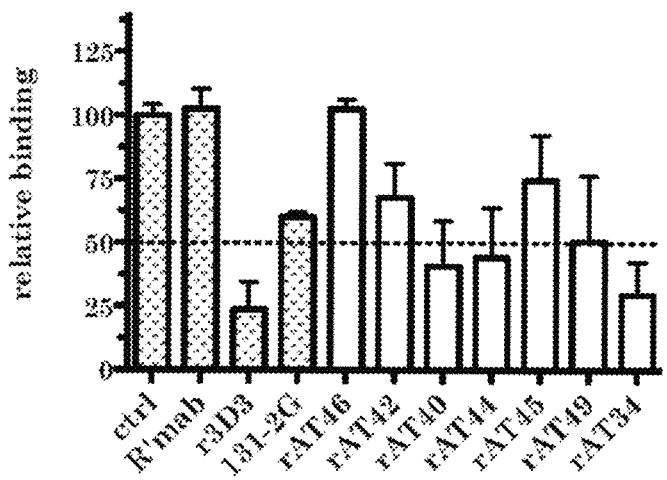
FIG. 5. 3D3 antibody-binding competition for the conserved domain on the RSV G protein. To analyze if the anti-RSV G antibodies bind within the conserved region of the RSV G protein we performed antibody competition assays. The antibodies were compared to 3D3, which binds the epitope HFEVFNFVP (aa 164-172, FIG. 1, US patent application US 2010-0285022 and Collarini et al. J Immunol (2009) 183: 6338-6345). 3D3 was directly labeled with ALEXA Fluor 647 (Molecular Probes) and antibody competition was determined by incubation of RSV-infected HEp2 cells with an increasing dose of the non-labeled antibody before the labeled antibody was added at a standard concentration. In addition, the assay was also performed by simultaneously incubation of the labeled and non-labeled antibodies, in general no differences between the two methods was detected. Shown in FIG. 5 is the average binding of ALEXA Fluor 647 labeled 3D3 antibody relative to the control of three separate experiments.
Figure 5:
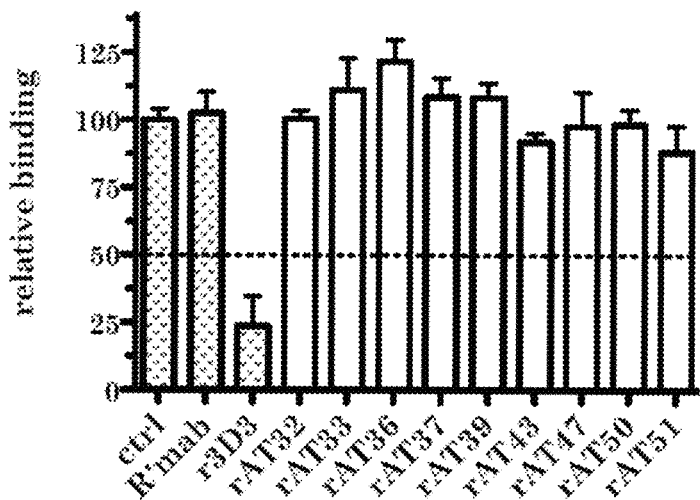

To study this we incubated RSV with increasing doses of anti-F antibodies e.g. D25, AM14 and palivizumab and with G specific antibodies (increasing concentrations or fixed at 500 ng/ml). As shown in FIG. 4a we observed that recombinant purified AT46 and AT32 did enhance the neutralizing capacity of AM14 and D25 but less of palivizumab. The synergistic effect was mainly seen at lower concentrations of anti-F antibody, the effect was consistent (the data shown is an average of three or more experiments) and the synergistic effect enhanced neutralization of the F antibodies by a factor 2 (FIG. 4b). Thus the G specific antibodies may induce changes in the presentation and/or stability of the F protein making the F protein more susceptible to neutralization by F specific antibodies.

Figure 1:
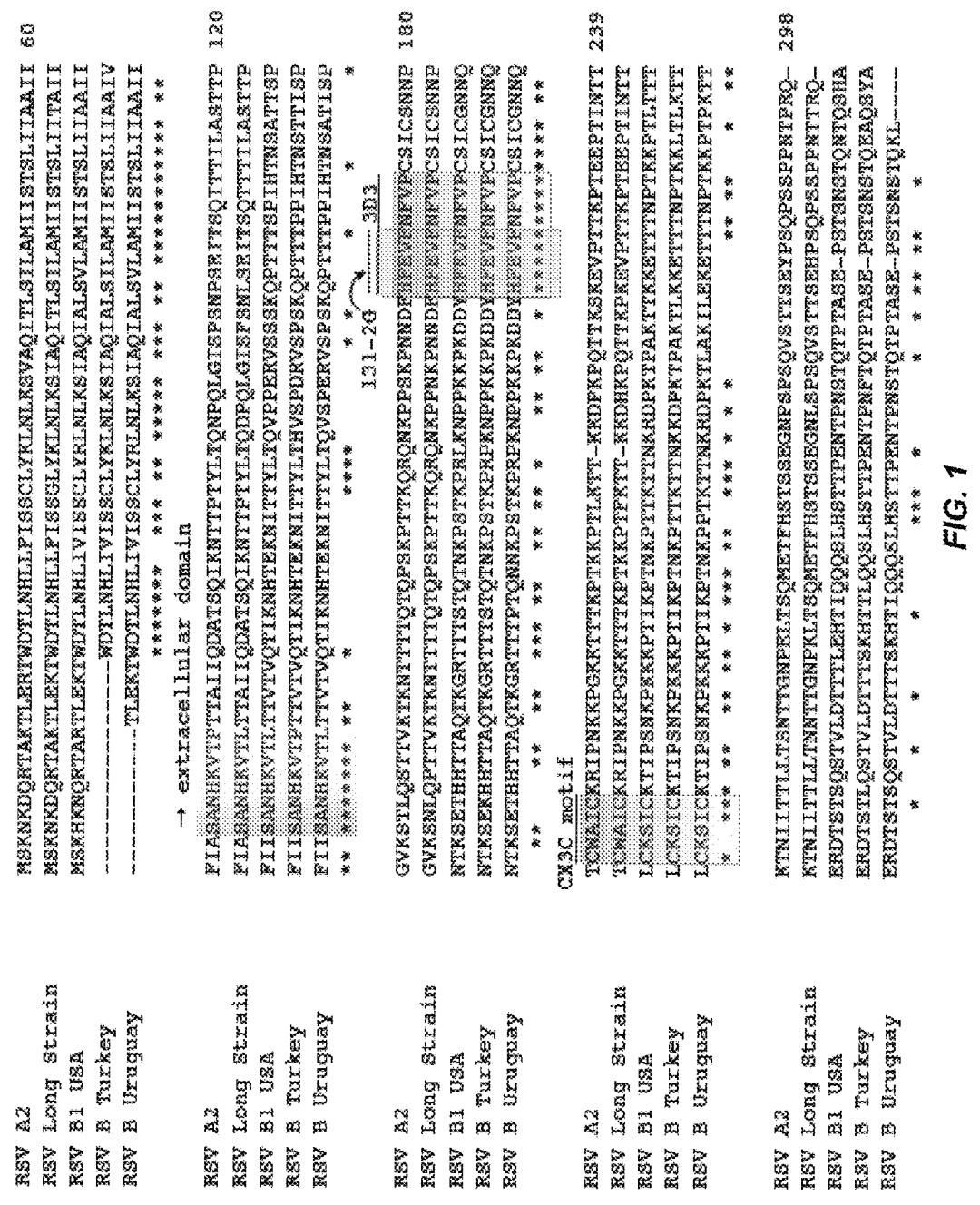

Example 4: Direct Labeling of Purified Antibodies to Determine Antibody-Binding Competition by FACS The RSV G protein can bind to the CX3C chemokine receptor 1 (CX3CR1) also named fractalkine receptor or G-protein coupled receptor 13 (GPR13). CX3CR1 is expressed on multiple cell lineages (NK cells, monocytes, Th1 CD4+ T cells and CD8+ T cells, mast cells and B cells. The ligand for CX3CR1, CX3CL1 induces adhesion of leukocytes when the chemokine is expressed as a membrane-anchored protein whereas the soluble form of CX3CL1 induces chemotaxis of leukocytes. The RSV G protein contains a conserved epitope (CWAIC residue 182 to 186, FIG. 1) that mimics the CX3CR1 binding epitope of CX3CL1. Antibodies exist that bind RSV G within the larger conserved domain (aa 169 to 191) and thereby (partially) compete with binding to CX3CR1 (Mekseepralard et al. Protection of mice against Human respiratory syncytial virus by wild-type and aglycosyl mouse-human chimaeric IgG antibodies to subgroup-conserved epitopes on the G glycoprotein. J. Gen. Virol. (2006) 87(Pt 5):1267-73). To analyze if the anti-RSV G antibodies disclosed herein bind similar epitopes we performed antibody competition assays. Antibodies disclosed herein were compared to 3D3 from Trellis Bioscience which binds the epitope HFEVFNFVP (aa 164-172, FIG. 1, U.S. patent application US 2010-0285022, and Collarini et al. Potent high-affinity antibodies for treatment and prophylaxis of respiratory syncytial virus derived from B cells of infected patients. J. Immunol. (2009) 183: 6338-6345). 3D3 was directly labeled with ALEXA Fluor 647 (Molecular Probes) and antibody competition was determined by incubation of RSV-infected HEp2 cells with an increasing dose of the non-labeled antibody before the labeled antibody was added at a standard concentration. In addition, the assay was also performed by simultaneous incubation of the labeled and non-labeled antibodies, in general no differences between the two methods were detected. Shown in FIG. 5 is the average binding of ALEXA Fluor 647 labeled 3D3 antibody relative to the control of three separate experiments. Binding of the 3D3 antibody can be out-competed by itself and antibodies that bind a similar or proximal epitope like the mouse antibody 131-2G (epitope HFEVF). Of the antibodies that bind RSV Ga and Gb (left panel), AT40, AT44 and AT34 strongly reduced 3D3 binding, suggesting that they compete for the same or proximal epitopes. AT42, AT45 and AT49 only partially compete with 3D3, which may suggest that they recognize different epitopes but may sterically hinder 3D3 from efficient binding. The antibody AT46 did not interfere with 3D3 binding. The right panel indicates competition of Ga specific antibodies with 3D3. None of the antibodies (AT32, 33, 36, 37, 39, 43, 50 and 51) did interfere with 3D3 binding, which indicates that they all recognize different RSV Ga specific epitopes.

Example 5: Binding of Anti-RSV G Antibodies in ELISA, SPR and WB

Antibodies, especially human antibodies, which contain relatively long variable domains (CDR regions), often recognize non-linear structures within their putative target. These non-linear structures can be disrupted by standard purification methods, which, for example, include denaturing compounds like TWEEN®. Our B cell technology is utmost suitable to screen for antibodies that recognize these non-linear structures since the method allows for functional screening of antibodies. However, this implies that not all antibodies discovered will recognize its putative target in standard binding assays like western blot (WB), surface plasma resonance (SPR) or ELISA. Besides AT46, AT42, AT43 and AT47 all antibodies gave clear signals in the ELISA (Table 6).

For the RSV ELISA 2 ml of 1% TRITON X®-100 in PBS was added to a cell pellet containing RSV infected Hep2 cells. The lysed cells were mixed thoroughly and kept for 5' at RT before 10 ml of ice cold PBS was added. The mixture was homogenized using a syringe with needle and cleared though a 0.22 μm filter (Millipore) or centrifuged at 5,000 rpm at 4° C. for 5'. Subsequently, the lysate was dialyzed against 1 L PBS overnight at 4° C. After dialyzation, 0.05% NaN3 was added and samples were stored at 4° C. until use, or stored at −80° C. for long-term storage.

ELISA plates were coated with a lysate of RSV infected HEp-2 cells in PBS for 1 hour at 37° C. or o/n at 4° C. and washed in ELISA wash buffer (PBS, 0.5% TWEEN®-20). Plates were blocked by incubation with 4% milk in PBS, before the anti-RSV antibodies or polyclonal goat anti-RSV (Biodesign) in combination with enzyme-conjugated anti-IgG antibodies were added (dilutions 1:2500 for HRP-conjugated anti-IgG (Jackson). TMB substrate/stop solution (Biosource) was used for development of the ELISAs.

To confirm antibody binding to RSV G, western blots were prepared which were loaded with denatured and boiled supernatants of RSV A2 infected HEp2 cells. These supernatants contain relatively high amounts of the secreted form of RSV G. Summarized in Table 6 and shown in FIG. 6 is a western blot on which antibodies that recognize RSV Ga only (AT32, 33, 35, 36, 37, 39, 50 and 51), bind relative strong to the RSV G protein. From the same group of RSV Ga only binding antibodies, AT47 and AT43 only weakly bind RSV G. From the panel of antibodies that recognize RSV Ga and Gb on infected cells only AT40, 44, 45, 49 and 34 recognize RSV Ga by western blot. AT46 and AT42 do not bind.

In addition, we generated surface plasmon resonance (SPR) data with the IBIS MX96 instrument (Krishnamoorthy et al., Electrokinetic label-free screening chip: a marriage of multiplexing and high throughput analysis using surface plasmon resonance imaging, Lab Chip (2010) 10(8): 986-90; van Beers et al., Mapping of citrullinated fibrinogen B-cell epitopes in rheumatoid arthritis by imaging surface plasmon resonance, Arthritis Research & Therapy (2010) 12(6):R219; Krishnamoorthy et al., Electrokinetic lab-on-a-biochip for multi-ligand/multi-analyte biosensing, Anal. Chem. (2010) 82(10):4145-50; de Lau et al., Lgr5 homologues associate with Wnt receptors and mediate R-spondin signaling, Nature (2011) 476(7360):293-7). The rate- and affinity constant of the antibodies were determined using a similar method as described in de Lau et al., Nature (2011).

Briefly, pre-activated SPR sensor chips (IBIS Technologies, Hengelo, Netherlands) were coated with an array of anti-human IgG specific spots (goat anti-human IgG, polyclonal, Fc-specific, Jackson ImmunoResearch Laboratories, Bar Harbor, Me., USA) using a continuous flow microspotter (CFM) (Wasatch Microfluidics, Salt Lake City, Utah, USA). After preparing the sensor chip, the chip was placed in the instrument and treated with RSV-G-specific human IgG. Each anti-IgG spot in the array thus captured a decreasing amount of IgG. After measuring a new baseline for each spot, purified RSV-Ga or Gb protein (Sino Biologics, Beijing, China) was injected to determine label-free surface plasmon resonance (Table 7a, 7b and FIG. 7*a*).

Kinetic parameters were calculated using Sprint 1.6.8.0 (IBIS Technologies, Hengelo, Netherlands) and Scrubber2 software (BioLogic software, Campbell, Australia). Results between experiments are comparable, the antibodies form stable complexes with the RSV G protein and similar $k_a$, $k_d$ and $K_D$ were generated. In contrast to the WB and ELISA data we do find binding of the AT42 antibody to RSV Ga and RSV Gb protein in the IBIS SPR (Tables 7a and 7b). AT46 did not bind to either the recombinant or denatured form of the protein, probably because AT46 binds to a conformational epitope, which is not present in the recombinant and denatured form of the G protein because their conformation differs from that of the protein expressed on the surface of the RS virus.

Example 6: Determination of the Epitope of Anti-RSV-G Antibodies

In addition, we performed studies to precisely determine the epitopes recognized by several anti-RSV G antibodies, according to the disclosure. Therefore, we generated 40 peptides containing a 5' biotin molecule plus a spacer followed by 12-successive amino acids, spanning the amino acid domain 149 to 199 of the RSV A2 G protein. This domain contains the conserved region, which is also recognized by the 131-2G and 3D3 antibody (FHFEVFNFV) and the cysteine rich domain forming the fractakine binding epitope (CWAIC). To detect binding to the peptides we obtained streptavidin-coated sensor chips (IBIS Technologies, Hengelo, Netherlands), on which the biotin labeled peptides were spotted using the CFM. Subsequently, the antibodies were run one by one over the chip at four different concentrations, after each run the chip was regenerated. Since the peptides were still present after regeneration, this indicated that the immobilized strepativin-biotin/peptides complexes were very stable.

Figure 7A:
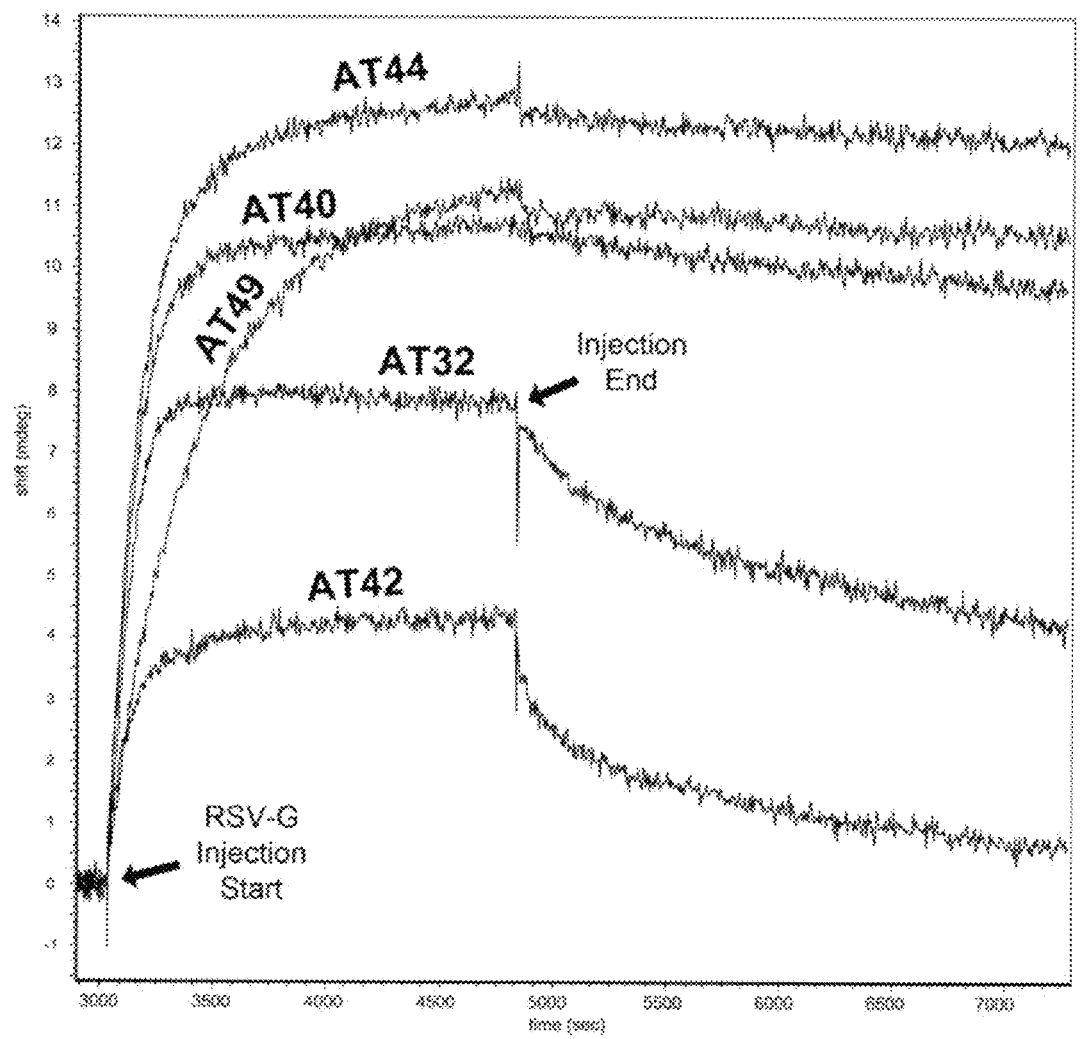
FIG. 7. (A) Example of recombinant full-length RSV Ga protein binding to human anti-RSV G antibodies captured on a SPR anti-human IgG chip. (B) Graph summarizes the binding of RSV G antibodies to biotinilated 12-mer peptides that were coupled to streptavidin coated on an IBIS SPR chip. The peptide library spans the amino acid sequence 149 to 199 of the RSV A2 strain. (C) Amino acid epitope recognize by the antibodies 3D3, AT40, AT44, 131-2G and AT32.
Figure 7B:
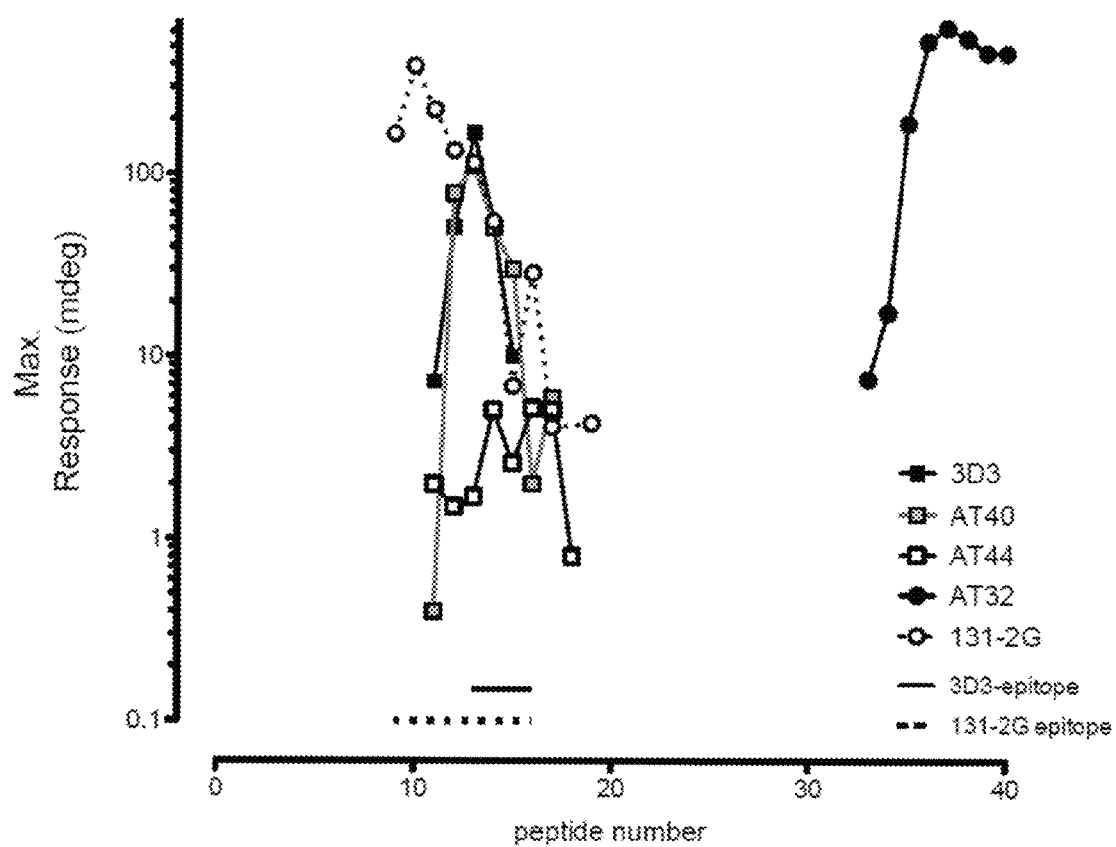

FIG. 7b shows the maximum response observed in the SPR instrument when antibodies recognized a certain peptide (1 to 40, as depicted below). The height of the signal is influenced by the affinity of the antibody for the peptide, the concentration of the antibody, the amount of peptide immobilized and the conformation/polarity of the peptide on the sensor chips (polarity of the FHFEVFNF is low). Together we can conclude that the epitope recognized 3D3, 131-2G, AT40 and AT44 are in close proximity of each other (FIGS. 7b and 7c). Antibodies AT42, AT46 and AT49 did not recognize any of the captured peptides on the chip (not shown), indicating that the epitope of these antibodies is at least partly located outside the amino acid domain 149 to 199 of the G protein or that these antibodies recognize a conformation not present when the peptides are captured on the chip.

The domain described for the 131-2G antibody; HFEVF (Tripp et al. CX3C chemokine mimicry by respiratory syncytial virus G glycoprotein, Nat. Immunol., 2001) could be confirmed by us. Regarding 3D3 we find that the antibody binds to the residues FHFEVFNF as core residues and FHFEVFNFV as the complete epitope. The epitope published for 3D3 is HFEVFNFVP (Collarini et al., Potent high-affinity antibodies for treatment and prophylaxis of respiratory syncytial virus derived from B cells of infected patients, J. Immunol., 2009), we, however, find one more residue at the beginning, (F163) which is necessary.

AT40 and AT44 both start at residue 165F. AT40's epitope then continues till residue F170, making the epitope consist of FEVFNF. AT44 needs at least residue E166 till F170, making the complete epitope ranging from EVFNF. To our current knowledge these antibody epitopes have never been described before. Antibody AT32, which only binds to RSV subtype A viruses did bind to the more distal epitope RIPNK (position 188 to 192), an epitope located just after the fractalkine binding site.

1  KQRQNKPPSKPN
2  QRQNKPPSKPNN
3  RQNKPPSKPNND
4  QNKPPSKPNNDF
5  NKPPSKPNNDFH
6  KPPSKPNNDFHF
7  PPSKPNNDFHFE
8  PSKPNNDFHFEV
9  SKPNNDFHFEVF
10 KPNNDFHFEVFN
11 PNNDFHFEVFNF
12 NNDFHFEVFNFV
13 NDFHFEVFNFVP
14 DFHFEVFNFVPC
15 FHFEVFNFVPCS
16 HFEVFNFVPCSI
17 FEVFNFVPCSIC
18 EVFNFVPCSICS
19 VFNFVPCSICSN
20 FNFVPCSICSNN
21 NFVPCSICSNNP
22 FVPCSICSNNPT
23 VPCSICSNNPTC
24 PCSICSNNPTCW
25 CSICSNNPTCWA
26 SICSNNPTCWAI
27 ICSNNPTCWAIC
28 CSNNPTCWAICK
29 SNNPTCWAICKR
30 NNPTCWAICKRI
31 NPTCWAICKRIP
32 PTCWAICKRIPN
33 TCWAICKRIPNK
34 CWAICKRIPNKK
35 WAICKRIPNKKP
36 AICKRIPNKKPG
37 ICKRIPNKKPGK
38 CKRIPNKKPGKK
39 KRIPNKKPGKKT
40 RIPNKKPGKKTT

The invention claimed is:

1. A composition comprising: a combination of AT44, AT42 and AT33; wherein said AT44, said AT42 and said AT33 are each isolated, synthetic or recombinant antibodies, or antigen binding fragments thereof; said AT44 comprises SEQ ID NO: 2, SEQ ID NO: 20, SEQ ID NO: 38, SEQ ID NO: 56, SEQ ID NO: 74 and SEQ ID NO: 92; said AT42 comprises SEQ ID NO:10, SEQ ID NO: 28, SEQ ID NO: 46, SEQ ID NO: 64, SEQ ID NO: 82 and SEQ ID NO: 100; and said AT33 comprises SEQ ID NO: 3, SEQ ID NO: 21, SEQ ID NO: 39, SEQ ID NO: 57, SEQ ID NO: 75 and SEQ ID NO: 93.

* * * * *

SEQUENCE LISTING

<160> NUMBER OF SEQ ID NOS: 346

<210> SEQ ID NO 1
<211> LENGTH: 6
<212> TYPE: PRT
<213> ORGANISM: Artificial
<220> FEATURE:
<223> OTHER INFORMATION: AT46 heavy chain CDR1

<400> SEQUENCE: 1

Ser Arg Tyr Val Met Ser
1               5

<210> SEQ ID NO 2
<211> LENGTH: 5
<212> TYPE: PRT
<213> ORGANISM: Artificial
<220> FEATURE:
<223> OTHER INFORMATION: AT32 heavy chain CDR1

<400> SEQUENCE: 2

Glu Leu Ser Ile His
1               5

<210> SEQ ID NO 3
<211> LENGTH: 5
<212> TYPE: PRT
<213> ORGANISM: Artificial
<220> FEATURE:
<223> OTHER INFORMATION: AT33 heavy chain CDR1

<400> SEQUENCE: 3

Ser Leu Ala Ile Ser
1               5

<210> SEQ ID NO 4
<211> LENGTH: 5
<212> TYPE: PRT
<213> ORGANISM: Artificial
<220> FEATURE:
<223> OTHER INFORMATION: AT34 heavy chain CDR1

<400> SEQUENCE: 4

His Tyr Gly Met His
1               5

<210> SEQ ID NO 5
<211> LENGTH: 5
<212> TYPE: PRT
<213> ORGANISM: Artificial
<220> FEATURE:
<223> OTHER INFORMATION: AT35  heavy chain CDR1

<400> SEQUENCE: 5

Thr Tyr Trp Val Ser
1               5

<210> SEQ ID NO 6
<211> LENGTH: 9
<212> TYPE: PRT
<213> ORGANISM: Artificial
<220> FEATURE:
<223> OTHER INFORMATION: AT36 heavy chain CDR1

<400> SEQUENCE: 6

Tyr Asn Phe Ile Asp His Ser Val Ser
1               5

```
<210> SEQ ID NO 7
<211> LENGTH: 7
<212> TYPE: PRT
<213> ORGANISM: Artificial
<220> FEATURE:
<223> OTHER INFORMATION: AT37 heavy chain CDR1

<400> SEQUENCE: 7

Ser Gly Gly Tyr Ser Trp Asn
1               5

<210> SEQ ID NO 8
<211> LENGTH: 5
<212> TYPE: PRT
<213> ORGANISM: Artificial
<220> FEATURE:
<223> OTHER INFORMATION: AT39 heavy chain CDR1

<400> SEQUENCE: 8

Thr Tyr Ala Val His
1               5

<210> SEQ ID NO 9
<211> LENGTH: 6
<212> TYPE: PRT
<213> ORGANISM: Artificial
<220> FEATURE:
<223> OTHER INFORMATION: AT40 heavy chain CDR1

<400> SEQUENCE: 9

Asp Arg His Ala Leu His
1               5

<210> SEQ ID NO 10
<211> LENGTH: 7
<212> TYPE: PRT
<213> ORGANISM: Artificial
<220> FEATURE:
<223> OTHER INFORMATION: AT42 heavy chain CDR1

<400> SEQUENCE: 10

Ser Asn Val Tyr Tyr Trp Gly
1               5

<210> SEQ ID NO 11
<211> LENGTH: 5
<212> TYPE: PRT
<213> ORGANISM: Artificial
<220> FEATURE:
<223> OTHER INFORMATION: AT43 heavy chain CDR1

<400> SEQUENCE: 11

Asn Tyr Gly Val Ser
1               5

<210> SEQ ID NO 12
<211> LENGTH: 6
<212> TYPE: PRT
<213> ORGANISM: Artificial
<220> FEATURE:
<223> OTHER INFORMATION: AT44 heavy chain CDR1

<400> SEQUENCE: 12

Ser Gly His Tyr Trp Ala
1               5
```

<210> SEQ ID NO 13
<211> LENGTH: 5
<212> TYPE: PRT
<213> ORGANISM: Artificial
<220> FEATURE:
<223> OTHER INFORMATION: AT45 heavy chain CDR1

<400> SEQUENCE: 13

Gly His Ala Ile Ser
1               5

<210> SEQ ID NO 14
<211> LENGTH: 5
<212> TYPE: PRT
<213> ORGANISM: Artificial
<220> FEATURE:
<223> OTHER INFORMATION: AT47 heavy chain CDR1

<400> SEQUENCE: 14

Asn Tyr Gly Ile Cys
1               5

<210> SEQ ID NO 15
<211> LENGTH: 5
<212> TYPE: PRT
<213> ORGANISM: Artificial
<220> FEATURE:
<223> OTHER INFORMATION: AT49 heavy chain CDR1

<400> SEQUENCE: 15

Ser Leu Ala Leu Asn
1               5

<210> SEQ ID NO 16
<211> LENGTH: 5
<212> TYPE: PRT
<213> ORGANISM: Artificial
<220> FEATURE:
<223> OTHER INFORMATION: AT50 heavy chain CDR1

<400> SEQUENCE: 16

Asn Tyr Gly Ile Ser
1               5

<210> SEQ ID NO 17
<211> LENGTH: 5
<212> TYPE: PRT
<213> ORGANISM: Artificial
<220> FEATURE:
<223> OTHER INFORMATION: AT51 heavy chain CDR1

<400> SEQUENCE: 17

Lys Tyr Gly Ile Asn
1               5

<210> SEQ ID NO 18
<211> LENGTH: 5
<212> TYPE: PRT
<213> ORGANISM: Artificial
<220> FEATURE:
<223> OTHER INFORMATION: AM 22 heavy chain CDR1

<400> SEQUENCE: 18

Lys Leu Ser Ile His
1               5

<210> SEQ ID NO 19
<211> LENGTH: 22
<212> TYPE: PRT
<213> ORGANISM: Artificial
<220> FEATURE:
<223> OTHER INFORMATION: AT 46  heavy chain CDR2

<400> SEQUENCE: 19

Ser Ile Thr Gly Ser Gly Ala Thr Thr Tyr Tyr Ala Asp Ser Val Lys
1               5                   10                  15

Gly Arg Phe Thr Ile Ser
            20

<210> SEQ ID NO 20
<211> LENGTH: 17
<212> TYPE: PRT
<213> ORGANISM: Artificial
<220> FEATURE:
<223> OTHER INFORMATION: AT32 heavy chain CDR2

<400> SEQUENCE: 20

Gly Phe Glu Pro Glu Asp Gly Glu Tyr Ile Tyr Pro Gln Lys Ser Gln
1               5                   10                  15

Gly

<210> SEQ ID NO 21
<211> LENGTH: 17
<212> TYPE: PRT
<213> ORGANISM: Artificial
<220> FEATURE:
<223> OTHER INFORMATION: AT 33 heavy chain CDR2

<400> SEQUENCE: 21

Gly Ile Ile Pro Lys Phe Asn Arg Arg Asp Tyr Ala Gln Lys Phe Gln
1               5                   10                  15

Gly

<210> SEQ ID NO 22
<211> LENGTH: 17
<212> TYPE: PRT
<213> ORGANISM: Artificial
<220> FEATURE:
<223> OTHER INFORMATION: AT34 heavy chain CDR2

<400> SEQUENCE: 22

Val Ile Ser Tyr Asp Gly Asp Lys Lys Tyr Tyr Ala Asp Ser Val Lys
1               5                   10                  15

Gly

<210> SEQ ID NO 23
<211> LENGTH: 17
<212> TYPE: PRT
<213> ORGANISM: Artificial
<220> FEATURE:
<223> OTHER INFORMATION: AT 35 heavy chain CDR2

<400> SEQUENCE: 23

Asn Ile Asn Gln Asp Gly Ser Glu Lys Ser Tyr Val Asp Ser Val Glu
1               5                   10                  15

Gly

<210> SEQ ID NO 24
<211> LENGTH: 17
<212> TYPE: PRT

```
<213> ORGANISM: Artificial
<220> FEATURE:
<223> OTHER INFORMATION: AT 36 heavy chain CDR2

<400> SEQUENCE: 24

Trp Ile Ser Pro Tyr Asn His Arg Thr Val Tyr Ala Glu Lys Phe Gln
1               5                   10                  15

Gly

<210> SEQ ID NO 25
<211> LENGTH: 16
<212> TYPE: PRT
<213> ORGANISM: Artificial
<220> FEATURE:
<223> OTHER INFORMATION: AT 37 heavy chain CDR2

<400> SEQUENCE: 25

Tyr Ile Tyr Gln Asn Asp Ile Thr Tyr Tyr Asn Pro Ser Leu Met Ser
1               5                   10                  15

<210> SEQ ID NO 26
<211> LENGTH: 22
<212> TYPE: PRT
<213> ORGANISM: Artificial
<220> FEATURE:
<223> OTHER INFORMATION: AT 39 heavy chain CDR2

<400> SEQUENCE: 26

Trp Ile Asn Pro Asp Asn Gly Asp Thr Lys Tyr Ser Gln Arg Phe Gln
1               5                   10                  15

Gly Arg Val Val Ile Thr
            20

<210> SEQ ID NO 27
<211> LENGTH: 17
<212> TYPE: PRT
<213> ORGANISM: Artificial
<220> FEATURE:
<223> OTHER INFORMATION: AT40  heavy chain CDR2

<400> SEQUENCE: 27

Ile Leu Ser Tyr Asp Gly Thr Thr Asp Tyr Tyr Ala Asp Ser Val Lys
1               5                   10                  15

Gly

<210> SEQ ID NO 28
<211> LENGTH: 16
<212> TYPE: PRT
<213> ORGANISM: Artificial
<220> FEATURE:
<223> OTHER INFORMATION: AT42  heavy chain CDR2

<400> SEQUENCE: 28

Ser Ile Phe His Ser Gly Ile Thr His Tyr Thr Pro Ser Leu Asn Ser
1               5                   10                  15

<210> SEQ ID NO 29
<211> LENGTH: 17
<212> TYPE: PRT
<213> ORGANISM: Artificial
<220> FEATURE:
<223> OTHER INFORMATION: AT 43 heavy chain CDR2

<400> SEQUENCE: 29

Trp Ile Ser Thr Tyr Asn Gly Asn Thr Trp Tyr Ser Gln Lys Phe Gln
```

Ala

<210> SEQ ID NO 30
<211> LENGTH: 16
<212> TYPE: PRT
<213> ORGANISM: Artificial
<220> FEATURE:
<223> OTHER INFORMATION: AT 44 heavy chain CDR2

<400> SEQUENCE: 30

Gly Ile His His Ser Gly Ser Thr Tyr Thr Asn Pro Pro Leu Lys Ser
1               5                   10                  15

<210> SEQ ID NO 31
<211> LENGTH: 17
<212> TYPE: PRT
<213> ORGANISM: Artificial
<220> FEATURE:
<223> OTHER INFORMATION: AT 45 heavy chain CDR2

<400> SEQUENCE: 31

Gly Ile Ile Pro Gly Leu Gly Thr Thr Arg Tyr Ala Arg Lys Phe Gln
1               5                   10                  15

Asp

<210> SEQ ID NO 32
<211> LENGTH: 17
<212> TYPE: PRT
<213> ORGANISM: Artificial
<220> FEATURE:
<223> OTHER INFORMATION: AT 47 heavy chain CDR2

<400> SEQUENCE: 32

Trp Ile Ser Gly Tyr Asn Gly Asn Thr Tyr Tyr Ala Gln Asn Phe Gln
1               5                   10                  15

Gly

<210> SEQ ID NO 33
<211> LENGTH: 17
<212> TYPE: PRT
<213> ORGANISM: Artificial
<220> FEATURE:
<223> OTHER INFORMATION: AT49  heavy chain CDR2

<400> SEQUENCE: 33

Gly Ile Ile Pro Leu Phe Gly Thr Gln Asn Tyr Ala Gln Lys Phe Gln
1               5                   10                  15

Gly

<210> SEQ ID NO 34
<211> LENGTH: 17
<212> TYPE: PRT
<213> ORGANISM: Artificial
<220> FEATURE:
<223> OTHER INFORMATION: AT 50 heavy chain CDR2

<400> SEQUENCE: 34

Trp Ile Ser Ala Tyr Asn Gly Asn Thr Tyr Tyr Arg Gln Glu Leu Gln
1               5                   10                  15

Gly

<210> SEQ ID NO 35

```
<211> LENGTH: 17
<212> TYPE: PRT
<213> ORGANISM: Artificial
<220> FEATURE:
<223> OTHER INFORMATION: AT 51 heavy chain CDR2

<400> SEQUENCE: 35

Trp Ile Ser Ala Tyr Asn Gly Asn Thr Tyr Tyr Ala Gln Lys Phe Gln
1               5                   10                  15
Gly

<210> SEQ ID NO 36
<211> LENGTH: 16
<212> TYPE: PRT
<213> ORGANISM: Artificial
<220> FEATURE:
<223> OTHER INFORMATION: AM 22 heavy chain CDR2

<400> SEQUENCE: 36

Gly Tyr Glu Gly Glu Val Asp Glu Ile Phe Tyr Ala Gln Lys Phe Gln
1               5                   10                  15

<210> SEQ ID NO 37
<211> LENGTH: 10
<212> TYPE: PRT
<213> ORGANISM: Artificial
<220> FEATURE:
<223> OTHER INFORMATION: AT 46 heavy chain CDR3

<400> SEQUENCE: 37

Cys Gly Arg Ala Gly Gln Ile Phe Asp Asp
1               5                   10

<210> SEQ ID NO 38
<211> LENGTH: 16
<212> TYPE: PRT
<213> ORGANISM: Artificial
<220> FEATURE:
<223> OTHER INFORMATION: AT32 heavy chain CDR3

<400> SEQUENCE: 38

Glu Ala Arg Tyr Cys Asp Asn Ser Arg Cys Ser Pro Asn Phe Asp His
1               5                   10                  15

<210> SEQ ID NO 39
<211> LENGTH: 14
<212> TYPE: PRT
<213> ORGANISM: Artificial
<220> FEATURE:
<223> OTHER INFORMATION: AT33 heavy chain CDR3

<400> SEQUENCE: 39

Asp Ala Glu Trp Ala Ala Gly Ser Asp Tyr Phe Phe Asp Tyr
1               5                   10

<210> SEQ ID NO 40
<211> LENGTH: 17
<212> TYPE: PRT
<213> ORGANISM: Artificial
<220> FEATURE:
<223> OTHER INFORMATION: AT34  heavy chain CDR3

<400> SEQUENCE: 40

Gln Gly Ala Lys Gly Gly His Glu Leu Ser Phe Tyr Cys Ala Leu Asp
1               5                   10                  15
Val
```

<210> SEQ ID NO 41
<211> LENGTH: 14
<212> TYPE: PRT
<213> ORGANISM: Artificial
<220> FEATURE:
<223> OTHER INFORMATION: AT 35 heavy chain CDR3

<400> SEQUENCE: 41

Glu Val Phe Val Thr Gln Val Glu Pro Ala Gln Trp Gly Phe
1               5                   10

<210> SEQ ID NO 42
<211> LENGTH: 13
<212> TYPE: PRT
<213> ORGANISM: Artificial
<220> FEATURE:
<223> OTHER INFORMATION: AT36 heavy chain CDR3

<400> SEQUENCE: 42

Asp Arg Val Gln Gln Gly Glu Gly Asn Phe Phe Asp His
1               5                   10

<210> SEQ ID NO 43
<211> LENGTH: 16
<212> TYPE: PRT
<213> ORGANISM: Artificial
<220> FEATURE:
<223> OTHER INFORMATION: AT 37 heavy chain CDR3

<400> SEQUENCE: 43

Gly Ala Tyr Gly Ser Gly Thr Tyr Tyr Ser Ala Asp Ala Leu Asp Ile
1               5                   10                  15

<210> SEQ ID NO 44
<211> LENGTH: 6
<212> TYPE: PRT
<213> ORGANISM: Artificial
<220> FEATURE:
<223> OTHER INFORMATION: AT39  heavy chain CDR3

<400> SEQUENCE: 44

Gly Arg Ile Phe Asp Ile
1               5

<210> SEQ ID NO 45
<211> LENGTH: 17
<212> TYPE: PRT
<213> ORGANISM: Artificial
<220> FEATURE:
<223> OTHER INFORMATION: AT40  heavy chain CDR3

<400> SEQUENCE: 45

Gly Arg Ala Leu Asp Asp Phe Ala Asp Tyr Gly Gly Tyr Tyr Phe Asp
1               5                   10                  15

Tyr

<210> SEQ ID NO 46
<211> LENGTH: 9
<212> TYPE: PRT
<213> ORGANISM: Artificial
<220> FEATURE:
<223> OTHER INFORMATION: AT 42 heavy chain CDR3

<400> SEQUENCE: 46

His Trp Ala Gly Leu Tyr Phe Asp Ser

<210> SEQ ID NO 47
<211> LENGTH: 15
<212> TYPE: PRT
<213> ORGANISM: Artificial
<220> FEATURE:
<223> OTHER INFORMATION: AT 43 heavy chain CDR3

<400> SEQUENCE: 47

His Gly Ser Gly Asn Tyr Tyr Gly Glu Ala Asn Tyr Phe Asp His
1               5                   10                  15

<210> SEQ ID NO 48
<211> LENGTH: 14
<212> TYPE: PRT
<213> ORGANISM: Artificial
<220> FEATURE:
<223> OTHER INFORMATION: AT 44 heavy chain CDR3

<400> SEQUENCE: 48

Asp Leu Tyr Asp Leu Ser Thr Gly Pro Phe Trp Phe Asp Pro
1               5                   10

<210> SEQ ID NO 49
<211> LENGTH: 12
<212> TYPE: PRT
<213> ORGANISM: Artificial
<220> FEATURE:
<223> OTHER INFORMATION: AT45  heavy chain CDR3

<400> SEQUENCE: 49

Val Ala Gly Gly Tyr Phe Asp Ser Ala Thr Arg Gly
1               5                   10

<210> SEQ ID NO 50
<211> LENGTH: 14
<212> TYPE: PRT
<213> ORGANISM: Artificial
<220> FEATURE:
<223> OTHER INFORMATION: AT47 heavy chain CDR3

<400> SEQUENCE: 50

Gly Phe His Tyr His Ser Ala Asp Gln Arg Ile Phe Asp Pro
1               5                   10

<210> SEQ ID NO 51
<211> LENGTH: 15
<212> TYPE: PRT
<213> ORGANISM: Artificial
<220> FEATURE:
<223> OTHER INFORMATION: AT49  heavy chain CDR3

<400> SEQUENCE: 51

Phe Leu Trp Phe Gly Asp Gln Thr Ser Asp Asp Gly Phe Asp Val
1               5                   10                  15

<210> SEQ ID NO 52
<211> LENGTH: 18
<212> TYPE: PRT
<213> ORGANISM: Artificial
<220> FEATURE:
<223> OTHER INFORMATION: AT50  heavy chain CDR3

<400> SEQUENCE: 52

Gly Gly Ala Gln Glu Met Val Arg Ile His Tyr Tyr Tyr Gly Met
1               5                   10                  15

Asp Val

<210> SEQ ID NO 53
<211> LENGTH: 18
<212> TYPE: PRT
<213> ORGANISM: Artificial
<220> FEATURE:
<223> OTHER INFORMATION: AT51  heavy chain CDR3

<400> SEQUENCE: 53

Pro Ala Thr Ser Tyr Asp Asp Leu Arg Ser Gly Tyr Leu Asn Tyr Cys
1               5                   10                  15

Asp Tyr

<210> SEQ ID NO 54
<211> LENGTH: 15
<212> TYPE: PRT
<213> ORGANISM: Artificial
<220> FEATURE:
<223> OTHER INFORMATION: AM22 heavy chain CDR3

<400> SEQUENCE: 54

Leu Gly Val Thr Val Thr Glu Ala Gly Leu Gly Ile Asp Asp Tyr
1               5                   10                  15

<210> SEQ ID NO 55
<211> LENGTH: 12
<212> TYPE: PRT
<213> ORGANISM: Artificial
<220> FEATURE:
<223> OTHER INFORMATION: AT46  light chain CDR1

<400> SEQUENCE: 55

Thr Leu Ser Ser Gly His Arg Asn Tyr Ala Ile Ala
1               5                   10

<210> SEQ ID NO 56
<211> LENGTH: 17
<212> TYPE: PRT
<213> ORGANISM: Artificial
<220> FEATURE:
<223> OTHER INFORMATION: AT32  light chain CDR1

<400> SEQUENCE: 56

Lys Ser Ser Gln Ser Val Leu Tyr Asp Ser Asn Asn Lys Asn Tyr Leu
1               5                   10                  15

Ala

<210> SEQ ID NO 57
<211> LENGTH: 11
<212> TYPE: PRT
<213> ORGANISM: Artificial
<220> FEATURE:
<223> OTHER INFORMATION: AT33 light chain CDR1

<400> SEQUENCE: 57

Ser Ala Asp Ala Phe Ser Asp Gln Tyr Ala Tyr
1               5                   10

<210> SEQ ID NO 58
<211> LENGTH: 11
<212> TYPE: PRT
<213> ORGANISM: Artificial
<220> FEATURE:
<223> OTHER INFORMATION: AT34 light chain CDR1

```
<400> SEQUENCE: 58

Arg Ala Ser Gln Gly Ile Gly Ser Trp Leu Ala
1               5                   10

<210> SEQ ID NO 59
<211> LENGTH: 11
<212> TYPE: PRT
<213> ORGANISM: Artificial
<220> FEATURE:
<223> OTHER INFORMATION: AT35  light chain CDR1

<400> SEQUENCE: 59

Arg Ala Ser Gln Ser Ile Asp Asn Tyr Leu Asn
1               5                   10

<210> SEQ ID NO 60
<211> LENGTH: 17
<212> TYPE: PRT
<213> ORGANISM: Artificial
<220> FEATURE:
<223> OTHER INFORMATION: AT36  light chain CDR1

<400> SEQUENCE: 60

Lys Ser Ser Gln Ser Leu Leu His Ser Ser Asn Asn Lys Ile Tyr Leu
1               5                   10                  15

Ala

<210> SEQ ID NO 61
<211> LENGTH: 12
<212> TYPE: PRT
<213> ORGANISM: Artificial
<220> FEATURE:
<223> OTHER INFORMATION: AT37  light chain CDR1

<400> SEQUENCE: 61

Arg Ala Ser Gln Ser Val Ser Ala Ser Asn Leu Ala
1               5                   10

<210> SEQ ID NO 62
<211> LENGTH: 11
<212> TYPE: PRT
<213> ORGANISM: Artificial
<220> FEATURE:
<223> OTHER INFORMATION: AT39  light chain CDR1

<400> SEQUENCE: 62

Gln Ala Ser Gln Asp Ile Ser Asn Phe Leu Asn
1               5                   10

<210> SEQ ID NO 63
<211> LENGTH: 11
<212> TYPE: PRT
<213> ORGANISM: Artificial
<220> FEATURE:
<223> OTHER INFORMATION: AT40  light chain CDR1

<400> SEQUENCE: 63

Arg Ala Ser Gln Gly Ile Ser Thr Trp Leu Ala
1               5                   10

<210> SEQ ID NO 64
<211> LENGTH: 12
<212> TYPE: PRT
<213> ORGANISM: Artificial
<220> FEATURE:
```

<223> OTHER INFORMATION: AT42 light chain CDR1

<400> SEQUENCE: 64

Arg Ala Ser Gln Thr Val Ser Ser Ser His Leu Ala
1               5                   10

<210> SEQ ID NO 65
<211> LENGTH: 12
<212> TYPE: PRT
<213> ORGANISM: Artificial
<220> FEATURE:
<223> OTHER INFORMATION: AT43 light chain CDR1

<400> SEQUENCE: 65

Arg Ala Ser Glu Ser Val Ser Arg Asn Tyr Leu Ala
1               5                   10

<210> SEQ ID NO 66
<211> LENGTH: 11
<212> TYPE: PRT
<213> ORGANISM: Artificial
<220> FEATURE:
<223> OTHER INFORMATION: AT44 light chain CDR1

<400> SEQUENCE: 66

Arg Ala Ser Gln Ser Val Ser Thr Lys Val Val
1               5                   10

<210> SEQ ID NO 67
<211> LENGTH: 16
<212> TYPE: PRT
<213> ORGANISM: Artificial
<220> FEATURE:
<223> OTHER INFORMATION: AT45 light chain CDR1

<400> SEQUENCE: 67

Arg Ser Ser Gln Ser Leu Leu His Ser Asn Gly Tyr Asn Tyr Leu Asp
1               5                   10                  15

<210> SEQ ID NO 68
<211> LENGTH: 11
<212> TYPE: PRT
<213> ORGANISM: Artificial
<220> FEATURE:
<223> OTHER INFORMATION: AT47 light chain CDR1

<400> SEQUENCE: 68

Arg Ala Ser Glu Ser Ile Ser Thr Trp Leu Ala
1               5                   10

<210> SEQ ID NO 69
<211> LENGTH: 16
<212> TYPE: PRT
<213> ORGANISM: Artificial
<220> FEATURE:
<223> OTHER INFORMATION: AT49 light chain CDR1

<400> SEQUENCE: 69

Arg Ser Ser Gln Ser Leu Leu His Gly Asn Gly Tyr Lys Tyr Leu His
1               5                   10                  15

<210> SEQ ID NO 70
<211> LENGTH: 11
<212> TYPE: PRT
<213> ORGANISM: Artificial
<220> FEATURE:
<223> OTHER INFORMATION: AT50 light chain CDR1

```
<400> SEQUENCE: 70

Arg Ala Ser Gln Val Ile Ser Ser Tyr Leu Ala
1               5                   10

<210> SEQ ID NO 71
<211> LENGTH: 11
<212> TYPE: PRT
<213> ORGANISM: Artificial
<220> FEATURE:
<223> OTHER INFORMATION: AT51  light chain CDR1

<400> SEQUENCE: 71

Arg Ala Ser Gln Gly Ile Thr Ser Tyr Leu Ala
1               5                   10

<210> SEQ ID NO 72
<211> LENGTH: 12
<212> TYPE: PRT
<213> ORGANISM: Artificial
<220> FEATURE:
<223> OTHER INFORMATION: AM22  light chain CDR1

<400> SEQUENCE: 72

Arg Ala Ser Gln Ile Val Ser Arg Asn His Leu Ala
1               5                   10

<210> SEQ ID NO 73
<211> LENGTH: 9
<212> TYPE: PRT
<213> ORGANISM: Artificial
<220> FEATURE:
<223> OTHER INFORMATION: AT46 Light chain CDR2

<400> SEQUENCE: 73

Thr Asn Gly Ser His Tyr Pro Gly Asp
1               5

<210> SEQ ID NO 74
<211> LENGTH: 7
<212> TYPE: PRT
<213> ORGANISM: Artificial
<220> FEATURE:
<223> OTHER INFORMATION: AT32 Light chain CDR2

<400> SEQUENCE: 74

Trp Ala Ser Thr Arg Glu Ser
1               5

<210> SEQ ID NO 75
<211> LENGTH: 7
<212> TYPE: PRT
<213> ORGANISM: Artificial
<220> FEATURE:
<223> OTHER INFORMATION: AT33 Light chain CDR2

<400> SEQUENCE: 75

Lys Asp Thr Glu Arg Pro Ser
1               5

<210> SEQ ID NO 76
<211> LENGTH: 7
<212> TYPE: PRT
<213> ORGANISM: Artificial
<220> FEATURE:
<223> OTHER INFORMATION: AT34 Light chain CDR2
```

```
<400> SEQUENCE: 76

Asn Ala Ser Gly Leu Glu Ser
1               5

<210> SEQ ID NO 77
<211> LENGTH: 7
<212> TYPE: PRT
<213> ORGANISM: Artificial
<220> FEATURE:
<223> OTHER INFORMATION: AT35 Light chain CDR2

<400> SEQUENCE: 77

Leu Ala Ser Thr Leu Gln Ser
1               5

<210> SEQ ID NO 78
<211> LENGTH: 7
<212> TYPE: PRT
<213> ORGANISM: Artificial
<220> FEATURE:
<223> OTHER INFORMATION: AT36 Light chain CDR2

<400> SEQUENCE: 78

Trp Ala Ser Thr Arg Glu Ser
1               5

<210> SEQ ID NO 79
<211> LENGTH: 7
<212> TYPE: PRT
<213> ORGANISM: Artificial
<220> FEATURE:
<223> OTHER INFORMATION: AT37 Light chain CDR2

<400> SEQUENCE: 79

Gly Ala Ser Arg Thr Ala Thr
1               5

<210> SEQ ID NO 80
<211> LENGTH: 7
<212> TYPE: PRT
<213> ORGANISM: Artificial
<220> FEATURE:
<223> OTHER INFORMATION: AT39 Light chain CDR2

<400> SEQUENCE: 80

Asp Ala Ser Lys Leu Gln Thr
1               5

<210> SEQ ID NO 81
<211> LENGTH: 7
<212> TYPE: PRT
<213> ORGANISM: Artificial
<220> FEATURE:
<223> OTHER INFORMATION: AT40 Light chain CDR2

<400> SEQUENCE: 81

Ser Ala Ser Arg Leu Gln Ser
1               5

<210> SEQ ID NO 82
<211> LENGTH: 7
<212> TYPE: PRT
<213> ORGANISM: Artificial
<220> FEATURE:
<223> OTHER INFORMATION: AT42 Light chain CDR2

<400> SEQUENCE: 82
```

```
Gly Ser Ser Arg Ala Thr
1               5

<210> SEQ ID NO 83
<211> LENGTH: 7
<212> TYPE: PRT
<213> ORGANISM: Artificial
<220> FEATURE:
<223> OTHER INFORMATION: AT43 Light chain CDR2

<400> SEQUENCE: 83

Gly Ala Ser Ser Arg Ala Ile
1               5

<210> SEQ ID NO 84
<211> LENGTH: 7
<212> TYPE: PRT
<213> ORGANISM: Artificial
<220> FEATURE:
<223> OTHER INFORMATION: AT44 Light chain CDR2

<400> SEQUENCE: 84

Gly Ala Ser Thr Arg Ala Thr
1               5

<210> SEQ ID NO 85
<211> LENGTH: 6
<212> TYPE: PRT
<213> ORGANISM: Artificial
<220> FEATURE:
<223> OTHER INFORMATION: AT45 Light chain CDR2

<400> SEQUENCE: 85

Gly Ser Asn Arg Ala Pro
1               5

<210> SEQ ID NO 86
<211> LENGTH: 7
<212> TYPE: PRT
<213> ORGANISM: Artificial
<220> FEATURE:
<223> OTHER INFORMATION: AT47 Light chain CDR2

<400> SEQUENCE: 86

Lys Ala Ser Ser Leu Glu Ser
1               5

<210> SEQ ID NO 87
<211> LENGTH: 7
<212> TYPE: PRT
<213> ORGANISM: Artificial
<220> FEATURE:
<223> OTHER INFORMATION: AT49 Light chain CDR2

<400> SEQUENCE: 87

Leu Gly Ser Asn Arg Ala Ser
1               5

<210> SEQ ID NO 88
<211> LENGTH: 7
<212> TYPE: PRT
<213> ORGANISM: Artificial
<220> FEATURE:
<223> OTHER INFORMATION: AT50 Light chain CDR2

<400> SEQUENCE: 88
```

Gly Ala Ser Thr Leu Gln Thr
1               5

<210> SEQ ID NO 89
<211> LENGTH: 7
<212> TYPE: PRT
<213> ORGANISM: Artificial
<220> FEATURE:
<223> OTHER INFORMATION: AT51 Light chain CDR2

<400> SEQUENCE: 89

Ala Ala Ser Thr Leu Gln Ser
1               5

<210> SEQ ID NO 90
<211> LENGTH: 7
<212> TYPE: PRT
<213> ORGANISM: Artificial
<220> FEATURE:
<223> OTHER INFORMATION: AM22 Light chain CDR2

<400> SEQUENCE: 90

Gly Ala Ser Ser Arg Ala Thr
1               5

<210> SEQ ID NO 91
<211> LENGTH: 7
<212> TYPE: PRT
<213> ORGANISM: Artificial
<220> FEATURE:
<223> OTHER INFORMATION: AT46 Light chain CDR3

<400> SEQUENCE: 91

Gln Thr Trp Gly Ala Gly Ile
1               5

<210> SEQ ID NO 92
<211> LENGTH: 7
<212> TYPE: PRT
<213> ORGANISM: Artificial
<220> FEATURE:
<223> OTHER INFORMATION: AT32 Light chain CDR3

<400> SEQUENCE: 92

Gln Gln Tyr Tyr Asp Pro Leu
1               5

<210> SEQ ID NO 93
<211> LENGTH: 9
<212> TYPE: PRT
<213> ORGANISM: Artificial
<220> FEATURE:
<223> OTHER INFORMATION: AT33 Light chain CDR3

<400> SEQUENCE: 93

Gln Ser Thr Asp Thr Ser Gly Pro Leu
1               5

<210> SEQ ID NO 94
<211> LENGTH: 7
<212> TYPE: PRT
<213> ORGANISM: Artificial
<220> FEATURE:
<223> OTHER INFORMATION: AT34 Light chain CDR3

<400> SEQUENCE: 94

Gln Gln Tyr Asn Ser His Thr

```
1               5

<210> SEQ ID NO 95
<211> LENGTH: 7
<212> TYPE: PRT
<213> ORGANISM: Artificial
<220> FEATURE:
<223> OTHER INFORMATION: AT35 Light chain CDR3

<400> SEQUENCE: 95

Gln Gln Ser His Ser Ser Pro
1               5

<210> SEQ ID NO 96
<211> LENGTH: 8
<212> TYPE: PRT
<213> ORGANISM: Artificial
<220> FEATURE:
<223> OTHER INFORMATION: AT36 Light chain CDR3

<400> SEQUENCE: 96

Gln Gln Tyr Tyr Thr Thr His Pro
1               5

<210> SEQ ID NO 97
<211> LENGTH: 7
<212> TYPE: PRT
<213> ORGANISM: Artificial
<220> FEATURE:
<223> OTHER INFORMATION: AT37 Light chain CDR3

<400> SEQUENCE: 97

Gln Gln Tyr Gly Ser Ser Pro
1               5

<210> SEQ ID NO 98
<211> LENGTH: 7
<212> TYPE: PRT
<213> ORGANISM: Artificial
<220> FEATURE:
<223> OTHER INFORMATION: AT39 Light chain CDR3

<400> SEQUENCE: 98

Gln Lys Phe Asp Asn Leu Leu
1               5

<210> SEQ ID NO 99
<211> LENGTH: 7
<212> TYPE: PRT
<213> ORGANISM: Artificial
<220> FEATURE:
<223> OTHER INFORMATION: AT40 Light chain CDR3

<400> SEQUENCE: 99

Gln Gln Ala Asn Thr Phe Pro
1               5

<210> SEQ ID NO 100
<211> LENGTH: 7
<212> TYPE: PRT
<213> ORGANISM: Artificial
<220> FEATURE:
<223> OTHER INFORMATION: AT42 Light chain CDR3

<400> SEQUENCE: 100

Gln Tyr Tyr Gly Asp Ser Pro
1               5
```

<210> SEQ ID NO 101
<211> LENGTH: 7
<212> TYPE: PRT
<213> ORGANISM: Artificial
<220> FEATURE:
<223> OTHER INFORMATION: AT43 Light chain CDR3

<400> SEQUENCE: 101

Gln Gln Tyr Thr Ile Phe Pro
1               5

<210> SEQ ID NO 102
<211> LENGTH: 7
<212> TYPE: PRT
<213> ORGANISM: Artificial
<220> FEATURE:
<223> OTHER INFORMATION: AT44 Light chain CDR3

<400> SEQUENCE: 102

Gln Gln Tyr Asn Lys Trp Pro
1               5

<210> SEQ ID NO 103
<211> LENGTH: 7
<212> TYPE: PRT
<213> ORGANISM: Artificial
<220> FEATURE:
<223> OTHER INFORMATION: AT45 Light chain CDR3

<400> SEQUENCE: 103

Met Gln Ala Leu Gln Thr Pro
1               5

<210> SEQ ID NO 104
<211> LENGTH: 7
<212> TYPE: PRT
<213> ORGANISM: Artificial
<220> FEATURE:
<223> OTHER INFORMATION: AT47 Light chain CDR3

<400> SEQUENCE: 104

Gln Gln Tyr Lys Ser Tyr Pro
1               5

<210> SEQ ID NO 105
<211> LENGTH: 7
<212> TYPE: PRT
<213> ORGANISM: Artificial
<220> FEATURE:
<223> OTHER INFORMATION: AT49 Light chain CDR3

<400> SEQUENCE: 105

Met Gln Ala Leu Gln Ser Pro
1               5

<210> SEQ ID NO 106
<211> LENGTH: 7
<212> TYPE: PRT
<213> ORGANISM: Artificial
<220> FEATURE:
<223> OTHER INFORMATION: AT50 Light chain CDR3

<400> SEQUENCE: 106

Gln Gln Leu Asn Thr Tyr Pro
1               5

<210> SEQ ID NO 107
<211> LENGTH: 7
<212> TYPE: PRT
<213> ORGANISM: Artificial
<220> FEATURE:
<223> OTHER INFORMATION: AT51 Light chain CDR3

<400> SEQUENCE: 107

Gln Gln Phe His Thr Tyr Pro
1               5

<210> SEQ ID NO 108
<211> LENGTH: 7
<212> TYPE: PRT
<213> ORGANISM: Artificial
<220> FEATURE:
<223> OTHER INFORMATION: AM22 Light chain CDR3

<400> SEQUENCE: 108

Leu Ser Ser Asp Ser Ser Ile
1               5

<210> SEQ ID NO 109
<211> LENGTH: 119
<212> TYPE: PRT
<213> ORGANISM: Artificial
<220> FEATURE:
<223> OTHER INFORMATION: AT46 Heavy chain

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Arg Gly Leu Glu Trp Val
        35                  40                  45

Ser Ser Ile Thr Gly Ser Gly Ala Thr Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Arg Leu Arg Ala Glu Asp Thr Ala Ile Tyr Tyr Cys
                85                  90                  95

Ala Asn Cys Gly Arg Ala Gly Gln Ile Phe Asp Asp Trp Gly Gln Gly
            100                 105                 110

Thr Leu Val Thr Val Ser Ser
        115

<210> SEQ ID NO 110
<211> LENGTH: 125
<212> TYPE: PRT
<213> ORGANISM: Artificial
<220> FEATURE:
<223> OTHER INFORMATION: AT32 Heavy chain

<400> SEQUENCE: 110

Gln Val Gln Leu Val Gln Ser Gly Ala Glu Met Lys Lys Pro Gly Ala
1               5                   10                  15

Ser Val Lys Val Ser Cys Gln Val Ala Gly Tyr Thr Leu Thr Glu Leu
            20                  25                  30

Ser Ile His Trp Val Arg Gln Thr Pro Gly Asn Gly Leu Glu Trp Met
        35                  40                  45

Gly Gly Phe Glu Pro Glu Asp Gly Glu Tyr Ile Tyr Pro Gln Lys Ser
        50                  55                  60

Gln Gly Arg Val Thr Met Thr Glu Asp Thr Ser Thr Gly Thr Ala Tyr
 65                  70                  75                  80

Met Glu Leu Arg Ser Leu Arg Ser Asp Asp Thr Ala Val Tyr Tyr Cys
                 85                  90                  95

Ala Ala Glu Ala Arg Tyr Cys Asp Asn Ser Arg Cys Ser Pro Asn Phe
            100                 105                 110

Asp His Trp Gly Gln Gly Thr Leu Val Ala Val Ser Ser
            115                 120                 125

<210> SEQ ID NO 111
<211> LENGTH: 123
<212> TYPE: PRT
<213> ORGANISM: Artificial
<220> FEATURE:
<223> OTHER INFORMATION: AT33 Heavy chain

<400> SEQUENCE: 111

Gln Val Gln Leu Val Gln Ser Gly Ala Glu Val Lys Lys Pro Gly Ser
 1               5                  10                  15

Ser Val Lys Val Ser Cys Lys Ala Ser Gly Asp Ser Phe Asn Ser Leu
             20                  25                  30

Ala Ile Ser Trp Val Arg Gln Ala Pro Gly Gln Gly Leu Glu Trp Met
         35                  40                  45

Gly Gly Ile Ile Pro Lys Phe Asn Arg Arg Asp Tyr Ala Gln Lys Phe
     50                  55                  60

Gln Gly Arg Val Thr Ile Thr Ala Asp Asp Ser Ala Ser Thr Ala Tyr
 65                  70                  75                  80

Ile Glu Leu Ser Ser Leu Thr Ser Asp Asp Thr Ala Leu Tyr Tyr Cys
                 85                  90                  95

Ala Arg Asp Ala Glu Trp Ala Ala Gly Ser Tyr Phe Phe Asp Tyr
            100                 105                 110

Trp Gly Gln Gly Thr Leu Val Ile Val Ser Ser
            115                 120

<210> SEQ ID NO 112
<211> LENGTH: 126
<212> TYPE: PRT
<213> ORGANISM: Artificial
<220> FEATURE:
<223> OTHER INFORMATION: AT34 Heavy chain

<400> SEQUENCE: 112

Gln Val Gln Leu Met Glu Ser Gly Gly Val Val Gln Pro Gly Lys
 1               5                  10                  15

Ser Leu Arg Leu Ser Cys Ala Ala Ser Gly Phe Thr Phe Ser His Tyr
             20                  25                  30

Gly Met His Trp Val Arg Gln Ala Pro Gly Lys Gly Leu Glu Trp Val
         35                  40                  45

Ala Val Ile Ser Tyr Asp Gly Asp Lys Lys Tyr Tyr Ala Asp Ser Val
     50                  55                  60

Lys Gly Arg Phe Thr Ile Ser Arg Asp Asn Ser Lys Asn Thr Leu His
 65                  70                  75                  80

Leu His Met Asn Ser Leu Arg His Glu Asp Thr Ala Val Tyr Phe Cys
                 85                  90                  95

Ala Ser Gln Gly Ala Lys Gly Gly His Glu Leu Ser Phe Tyr Cys Ala
            100                 105                 110

```
Leu Asp Val Trp Gly Gln Gly Thr Thr Val Ala Val Ser Ser
        115                 120                 125

<210> SEQ ID NO 113
<211> LENGTH: 123
<212> TYPE: PRT
<213> ORGANISM: Artificial
<220> FEATURE:
<223> OTHER INFORMATION: AT35 Heavy chain

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Trp Val Ser Trp Val Arg Gln Thr Pro Gly Lys Gly Leu Glu Trp Val
        35                  40                  45

Ala Arg Phe Thr Ile Ser Asn Ile Asn Gln Asp Gly Ser Glu Lys Ser
    50                  55                  60

Tyr Val Asp Ser Val Glu Gly Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Glu Val Phe Val Thr Gly Val Glu Pro Ala Gly Trp Gly Phe
            100                 105                 110

Trp Gly Gln Gly Thr Pro Val Ile Val Ser Ser
        115                 120

<210> SEQ ID NO 114
<211> LENGTH: 123
<212> TYPE: PRT
<213> ORGANISM: Artificial
<220> FEATURE:
<223> OTHER INFORMATION: AT36 Heavy chain

<400> SEQUENCE: 114

Gln Val Gln Val Val Gln Ser Gly Ala Glu Val Lys Lys Pro Gly Ala
1               5                   10                  15

Ser Val Lys Val Ser Cys Lys Thr Ser Gly Tyr Asn Phe Ile Asp His
            20                  25                  30

Ser Val Ser Trp Val Arg Gln Ala Pro Gly Gln Gly Leu Glu Trp Met
        35                  40                  45

Gly Trp Ile Ser Pro Tyr Asn His Arg Thr Val Tyr Ala Glu Lys Phe
    50                  55                  60

Gln Gly Arg Val Thr Met Thr Thr Asp Thr Ser Thr Arg Thr Val Ser
65                  70                  75                  80

Met Glu Leu Arg Arg Leu Thr Ser Asp Thr Ala Val Tyr Phe Cys
                85                  90                  95

Ala Arg Asp Arg Val Gln Gln Gly Glu Gly Asn Phe Phe Asp His Trp
            100                 105                 110

Gly Gln Gly Thr Pro Val Thr Val Thr Ser Ala
        115                 120

<210> SEQ ID NO 115
<211> LENGTH: 126
<212> TYPE: PRT
<213> ORGANISM: Artificial
<220> FEATURE:
<223> OTHER INFORMATION: AT37 Heavy chain
```

<400> SEQUENCE: 115

Gln Leu Gln Leu Gln Glu Ser Gly Ser Arg Leu Val Lys Pro Ser Gln
1               5                   10                  15

Thr Leu Ser Leu Thr Cys Gly Val Ser Gly Gly Ser Ile Ser Ser Gly
            20                  25                  30

Gly Tyr Ser Trp Asn Trp Ile Arg Gln Pro Pro Gly Lys Gly Leu Glu
        35                  40                  45

Trp Val Gly Tyr Ile Tyr Gln Asn Asp Ile Thr Tyr Tyr Asn Pro Ser
50                  55                  60

Leu Met Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Ala Tyr Gly Ser Gly Thr Tyr Tyr Ser Ala Asp Ala
            100                 105                 110

Leu Asp Ile Trp Gly Gln Gly Thr Met Val Thr Val Ser Ser
            115                 120                 125

<210> SEQ ID NO 116
<211> LENGTH: 115
<212> TYPE: PRT
<213> ORGANISM: Artificial
<220> FEATURE:
<223> OTHER INFORMATION: AT39 Heavy chain

<400> SEQUENCE: 116

Gln Val Gln Leu Val Gln Ser Gly Pro Glu Val Lys Lys Pro Gly Ala
1               5                   10                  15

Ser Val Arg Leu Ser Cys Thr Ala Ser Gly Asn Thr Phe Arg Thr Tyr
            20                  25                  30

Ala Val His Trp Val Arg Gln Ala Ser Gly Gln Arg Leu Glu Trp Met
        35                  40                  45

Gly Trp Ile Asn Pro Asp Asn Gly Asp Thr Lys Tyr Ser Gln Arg Phe
50                  55                  60

Gln Gly Arg Val Val Ile Thr Arg Asp Thr Ser Ala Arg Ile Ile Tyr
65                  70                  75                  80

Leu Asp Leu Ser Ser Leu Thr Ser Glu Asp Thr Ala Val Phe Tyr Cys
            85                  90                  95

Phe Ser Gly Arg Ile Phe Asp Ile Trp Gly Gln Gly Thr Thr Ile Thr
            100                 105                 110

Val Ser Ser
        115

<210> SEQ ID NO 117
<211> LENGTH: 126
<212> TYPE: PRT
<213> ORGANISM: Artificial
<220> FEATURE:
<223> OTHER INFORMATION: AT40 Heavy chain

<400> SEQUENCE: 117

Gln Val Gln Leu Val Glu Ser Gly Gly Val Gln Pro Gly Met
1               5                   10                  15

Ser His Arg Leu Ser Cys Ala Ala Ser Thr Leu Ile Phe Asp Arg His
            20                  25                  30

Ala Leu His Trp Val Arg Gln Ala Pro Gly Ala Gly Leu Glu Trp Val
        35                  40                  45

Ala Ile Leu Ser Tyr Asp Gly Thr Thr Asp Tyr Tyr Ala Asp Ser Val
            50                  55                  60

Lys Gly Arg Phe Thr Val Ser Arg Asp Thr Ser Lys Asn Thr Val Phe
 65                  70                  75                  80

Leu Gln Met Asn Gly Leu Arg Pro Gln Asp Thr Ala Val Tyr Tyr Cys
                 85                  90                  95

Ala Arg Gly Arg Ala Leu Asp Asp Phe Ala Asp Tyr Gly Gly Tyr Tyr
            100                 105                 110

Phe Asp Tyr Trp Gly Gln Gly Ile Leu Val Thr Val Ser Ser
            115                 120                 125

<210> SEQ ID NO 118
<211> LENGTH: 119
<212> TYPE: PRT
<213> ORGANISM: Artificial
<220> FEATURE:
<223> OTHER INFORMATION: AT42 Heavy chain

<400> SEQUENCE: 118

Gln Val Gln Leu Gln Glu Ser Gly Pro Gly Leu Val Gln Pro Ser Glu
 1               5                  10                  15

Thr Leu Ser Leu Thr Cys Thr Val Ser Gly Asp Ser Ile Thr Ser Asn
                20                  25                  30

Val Tyr Tyr Trp Gly Trp Ile Arg Gln Pro Pro Gly Lys Gly Leu Glu
            35                  40                  45

Trp Ile Gly Ser Ile Phe His Ser Gly Ile Thr His Tyr Thr Pro Ser
        50                  55                  60

Leu Asn Ser Arg Val Thr Ile Ser Val Asp Thr Ser Lys Asn Gln Phe
 65                  70                  75                  80

Ser Leu Arg Leu Ser Ser Ala Thr Ala Ala Asp Thr Ala Val Tyr Tyr
                85                  90                  95

Cys Ala Arg His Trp Ala Gly Leu Tyr Phe Asp Ser Trp Gly Gln Gly
            100                 105                 110

Ala Leu Val Ala Val Ser Ser
        115

<210> SEQ ID NO 119
<211> LENGTH: 124
<212> TYPE: PRT
<213> ORGANISM: Artificial
<220> FEATURE:
<223> OTHER INFORMATION: AT43 Heavy chain

<400> SEQUENCE: 119

Gln Val Gln Val Val Gln Ser Gly Pro Glu Val Lys Lys Pro Gly Ala
 1               5                  10                  15

Ser Val Arg Val Ser Cys Lys Ala Ser Gly Tyr Thr Phe Thr Asn Tyr
                20                  25                  30

Gly Val Ser Trp Val Arg Gln Ala Pro Gly Gln Gly Leu Glu Trp Met
            35                  40                  45

Gly Trp Ile Ser Thr Tyr Asn Gly Asn Thr Trp Tyr Ser Gln Lys Phe
        50                  55                  60

Gln Ala Arg Val Thr Met Thr Thr Asp Thr Ser Thr Ser Thr Ala Tyr
 65                  70                  75                  80

Met Glu Val Arg Ser Leu Arg Ser Asp Asp Thr Ala Ile Tyr Tyr Cys
                85                  90                  95

Ala Cys His Gly Ser Gly Asn Tyr Tyr Gly Glu Ala Asn Tyr Phe Asp

```
                      100                 105                 110
His Trp Gly Gln Gly Thr Leu Val Thr Val Ser Ser
        115                 120

<210> SEQ ID NO 120
<211> LENGTH: 123
<212> TYPE: PRT
<213> ORGANISM: Artificial
<220> FEATURE:
<223> OTHER INFORMATION: AT44 Heavy chain

<400> SEQUENCE: 120

Gln Val Gln Leu Gln Ala Ser Gly Pro Gly Leu Val Lys Pro Ser Glu
1               5                   10                  15

Thr Leu Ser Leu Thr Cys Asn Val Ser Gly Tyr Ser Val Ser Ser Gly
            20                  25                  30

His Tyr Trp Ala Trp Val Arg Gln Ser Pro Gly Lys Gly Leu Glu Trp
        35                  40                  45

Ile Gly Gly Ile His His Ser Gly Ser Thr Tyr Thr Asn Pro Pro Leu
    50                  55                  60

Lys Ser Arg Val Ser Ile Ser Ile Asp Thr Ser Lys Asn Gln Phe Ser
65                  70                  75                  80

Leu Arg Leu Thr Ser Val Thr Ala Ala Asp Thr Ala Val Tyr Phe Cys
                85                  90                  95

Ala Arg Asp Leu Tyr Asp Leu Ser Thr Gly Pro Phe Trp Phe Asp Pro
            100                 105                 110

Trp Gly Gln Gly Thr Leu Val Thr Val Ser Ser
        115                 120

<210> SEQ ID NO 121
<211> LENGTH: 121
<212> TYPE: PRT
<213> ORGANISM: Artificial
<220> FEATURE:
<223> OTHER INFORMATION: AT45 Heavy chain

<400> SEQUENCE: 121

Gln Val His Leu Val Gln Ser Gly Ala Glu Val Lys Lys Pro Gly Ser
1               5                   10                  15

Ser Val Lys Val Ser Cys Lys Ala Ser Gly Gly Thr Phe Asn Gly His
            20                  25                  30

Ala Ile Ser Trp Ile Arg Gln Ala Pro Gly Gln Gly Leu Glu Trp Lys
        35                  40                  45

Gly Gly Ile Ile Pro Gly Leu Gly Thr Thr Arg Tyr Ala Arg Lys Phe
    50                  55                  60

Gln Asp Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Gly Gly Tyr Phe Asp Ser Ala Thr Arg Gly Trp Gly
            100                 105                 110

Gln Gly Thr Leu Val Thr Val Ser Ser
        115                 120

<210> SEQ ID NO 122
<211> LENGTH: 123
<212> TYPE: PRT
<213> ORGANISM: Artificial
<220> FEATURE:
```

<223> OTHER INFORMATION: AT47 Heavy chain

<400> SEQUENCE: 122

Gln Val Gln Leu Val Gln Ser Gly Gly Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Cys Trp Val Arg Gln Ala Pro Gly Gln Gly Leu Glu Trp Met
        35                  40                  45

Gly Trp Ile Ser Gly Tyr Asn Gly Asn Thr Tyr Tyr Ala Gln Asn Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Phe His Tyr His Ser Ala Asp Gln Arg Ile Phe Asp Pro
            100                 105                 110

Trp Gly Gln Gly Thr Leu Val Thr Val Ser Ser
            115                 120

<210> SEQ ID NO 123
<211> LENGTH: 124
<212> TYPE: PRT
<213> ORGANISM: Artificial
<220> FEATURE:
<223> OTHER INFORMATION: AT49 Heavy chain

<400> SEQUENCE: 123

Gln Val Leu Leu Val Gln Ser Gly Ala Glu Ile Lys Lys Pro Gly Ser
1               5                   10                  15

Ser Val Lys Ile Ser Cys Lys Ala Ser Gly Gly Thr Phe Ser Ser Leu
            20                  25                  30

Ala Leu Asn Trp Val Arg Gln Ala Pro Gly Gln Gly Leu Gln Trp Met
        35                  40                  45

Gly Gly Ile Ile Pro Leu Phe Gly Thr Gln Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Gly Leu Arg Pro Glu Asp Thr Ala Val Tyr Tyr Cys
                85                  90                  95

Ala Leu Phe Leu Trp Phe Gly Asp Gln Thr Ser Asp Asp Gly Phe Asp
            100                 105                 110

Val Trp Gly Gln Gly Thr Val Val Thr Val Ser Ser
            115                 120

<210> SEQ ID NO 124
<211> LENGTH: 127
<212> TYPE: PRT
<213> ORGANISM: Artificial
<220> FEATURE:
<223> OTHER INFORMATION: AT50 Heavy chain

<400> SEQUENCE: 124

Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Ile Ser Trp Val Arg Gln Ala Pro Gly Gln Gly Leu Glu Trp Met

```
                35                  40                  45

Gly Trp Ile Ser Ala Tyr Asn Gly Asn Thr Tyr Tyr Arg Gln Glu Leu
 50                  55                  60

Gln Gly Arg Val Thr Met Thr Thr Asp Thr Ser Thr Ser Thr Ala Tyr
65                   70                  75                  80

Met Glu Leu Arg Ser Leu Arg Ser Asp Asp Thr Ala Val Tyr Tyr Cys
                 85                  90                  95

Ala Arg Gly Gly Ala Gln Glu Met Val Arg Ile His Tyr Tyr Tyr Tyr
            100                 105                 110

Gly Met Asp Val Trp Gly Gln Gly Thr Thr Val Thr Val Ser Ser
            115                 120                 125

<210> SEQ ID NO 125
<211> LENGTH: 127
<212> TYPE: PRT
<213> ORGANISM: Artificial
<220> FEATURE:
<223> OTHER INFORMATION: AT51 Heavy chain

<400> SEQUENCE: 125

Gln Val Gln Leu Val Gln Ser Gly Ala Glu Val Lys Lys Pro Gly Ala
1               5                   10                  15

Ser Met Thr Val Ser Cys Lys Ala Ser Gly Tyr Thr Phe Ser Lys Tyr
                20                  25                  30

Gly Ile Asn Trp Val Arg Gln Ala Pro Gly Gln Gly Leu Glu Trp Leu
            35                  40                  45

Gly Trp Ile Ser Ala Tyr Asn Gly Asn Thr Tyr Tyr Ala Gln Lys Phe
 50                  55                  60

Gln Gly Arg Val Thr Met Thr Thr Asp Thr Ala Thr Ser Thr Ala Tyr
65                   70                  75                  80

Met Asp Val Arg Asn Leu Arg Ser Asp Asp Thr Ala Met Tyr Tyr Cys
                 85                  90                  95

Ala Arg Pro Ala Thr Ser Tyr Asp Leu Arg Ser Gly Tyr Leu Asn
            100                 105                 110

Tyr Cys Asp Tyr Trp Gly Gln Gly Thr Leu Val Thr Val Ser Ser
            115                 120                 125

<210> SEQ ID NO 126
<211> LENGTH: 124
<212> TYPE: PRT
<213> ORGANISM: Artificial
<220> FEATURE:
<223> OTHER INFORMATION: AM22 Heavy chain

<400> SEQUENCE: 126

Gln Val Gln Leu Val Gln Ser Gly Ala Glu Val Lys Lys Pro Gly Ala
1               5                   10                  15

Thr Val Lys Val Ser Cys Lys Ile Ser Gly His Thr Leu Ile Lys Leu
                20                  25                  30

Ser Ile His Trp Val Arg Gln Ala Pro Gly Lys Gly Leu Glu Trp Met
            35                  40                  45

Gly Gly Tyr Glu Gly Glu Val Asp Glu Ile Phe Tyr Ala Gln Lys Phe
 50                  55                  60

Gln His Arg Leu Thr Val Ile Ala Asp Thr Ala Thr Asp Thr Val Tyr
65                   70                  75                  80

Met Glu Leu Gly Arg Leu Thr Ser Asp Asp Thr Ala Val Tyr Phe Cys
                 85                  90                  95
```

Gly Thr Leu Gly Val Thr Val Thr Glu Ala Gly Leu Gly Ile Asp Asp
            100                 105                 110

Tyr Trp Gly Gln Gly Thr Leu Val Thr Val Ser Ser
        115                 120

<210> SEQ ID NO 127
<211> LENGTH: 115
<212> TYPE: PRT
<213> ORGANISM: Artificial
<220> FEATURE:
<223> OTHER INFORMATION: AT46 Light chain

<400> SEQUENCE: 127

Gln Pro Val Leu Thr Gln Ser Pro Ser Ala Ser Ala Ser Leu Gly Ala
1               5                   10                  15

Ser Val Lys Leu Thr Cys Thr Leu Ser Ser Gly His Arg Asn Tyr Ala
            20                  25                  30

Ile Ala Trp His Gln Gln Arg Pro Glu Lys Gly Pro Arg Tyr Leu Met
        35                  40                  45

Lys Ile Tyr Thr Asn Gly Ser His Tyr Pro Gly Asp Gly Thr Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Ala Gly Ile Trp Val Phe Gly Gly Gly Thr Lys Leu Thr Val Leu Gly
            100                 105                 110

Gln Pro Lys
        115

<210> SEQ ID NO 128
<211> LENGTH: 116
<212> TYPE: PRT
<213> ORGANISM: Artificial
<220> FEATURE:
<223> OTHER INFORMATION: AT32 Light chain

<400> SEQUENCE: 128

Asp Ile Val Met Thr Gln Ser Pro Asp Ser Leu Ala Val Ser Leu Gly
1               5                   10                  15

Glu Arg Ala Thr Phe Ser Cys Lys Ser Ser Gln Ser Val Leu Tyr Asp
            20                  25                  30

Ser Asn Asn Lys Asn Tyr Leu Ala Trp Tyr Gln Gln Arg Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Tyr Tyr Asp Pro Leu Ile Thr Phe Gly Gln Gly Thr Arg Leu Glu Ile
            100                 105                 110

Lys Arg Thr Val
        115

<210> SEQ ID NO 129
<211> LENGTH: 110
<212> TYPE: PRT
<213> ORGANISM: Artificial

```
<220> FEATURE:
<223> OTHER INFORMATION: AT33 Light chain

<400> SEQUENCE: 129

Ser Tyr Glu Leu Thr Gln Pro Pro Ser Val Ser Val Ser Pro Gly Gln
1               5                   10                  15

Thr Ala Arg Ile Thr Cys Ser Ala Asp Ala Phe Ser Asp Gln Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Ile Ser Gly Ser
    50                  55                  60

Ser Ser Gly Thr Thr Ala Thr Leu Ser Ile Ser Gly Val Gln Ala Glu
65              70                  75                  80

Asp Glu Ala Asp Tyr Tyr Cys Gln Ser Thr Asp Thr Ser Gly Pro Leu
                85                  90                  95

Phe Gly Gly Gly Thr Lys Leu Thr Leu Leu Gly Gln Pro Lys
            100                 105                 110

<210> SEQ ID NO 130
<211> LENGTH: 110
<212> TYPE: PRT
<213> ORGANISM: Artificial
<220> FEATURE:
<223> OTHER INFORMATION: AT34 Light chain

<400> SEQUENCE: 130

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Gly Ile Gly Ser Trp
            20                  25                  30

Leu Ala Trp Tyr Gln Gln Lys Pro Gly Lys Ala Pro Lys Leu Leu Ile
        35                  40                  45

Tyr Asn Ala Ser Gly Leu Glu Ser Gly Val Pro Ser Gly Phe Ser Gly
    50                  55                  60

Ser Gly Ser Gly Thr Glu Phe Thr Leu Thr Ile Ser Ser Leu Gln Pro
65              70                  75                  80

Asp Asp Ser Ala Thr Tyr Tyr Cys Gln Gln Tyr Asn Ser His Thr Trp
                85                  90                  95

Thr Phe Gly Gln Gly Thr Lys Val Glu Phe Lys Arg Thr Val
            100                 105                 110

<210> SEQ ID NO 131
<211> LENGTH: 110
<212> TYPE: PRT
<213> ORGANISM: Artificial
<220> FEATURE:
<223> OTHER INFORMATION: AT35 Light chain

<400> SEQUENCE: 131

Ala Ile Gln Met Thr Gln Ser Pro Ser Ser Leu Ser Ala Ser Val Gly
1               5                   10                  15

Asp Arg Val Thr Ile Ser Cys Arg Ala Ser Gln Ser Ile Asp Asn Tyr
            20                  25                  30

Leu Asn Trp Tyr Gln Gln Lys Pro Gly Lys Ala Pro Lys Leu Leu Leu
        35                  40                  45

Phe Leu Ala Ser Thr Leu Gln Ser Gly Val Pro Ser Arg Phe Thr Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser His Ser Ser Pro Tyr
                 85                  90                  95

Ser Phe Gly Gln Gly Thr Lys Leu Glu Ile Lys Arg Thr Val
            100                 105                 110

<210> SEQ ID NO 132
<211> LENGTH: 116
<212> TYPE: PRT
<213> ORGANISM: Artificial
<220> FEATURE:
<223> OTHER INFORMATION: AT36 Light chain

<400> SEQUENCE: 132

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu His Ser
                 20                  25                  30

Ser Asn Asn Lys Ile Tyr Leu Ala Trp Tyr Gln Gln Lys Pro Gly Gln
             35                  40                  45

Pro Pro Lys Leu Leu Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Asn Ser Leu Gln Ala Glu Asp Val Ala Val Tyr Tyr Cys Gln Gln
                 85                  90                  95

Tyr Tyr Thr Thr His Pro Thr Phe Gly Gln Gly Thr Arg Leu Glu Ile
            100                 105                 110

Lys Arg Thr Val
        115

<210> SEQ ID NO 133
<211> LENGTH: 111
<212> TYPE: PRT
<213> ORGANISM: Artificial
<220> FEATURE:
<223> OTHER INFORMATION: AT37 Light chain

<400> SEQUENCE: 133

Lys Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ala Ser
                 20                  25                  30

Asn Leu Ala Trp Tyr Gln Gln Lys Pro Gly Gln Ala Pro Arg Leu Leu
             35                  40                  45

Ile Tyr Gly Ile Pro Asp Arg Phe Ser Gly Ser Gly Ser Gly Thr Asp
 50                  55                  60

Phe Thr Leu Ser Ile Ser Arg Leu Glu Pro Glu Asp Phe Ala Val Tyr
 65                  70                  75                  80

Tyr Cys Gly Ala Ser Arg Thr Ala Thr Gln Gln Tyr Gly Ser Ser Pro
                 85                  90                  95

Leu Thr Phe Gly Gly Gly Thr Lys Val Glu Ile Lys Arg Thr Val
            100                 105                 110

<210> SEQ ID NO 134
<211> LENGTH: 110
<212> TYPE: PRT
<213> ORGANISM: Artificial
```

```
<220> FEATURE:
<223> OTHER INFORMATION: AT39 Light chain

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Phe
            20                  25                  30

Leu Asn Trp Tyr Gln Gln Lys Pro Gly Gln Ala Pro Lys Leu Leu Ile
        35                  40                  45

Tyr Asp Ala Ser Lys Leu Gln Thr Gly Val Pro Ser Arg Phe Ser Gly
50                  55                  60

Ser Gly Ser Glu Thr Asp Phe Thr Phe Thr Ile Ser Ser Leu Gln Pro
65                  70                  75                  80

Glu Asp Val Ala Thr Tyr Tyr Cys Gln Lys Phe Asp Asn Leu Leu Leu
                85                  90                  95

Thr Phe Gly Gly Gly Thr Lys Val Glu Leu Lys Arg Thr Val
            100                 105                 110

<210> SEQ ID NO 135
<211> LENGTH: 110
<212> TYPE: PRT
<213> ORGANISM: Artificial
<220> FEATURE:
<223> OTHER INFORMATION: AT40 Light chain

<400> SEQUENCE: 135

Asp Ile Gln Met Thr Gln Ser Pro Ser Ser Val Ser Ala Ser Val Gly
1               5                   10                  15

Asp Lys Val Thr Ile Thr Cys Arg Ala Ser Gln Gly Ile Ser Thr Trp
            20                  25                  30

Leu Ala Trp Tyr Gln Gln Lys Pro Gly Lys Ala Pro Ala Leu Leu Ile
        35                  40                  45

Tyr Ser Ala Ser Arg Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Tyr Ala Thr Tyr Tyr Cys Gln Gln Ala Asn Thr Phe Pro Phe
                85                  90                  95

Thr Phe Gly Pro Gly Thr Lys Val Asp Ile Lys Arg Thr Val
            100                 105                 110

<210> SEQ ID NO 136
<211> LENGTH: 111
<212> TYPE: PRT
<213> ORGANISM: Artificial
<220> FEATURE:
<223> OTHER INFORMATION: AT42 Light chain

<400> SEQUENCE: 136

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Ser
            20                  25                  30

His Leu Ala Trp Tyr Gln Gln Lys Pro Gly Gln Ala Pro Arg Leu Leu
        35                  40                  45

Ile His Gly Ser Ser Ser Arg Ala Thr Gly Ile Pro Glu Arg Phe Ser
    50                  55                  60
```

```
Gly Ser Gly Ser Gly Pro Asp Phe Thr Leu Thr Ile Ser Arg Leu Lys
65                  70                  75                  80

Pro Glu Asp Phe Ala Val Tyr Tyr Cys Gln Tyr Tyr Gly Asp Ser Pro
                85                  90                  95

Gly Ser Phe Gly Glu Gly Thr Lys Val Glu Ile Lys Arg Thr Val
                100                 105                 110
```

<210> SEQ ID NO 137
<211> LENGTH: 111
<212> TYPE: PRT
<213> ORGANISM: Artificial
<220> FEATURE:
<223> OTHER INFORMATION: AT43 Light chain

<400> SEQUENCE: 137

```
Asp Ile Val Leu Thr Gln Ser Pro Gly Thr Leu Ser Leu Ser Pro Gly
1               5                   10                  15

Glu Gly Ala Thr Leu Ser Cys Arg Ala Ser Glu Ser Val Ser Arg Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Ile Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Cys Cys Gln Gln Tyr Thr Ile Phe Pro
                85                  90                  95

Leu Thr Phe Gly Gly Gly Thr Lys Val Glu Ile Lys Arg Thr Val
                100                 105                 110
```

<210> SEQ ID NO 138
<211> LENGTH: 111
<212> TYPE: PRT
<213> ORGANISM: Artificial
<220> FEATURE:
<223> OTHER INFORMATION: AT44 Light chain

<400> SEQUENCE: 138

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Thr Lys
                20                  25                  30

Val Val Trp Tyr Gln Gln Lys Phe Gly Gln Ala Pro Arg Leu Leu Ile
            35                  40                  45

Tyr Gly Ala Ser Thr Arg Ala Thr Gly Ile Pro Val Arg Phe Ser Gly
50                  55                  60

Ser Gly Ser Gly Thr Glu Phe Thr Leu Thr Ile Ser Ser Leu Gln Ser
65                  70                  75                  80

Glu Asp Leu Ala Val Tyr Phe Cys Gln Gln Tyr Asn Lys Trp Pro Met
                85                  90                  95

Tyr Thr Phe Gly Gln Gly Thr Lys Leu Glu Ile Lys Arg Thr Val
                100                 105                 110
```

<210> SEQ ID NO 139
<211> LENGTH: 114
<212> TYPE: PRT
<213> ORGANISM: Artificial
<220> FEATURE:
<223> OTHER INFORMATION: AT45 Light chain -continued

```
<400> SEQUENCE: 139

Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Thr Phe Gly Gly Gly Thr Lys Val Glu Ile Lys Arg
            100                 105                 110

Thr Val

<210> SEQ ID NO 140
<211> LENGTH: 110
<212> TYPE: PRT
<213> ORGANISM: Artificial
<220> FEATURE:
<223> OTHER INFORMATION: AT47 Light chain

<400> SEQUENCE: 140

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Ser Ile Ser Thr Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Ala Ile Ser Ser Leu Gln Pro
65                  70                  75                  80

Asp Asp Phe Ala Thr Tyr Tyr Cys Gln Gln Tyr Lys Ser Tyr Pro Tyr
                85                  90                  95

Thr Phe Gly Gln Gly Thr Lys Leu Glu Leu Lys Arg Thr Val
            100                 105                 110

<210> SEQ ID NO 141
<211> LENGTH: 114
<212> TYPE: PRT
<213> ORGANISM: Artificial
<220> FEATURE:
<223> OTHER INFORMATION: AT49 Light chain

<400> SEQUENCE: 141

Asp Ile Val Met Thr Gln Ser Pro Leu Ser Leu Thr Val Thr Pro Gly
1               5                   10                  15

Glu Pro Ala Ser Ile Ser Cys Arg Ser Ser Gln Ser Leu Leu His Gly
            20                  25                  30

Asn Gly Tyr Lys Tyr Leu His Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Ala Arg Phe Ser Gly Ser Gly Ser Asp Thr Asp Phe Thr Leu Lys Ile
```

```
                65                  70                  75                  80
Ser Thr Val Glu Thr Glu Asp Val Gly Val Tyr Tyr Cys Met Gln Ala
                    85                  90                  95

Leu Gln Ser Pro Thr Phe Gly Gln Gly Thr Lys Val Glu Ile Lys Arg
                100                 105                 110

Thr Val

<210> SEQ ID NO 142
<211> LENGTH: 110
<212> TYPE: PRT
<213> ORGANISM: Artificial
<220> FEATURE:
<223> OTHER INFORMATION: AT50 Light chain

<400> SEQUENCE: 142

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Val Ile Ser Ser Tyr
                20                  25                  30

Leu Ala Trp Tyr Gln Gln Thr Pro Gly Arg Ala Pro Lys Leu Leu Ile
            35                  40                  45

Tyr Gly Ala Ser Thr Leu Gln Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Leu Asn Thr Tyr Pro Leu
                85                  90                  95

Thr Phe Gly Pro Gly Thr Lys Val Glu Ile Lys Arg Thr Val
                100                 105                 110

<210> SEQ ID NO 143
<211> LENGTH: 110
<212> TYPE: PRT
<213> ORGANISM: Artificial
<220> FEATURE:
<223> OTHER INFORMATION: AT51 Light chain

<400> SEQUENCE: 143

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Thr Ser Tyr
                20                  25                  30

Leu Ala Trp Tyr Gln Gln Lys Pro Gly Arg Ala Pro Lys Leu Leu Ile
            35                  40                  45

Tyr Ala Ala Ser Thr Leu Gln Ser Gly Val Ala Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Phe His Thr Tyr Pro Leu
                85                  90                  95

Thr Phe Gly Gly Gly Thr Lys Val Glu Ile Lys Arg Thr Val
                100                 105                 110

<210> SEQ ID NO 144
<211> LENGTH: 108
<212> TYPE: PRT
<213> ORGANISM: Artificial
<220> FEATURE:
<223> OTHER INFORMATION: AM22 Light chain
```

<400> SEQUENCE: 144

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Val Ser Arg Asn
            20                  25                  30

His Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Val Arg Phe Ser
    50                  55                  60

Gly Ser Gly Ser Gly Thr Asp Phe Thr Leu Thr Ile Asn Gly Leu Ala
65                  70                  75                  80

Pro Glu Asp Phe Ala Val Tyr Tyr Cys Leu Ser Ser Asp Ser Ser Ile
                85                  90                  95

Phe Thr Phe Gly Pro Gly Thr Lys Val Asp Phe Lys
            100                 105

<210> SEQ ID NO 145
<211> LENGTH: 18
<212> TYPE: DNA
<213> ORGANISM: Artificial
<220> FEATURE:
<223> OTHER INFORMATION: AT46 Heavy chain CDR1

<400> SEQUENCE: 145
agtagatatg tcatgagt                                                 18

<210> SEQ ID NO 146
<211> LENGTH: 15
<212> TYPE: DNA
<213> ORGANISM: Artificial
<220> FEATURE:
<223> OTHER INFORMATION: AT32 Heavy chain CDR1

<400> SEQUENCE: 146
gaattatcca tacac                                                    15

<210> SEQ ID NO 147
<211> LENGTH: 15
<212> TYPE: PRT
<213> ORGANISM: Artificial
<220> FEATURE:
<223> OTHER INFORMATION: AT33 Heavy chain CDR1

<400> SEQUENCE: 147

Ala Gly Thr Cys Thr Thr Gly Cys Cys Ala Thr Cys Ala Gly Thr
1               5                   10                  15

<210> SEQ ID NO 148
<211> LENGTH: 15
<212> TYPE: DNA
<213> ORGANISM: Artificial
<220> FEATURE:
<223> OTHER INFORMATION: AT34 Heavy chain CDR1

<400> SEQUENCE: 148
cattatggca tgcac                                                    15

<210> SEQ ID NO 149
<211> LENGTH: 15
<212> TYPE: DNA
<213> ORGANISM: Artificial
<220> FEATURE:

<223> OTHER INFORMATION: AT35 Heavy chain CDR1

<400> SEQUENCE: 149
acctattggg tgagc                                                        15

<210> SEQ ID NO 150
<211> LENGTH: 27
<212> TYPE: DNA
<213> ORGANISM: Artificial
<220> FEATURE:
<223> OTHER INFORMATION: AT36 Heavy chain CDR1

<400> SEQUENCE: 150
tacaacttta tcgaccatag tgtcagc                                           27

<210> SEQ ID NO 151
<211> LENGTH: 21
<212> TYPE: PRT
<213> ORGANISM: Artificial
<220> FEATURE:
<223> OTHER INFORMATION: AT37 Heavy chain CDR1

<400> SEQUENCE: 151

Ala Gly Thr Gly Gly Thr Gly Gly Thr Thr Ala Cys Thr Cys Cys Thr
1               5                   10                  15
Gly Gly Ala Ala Cys
            20

<210> SEQ ID NO 152
<211> LENGTH: 15
<212> TYPE: DNA
<213> ORGANISM: Artificial
<220> FEATURE:
<223> OTHER INFORMATION: AT39 Heavy chain CDR1

<400> SEQUENCE: 152
acctatgctg tacat                                                        15

<210> SEQ ID NO 153
<211> LENGTH: 18
<212> TYPE: DNA
<213> ORGANISM: Artificial
<220> FEATURE:
<223> OTHER INFORMATION: AT40 Heavy chain CDR1

<400> SEQUENCE: 153
gatagacatg ctctccac                                                     18

<210> SEQ ID NO 154
<211> LENGTH: 21
<212> TYPE: DNA
<213> ORGANISM: Artificial
<220> FEATURE:
<223> OTHER INFORMATION: AT42 Heavy chain CDR1

<400> SEQUENCE: 154
agtaatgttt actactgggg c                                                 21

<210> SEQ ID NO 155
<211> LENGTH: 15
<212> TYPE: DNA
<213> ORGANISM: Artificial
<220> FEATURE:
<223> OTHER INFORMATION: AT43 Heavy chain CDR1

<400> SEQUENCE: 155

```
aactatggtg tcagc                                             15
```

<210> SEQ ID NO 156
<211> LENGTH: 18
<212> TYPE: DNA
<213> ORGANISM: Artificial
<220> FEATURE:
<223> OTHER INFORMATION: AT44 Heavy chain CDR1

<400> SEQUENCE: 156

```
agcggtcact actgggcc                                          18
```

<210> SEQ ID NO 157
<211> LENGTH: 15
<212> TYPE: DNA
<213> ORGANISM: Artificial
<220> FEATURE:
<223> OTHER INFORMATION: AT45 Heavy chain CDR1

<400> SEQUENCE: 157

```
ggccatgcta tcagc                                             15
```

<210> SEQ ID NO 158
<211> LENGTH: 15
<212> TYPE: DNA
<213> ORGANISM: Artificial
<220> FEATURE:
<223> OTHER INFORMATION: AT47 Heavy chain CDR1

<400> SEQUENCE: 158

```
aactacggta tctgt                                             15
```

<210> SEQ ID NO 159
<211> LENGTH: 15
<212> TYPE: DNA
<213> ORGANISM: Artificial
<220> FEATURE:
<223> OTHER INFORMATION: AT49 Heavy chain CDR1

<400> SEQUENCE: 159

```
agccttgctc tcaat                                             15
```

<210> SEQ ID NO 160
<211> LENGTH: 15
<212> TYPE: DNA
<213> ORGANISM: Artificial
<220> FEATURE:
<223> OTHER INFORMATION: AT50 Heavy chain CDR1

<400> SEQUENCE: 160

```
aactatggta tcagt                                             15
```

<210> SEQ ID NO 161
<211> LENGTH: 15
<212> TYPE: DNA
<213> ORGANISM: Artificial
<220> FEATURE:
<223> OTHER INFORMATION: AT51 Heavy chain CDR1

<400> SEQUENCE: 161

```
aagtatggca tcaac                                             15
```

<210> SEQ ID NO 162
<211> LENGTH: 15
<212> TYPE: DNA

```
<213> ORGANISM: Artificial
<220> FEATURE:
<223> OTHER INFORMATION: AM22 Heavy chain CDR1

<400> SEQUENCE: 162
aaattatcca ttcac                                                        15

<210> SEQ ID NO 163
<211> LENGTH: 66
<212> TYPE: DNA
<213> ORGANISM: Artificial
<220> FEATURE:
<223> OTHER INFORMATION: AT46 Heavy chain CDR2

<400> SEQUENCE: 163
agcattactg gaagtggtgc tacgacatac tatgcagact ccgtgaaggg ccgcttcacc        60
atctcc                                                                  66

<210> SEQ ID NO 164
<211> LENGTH: 51
<212> TYPE: DNA
<213> ORGANISM: Artificial
<220> FEATURE:
<223> OTHER INFORMATION: AT32 Heavy chain CDR2

<400> SEQUENCE: 164
ggttttgagc ctgaggatgg tgagtacatc tacccacaga atcccagggg c                 51

<210> SEQ ID NO 165
<211> LENGTH: 51
<212> TYPE: DNA
<213> ORGANISM: Artificial
<220> FEATURE:
<223> OTHER INFORMATION: AT33 Heavy chain CDR2

<400> SEQUENCE: 165
gggatcatcc ctaagttcaa tagaagagac tacgcacaga gtttcagggc                   51

<210> SEQ ID NO 166
<211> LENGTH: 51
<212> TYPE: DNA
<213> ORGANISM: Artificial
<220> FEATURE:
<223> OTHER INFORMATION: AT34 Heavy chain CDR2

<400> SEQUENCE: 166
gtcatatcct atgatggcga taaaaaatat tatgcagact cagtgaaggg c                 51

<210> SEQ ID NO 167
<211> LENGTH: 66
<212> TYPE: DNA
<213> ORGANISM: Artificial
<220> FEATURE:
<223> OTHER INFORMATION: AT35 Heavy chain CDR2

<400> SEQUENCE: 167
aacattaacc aagatggaag tgagaagtcc tatgtggact ctgtggaggg ccgattcacc        60
atctcc                                                                  66

<210> SEQ ID NO 168
<211> LENGTH: 51
<212> TYPE: DNA
<213> ORGANISM: Artificial
<220> FEATURE:
<223> OTHER INFORMATION: AT36 Heavy chain CDR2
```

<400> SEQUENCE: 168
tggatcagcc cttacaacca cagaacagta tatgcagaga agttccaggg c        51

<210> SEQ ID NO 169
<211> LENGTH: 48
<212> TYPE: DNA
<213> ORGANISM: Artificial
<220> FEATURE:
<223> OTHER INFORMATION: AT37 Heavy chain CDR2

<400> SEQUENCE: 169
tacatctatc agaatgacat cacctactac aacccgtccc tcatgagt        48

<210> SEQ ID NO 170
<211> LENGTH: 66
<212> TYPE: DNA
<213> ORGANISM: Artificial
<220> FEATURE:
<223> OTHER INFORMATION: AT39 Heavy chain CDR2

<400> SEQUENCE: 170
tggatcaacc ctgacaatgg tgacacaaaa tattcacaga ggttccaggg tagagtcgtc        60
attacc        66

<210> SEQ ID NO 171
<211> LENGTH: 51
<212> TYPE: DNA
<213> ORGANISM: Artificial
<220> FEATURE:
<223> OTHER INFORMATION: AT39 Heavy chain CDR2

<400> SEQUENCE: 171
attctctctt atgatgggac cacagactac tacgcagact ccgtgaaggg c        51

<210> SEQ ID NO 172
<211> LENGTH: 48
<212> TYPE: DNA
<213> ORGANISM: Artificial
<220> FEATURE:
<223> OTHER INFORMATION: AT40 Heavy chain CDR2

<400> SEQUENCE: 172
agtatctttc atagtgggat cacccactat accccgtccc tcaatagt        48

<210> SEQ ID NO 173
<211> LENGTH: 51
<212> TYPE: DNA
<213> ORGANISM: Artificial
<220> FEATURE:
<223> OTHER INFORMATION: AT43 Heavy chain CDR2

<400> SEQUENCE: 173
tggatcagca cttacaatgg taacacatgg tattcacaga agttccaggc c        51

<210> SEQ ID NO 174
<211> LENGTH: 48
<212> TYPE: DNA
<213> ORGANISM: Artificial
<220> FEATURE:
<223> OTHER INFORMATION: AT44 Heavy chain CDR2

<400> SEQUENCE: 174
ggtatccatc atagtgggag tacctacacc aatccgcccc tcaagagc        48

```
<210> SEQ ID NO 175
<211> LENGTH: 51
<212> TYPE: DNA
<213> ORGANISM: Artificial
<220> FEATURE:
<223> OTHER INFORMATION: AT45 Heavy chain CDR2

<400> SEQUENCE: 175
gggatcatcc ctggccttgg tacaacaagg tacgcacgga agttccagga c            51

<210> SEQ ID NO 176
<211> LENGTH: 51
<212> TYPE: DNA
<213> ORGANISM: Artificial
<220> FEATURE:
<223> OTHER INFORMATION: AT47 Heavy chain CDR2

<400> SEQUENCE: 176
tggatcagcg gttacaatgg taacacatac tatgcacaga acttccaggg c            51

<210> SEQ ID NO 177
<211> LENGTH: 51
<212> TYPE: DNA
<213> ORGANISM: Artificial
<220> FEATURE:
<223> OTHER INFORMATION: AT49 Heavy chain CDR2

<400> SEQUENCE: 177
gggatcatcc ctctctttgg cactcaaaac tacgcacaga agttccaggg c            51

<210> SEQ ID NO 178
<211> LENGTH: 51
<212> TYPE: DNA
<213> ORGANISM: Artificial
<220> FEATURE:
<223> OTHER INFORMATION: AT50 Heavy chain CDR2

<400> SEQUENCE: 178
tggatcagcg cttacaatgg taacacatac tatagacagg agctccaggg c            51

<210> SEQ ID NO 179
<211> LENGTH: 51
<212> TYPE: DNA
<213> ORGANISM: Artificial
<220> FEATURE:
<223> OTHER INFORMATION: AT51 Heavy chain CDR2

<400> SEQUENCE: 179
tggatcagcg catacaatgg caacacatac tatgcacaga agttccaggg c            51

<210> SEQ ID NO 180
<211> LENGTH: 51
<212> TYPE: DNA
<213> ORGANISM: Artificial
<220> FEATURE:
<223> OTHER INFORMATION: AM22 Heavy chain CDR2

<400> SEQUENCE: 180
ggttatgagg gtgaggtcga tgagattttc tacgcacaga agttccagca c            51

<210> SEQ ID NO 181
<211> LENGTH: 30
<212> TYPE: DNA
<213> ORGANISM: Artificial
<220> FEATURE:
<223> OTHER INFORMATION: AT46 Heavy chain CDR3
```

<400> SEQUENCE: 181
tgtggtaggg cgggccaaat ttttgacgac                                              30

<210> SEQ ID NO 182
<211> LENGTH: 48
<212> TYPE: DNA
<213> ORGANISM: Artificial
<220> FEATURE:
<223> OTHER INFORMATION: AT32 Heavy chain CDR3

<400> SEQUENCE: 182
gaggcaagat attgtgataa cagcagatgt tcccctaact ttgaccac                          48

<210> SEQ ID NO 183
<211> LENGTH: 42
<212> TYPE: DNA
<213> ORGANISM: Artificial
<220> FEATURE:
<223> OTHER INFORMATION: AT33 Heavy chain CDR3

<400> SEQUENCE: 183
gacgccgagt gggcagctgg ctcggattac ttctttgact ac                                42

<210> SEQ ID NO 184
<211> LENGTH: 51
<212> TYPE: DNA
<213> ORGANISM: Artificial
<220> FEATURE:
<223> OTHER INFORMATION: AT34 Heavy chain CDR3

<400> SEQUENCE: 184 caggggggcaa agggcggtca cgaactttct ttctactgtg ctttggacgt c                     51

<210> SEQ ID NO 185
<211> LENGTH: 42
<212> TYPE: DNA
<213> ORGANISM: Artificial
<220> FEATURE:
<223> OTHER INFORMATION: AT35 Heavy chain CDR3

<400> SEQUENCE: 185
gaagtcttcg tgactcaggt ggagcccgcg cagtggggct tc                                42

<210> SEQ ID NO 186
<211> LENGTH: 39
<212> TYPE: DNA
<213> ORGANISM: Artificial
<220> FEATURE:
<223> OTHER INFORMATION: AT36 Heavy chain CDR3

<400> SEQUENCE: 186
gatcgagtac aacagggcga gggaaacttc tttgaccac                                    39

<210> SEQ ID NO 187
<211> LENGTH: 48
<212> TYPE: DNA
<213> ORGANISM: Artificial
<220> FEATURE:
<223> OTHER INFORMATION: AT37 Heavy chain CDR3

<400> SEQUENCE: 187
ggggcctatg gttcgggaac ttattattcc gctgatgctc ttgatata                          48

<210> SEQ ID NO 188

```
<211> LENGTH: 18
<212> TYPE: DNA
<213> ORGANISM: Artificial
<220> FEATURE:
<223> OTHER INFORMATION: AT39 Heavy chain CDR3

<400> SEQUENCE: 188
gggagaattt ttgatata                                                   18

<210> SEQ ID NO 189
<211> LENGTH: 51
<212> TYPE: DNA
<213> ORGANISM: Artificial
<220> FEATURE:
<223> OTHER INFORMATION: AT40 Heavy chain CDR3

<400> SEQUENCE: 189
ggaagggccc tagatgactt cgctgactac gggggatact actttgacta c              51

<210> SEQ ID NO 190
<211> LENGTH: 27
<212> TYPE: DNA
<213> ORGANISM: Artificial
<220> FEATURE:
<223> OTHER INFORMATION: AT42 Heavy chain CDR3

<400> SEQUENCE: 190
cattgggctg gcctctactt tgactct                                         27

<210> SEQ ID NO 191
<211> LENGTH: 45
<212> TYPE: DNA
<213> ORGANISM: Artificial
<220> FEATURE:
<223> OTHER INFORMATION: AT43 Heavy chain CDR3

<400> SEQUENCE: 191
cacgggagtg gcaattacta cggcgaagcg aactactttg accac                     45

<210> SEQ ID NO 192
<211> LENGTH: 42
<212> TYPE: DNA
<213> ORGANISM: Artificial
<220> FEATURE:
<223> OTHER INFORMATION: AT44 Heavy chain CDR3

<400> SEQUENCE: 192
gatctgtacg atctttcgac ggggccttttt tggttcgacc cc                       42

<210> SEQ ID NO 193
<211> LENGTH: 36
<212> TYPE: DNA
<213> ORGANISM: Artificial
<220> FEATURE:
<223> OTHER INFORMATION: AT45 Heavy chain CDR3

<400> SEQUENCE: 193
gtggccgggg gatacttcga tagtgctact cgaggc                               36

<210> SEQ ID NO 194
<211> LENGTH: 42
<212> TYPE: DNA
<213> ORGANISM: Artificial
<220> FEATURE:
<223> OTHER INFORMATION: AT47 Heavy chain CDR3

<400> SEQUENCE: 194
```

```
gggtttcact atcatagtgc tgatcagaga atattcgacc cc                    42
```

<210> SEQ ID NO 195
<211> LENGTH: 45
<212> TYPE: DNA
<213> ORGANISM: Artificial
<220> FEATURE:
<223> OTHER INFORMATION: AT49 Heavy chain CDR3

<400> SEQUENCE: 195

```
tttctttggt tcggggacca aacgagtgat gatggttttg atgtc                 45
```

<210> SEQ ID NO 196
<211> LENGTH: 54
<212> TYPE: DNA
<213> ORGANISM: Artificial
<220> FEATURE:
<223> OTHER INFORMATION: AT50 Heavy chain CDR3

<400> SEQUENCE: 196

```
gggggtgccc aagagatggt tagaatacac tactactact acggaatgga cgtc       54
```

<210> SEQ ID NO 197
<211> LENGTH: 54
<212> TYPE: DNA
<213> ORGANISM: Artificial
<220> FEATURE:
<223> OTHER INFORMATION: AT51 Heavy chain CDR3

<400> SEQUENCE: 197

```
cccgcaacct catatgacga tcttcggagt ggttatttga actactgtga ctac       54
```

<210> SEQ ID NO 198
<211> LENGTH: 45
<212> TYPE: DNA
<213> ORGANISM: Artificial
<220> FEATURE:
<223> OTHER INFORMATION: AM22 Heavy chain CDR3

<400> SEQUENCE: 198

```
ctaggtgtga cagtgactga ggctggactg gggatcgatg actac                 45
```

<210> SEQ ID NO 199
<211> LENGTH: 36
<212> TYPE: DNA
<213> ORGANISM: Artificial
<220> FEATURE:
<223> OTHER INFORMATION: AT46 Light chain CDR1

<400> SEQUENCE: 199

```
actctgagca gtgggcacag gaactacgcc atcgca                           36
```

<210> SEQ ID NO 200
<211> LENGTH: 51
<212> TYPE: DNA
<213> ORGANISM: Artificial
<220> FEATURE:
<223> OTHER INFORMATION: AT32 Light chain CDR1

<400> SEQUENCE: 200

```
aagtccagcc agagtgtttt atacgactcc aacaataaga actacttagc t          51
```

<210> SEQ ID NO 201
<211> LENGTH: 33
<212> TYPE: DNA

<213> ORGANISM: Artificial
<220> FEATURE:
<223> OTHER INFORMATION: AT33 Light chain CDR1

<400> SEQUENCE: 201
tctgcagatg cattttcaga ccaatatgct tat                         33

<210> SEQ ID NO 202
<211> LENGTH: 33
<212> TYPE: DNA
<213> ORGANISM: Artificial
<220> FEATURE:
<223> OTHER INFORMATION: AT34 Light chain CDR1

<400> SEQUENCE: 202
cgggccagtc agggtattgg tagttggttg gcc                         33

<210> SEQ ID NO 203
<211> LENGTH: 33
<212> TYPE: DNA
<213> ORGANISM: Artificial
<220> FEATURE:
<223> OTHER INFORMATION: AT35 Light chain CDR1

<400> SEQUENCE: 203
cgggcaagtc agagcattga caactattta aat                         33

<210> SEQ ID NO 204
<211> LENGTH: 51
<212> TYPE: DNA
<213> ORGANISM: Artificial
<220> FEATURE:
<223> OTHER INFORMATION: AT36 Light chain CDR1

<400> SEQUENCE: 204
aagtccagcc agagtctttt acacagctcc aacaataaga tctacttagc t     51

<210> SEQ ID NO 205
<211> LENGTH: 36
<212> TYPE: DNA
<213> ORGANISM: Artificial
<220> FEATURE:
<223> OTHER INFORMATION: AT37 Light chain CDR1

<400> SEQUENCE: 205
agggccagtc agagtgttag cgccagcaac ttagcc                      36

<210> SEQ ID NO 206
<211> LENGTH: 33
<212> TYPE: DNA
<213> ORGANISM: Artificial
<220> FEATURE:
<223> OTHER INFORMATION: AT39 Light chain CDR1

<400> SEQUENCE: 206
caggcgagtc aggacattag caacttttta aat                         33

<210> SEQ ID NO 207
<211> LENGTH: 33
<212> TYPE: DNA
<213> ORGANISM: Artificial
<220> FEATURE:
<223> OTHER INFORMATION: AT40 Light chain CDR1

<400> SEQUENCE: 207
cgggcgagtc agggtattag tacctggtta gcc                         33

<210> SEQ ID NO 208
<211> LENGTH: 36
<212> TYPE: DNA
<213> ORGANISM: Artificial
<220> FEATURE:
<223> OTHER INFORMATION: AT42 Light chain CDR1

<400> SEQUENCE: 208
agggccagtc agactgtaag cagcagccac ttagcc                    36

<210> SEQ ID NO 209
<211> LENGTH: 36
<212> TYPE: DNA
<213> ORGANISM: Artificial
<220> FEATURE:
<223> OTHER INFORMATION: AT43 Light chain CDR1

<400> SEQUENCE: 209
agggccagtg agagtgttag ccgcaactac ttagcc                    36

<210> SEQ ID NO 210
<211> LENGTH: 33
<212> TYPE: DNA
<213> ORGANISM: Artificial
<220> FEATURE:
<223> OTHER INFORMATION: AT44 Light chain CDR1

<400> SEQUENCE: 210
agggccagtc agagtgtcag caccaaggta gtc                       33

<210> SEQ ID NO 211
<211> LENGTH: 48
<212> TYPE: DNA
<213> ORGANISM: Artificial
<220> FEATURE:
<223> OTHER INFORMATION: AT45 Light chain CDR1

<400> SEQUENCE: 211
aggtctagtc agagcctcct gcatagtaat ggatacaact atttggat       48

<210> SEQ ID NO 212
<211> LENGTH: 33
<212> TYPE: DNA
<213> ORGANISM: Artificial
<220> FEATURE:
<223> OTHER INFORMATION: AT47 Light chain CDR1

<400> SEQUENCE: 212
cgggccagtg agagtattag tacctggttg gcc                       33

<210> SEQ ID NO 213
<211> LENGTH: 48
<212> TYPE: DNA
<213> ORGANISM: Artificial
<220> FEATURE:
<223> OTHER INFORMATION: AT49 Light chain CDR1

<400> SEQUENCE: 213
aggtctagtc agagcctcct gcatggtaat ggatacaaat atctgcac       48

<210> SEQ ID NO 214
<211> LENGTH: 33
<212> TYPE: DNA
<213> ORGANISM: Artificial
<220> FEATURE:

```
<223> OTHER INFORMATION: AT50 Light chain CDR1

<400> SEQUENCE: 214
cgggcaagcc aggtcattag cagttattta gcc                                    33

<210> SEQ ID NO 215
<211> LENGTH: 33
<212> TYPE: DNA
<213> ORGANISM: Artificial
<220> FEATURE:
<223> OTHER INFORMATION: AT51 Light chain CDR1

<400> SEQUENCE: 215
cgggcaagtc agggcattac cagttattta gcc                                    33

<210> SEQ ID NO 216
<211> LENGTH: 36
<212> TYPE: DNA
<213> ORGANISM: Artificial
<220> FEATURE:
<223> OTHER INFORMATION: AM22 Light chain CDR1

<400> SEQUENCE: 216
agggccagtc agattgttag caggaaccac ttagcc                                 36

<210> SEQ ID NO 217
<211> LENGTH: 27
<212> TYPE: DNA
<213> ORGANISM: Artificial
<220> FEATURE:
<223> OTHER INFORMATION: AT46 Light chain CDR2

<400> SEQUENCE: 217
actaatggca gccactaccc gggggac                                           27

<210> SEQ ID NO 218
<211> LENGTH: 21
<212> TYPE: DNA
<213> ORGANISM: Artificial
<220> FEATURE:
<223> OTHER INFORMATION: AT32 Light chain CDR2

<400> SEQUENCE: 218
tgggcgtcta cccgggaatc c                                                 21

<210> SEQ ID NO 219
<211> LENGTH: 21
<212> TYPE: DNA
<213> ORGANISM: Artificial
<220> FEATURE:
<223> OTHER INFORMATION: AT33 Light chain CDR2

<400> SEQUENCE: 219
aaagacactg agaggccctc a                                                 21

<210> SEQ ID NO 220
<211> LENGTH: 21
<212> TYPE: DNA
<213> ORGANISM: Artificial
<220> FEATURE:
<223> OTHER INFORMATION: AT34 Light chain CDR2

<400> SEQUENCE: 220
aacgcgtctg gcttagaaag t                                                 21
```

```
<210> SEQ ID NO 221
<211> LENGTH: 21
<212> TYPE: DNA
<213> ORGANISM: Artificial
<220> FEATURE:
<223> OTHER INFORMATION: AT35 Light chain CDR2

<400> SEQUENCE: 221
cttgcgtcca ctttgcaaag t                                              21

<210> SEQ ID NO 222
<211> LENGTH: 21
<212> TYPE: DNA
<213> ORGANISM: Artificial
<220> FEATURE:
<223> OTHER INFORMATION: AT36 Light chain CDR2

<400> SEQUENCE: 222
tgggcatcta cccgggagtc c                                              21

<210> SEQ ID NO 223
<211> LENGTH: 21
<212> TYPE: DNA
<213> ORGANISM: Artificial
<220> FEATURE:
<223> OTHER INFORMATION: AT37 Light chain CDR2

<400> SEQUENCE: 223
ggtgcatcca ggacggccac t                                              21

<210> SEQ ID NO 224
<211> LENGTH: 21
<212> TYPE: DNA
<213> ORGANISM: Artificial
<220> FEATURE:
<223> OTHER INFORMATION: AT39 Light chain CDR2

<400> SEQUENCE: 224
gatgcgtcca aattgcaaac a                                              21

<210> SEQ ID NO 225
<211> LENGTH: 21
<212> TYPE: DNA
<213> ORGANISM: Artificial
<220> FEATURE:
<223> OTHER INFORMATION: AT40 Light chain CDR2

<400> SEQUENCE: 225
tctgcatcca gattgcagag t                                              21

<210> SEQ ID NO 226
<211> LENGTH: 21
<212> TYPE: DNA
<213> ORGANISM: Artificial
<220> FEATURE:
<223> OTHER INFORMATION: AT42 Light chain CDR2

<400> SEQUENCE: 226
ggttcatcta gcagggccac a                                              21

<210> SEQ ID NO 227
<211> LENGTH: 21
<212> TYPE: DNA
<213> ORGANISM: Artificial
<220> FEATURE:
<223> OTHER INFORMATION: AT43 Light chain CDR2
```

```
<400> SEQUENCE: 227
ggtgcatcca gcagggccat t                                              21

<210> SEQ ID NO 228
<211> LENGTH: 21
<212> TYPE: DNA
<213> ORGANISM: Artificial
<220> FEATURE:
<223> OTHER INFORMATION: AT44 Light chain CDR2

<400> SEQUENCE: 228
ggtgcatcca ccagggccac t                                              21

<210> SEQ ID NO 229
<211> LENGTH: 18
<212> TYPE: DNA
<213> ORGANISM: Artificial
<220> FEATURE:
<223> OTHER INFORMATION: AT45 Light chain CDR2

<400> SEQUENCE: 229
ggttctaatc gggcccc                                                   18

<210> SEQ ID NO 230
<211> LENGTH: 21
<212> TYPE: DNA
<213> ORGANISM: Artificial
<220> FEATURE:
<223> OTHER INFORMATION: AT47 Light chain CDR2

<400> SEQUENCE: 230
aaggcgtcta gtttagaaag t                                              21

<210> SEQ ID NO 231
<211> LENGTH: 21
<212> TYPE: DNA
<213> ORGANISM: Artificial
<220> FEATURE:
<223> OTHER INFORMATION: AT49 Light chain CDR2

<400> SEQUENCE: 231
ttgggttcta atcgggcctc c                                              21

<210> SEQ ID NO 232
<211> LENGTH: 21
<212> TYPE: DNA
<213> ORGANISM: Artificial
<220> FEATURE:
<223> OTHER INFORMATION: AT50 Light chain CDR2

<400> SEQUENCE: 232
ggtgcatcca cgttacaaac t                                              21

<210> SEQ ID NO 233
<211> LENGTH: 21
<212> TYPE: DNA
<213> ORGANISM: Artificial
<220> FEATURE:
<223> OTHER INFORMATION: AT51 Light chain CDR2

<400> SEQUENCE: 233
gctgcatcca ctttgcaaag t                                              21

<210> SEQ ID NO 234
<211> LENGTH: 21
```

```
<212> TYPE: DNA
<213> ORGANISM: Artificial
<220> FEATURE:
<223> OTHER INFORMATION: AM22 Light chain CDR2

<400> SEQUENCE: 234
ggtgcgtcca gtcgggccac t                                        21

<210> SEQ ID NO 235
<211> LENGTH: 21
<212> TYPE: DNA
<213> ORGANISM: Artificial
<220> FEATURE:
<223> OTHER INFORMATION: AT46 Light chain CDR3

<400> SEQUENCE: 235
cagacctggg gcgctggcat t                                        21

<210> SEQ ID NO 236
<211> LENGTH: 21
<212> TYPE: DNA
<213> ORGANISM: Artificial
<220> FEATURE:
<223> OTHER INFORMATION: AT32 Light chain CDR3

<400> SEQUENCE: 236
caacaatatt atgatcctct c                                        21

<210> SEQ ID NO 237
<211> LENGTH: 27
<212> TYPE: DNA
<213> ORGANISM: Artificial
<220> FEATURE:
<223> OTHER INFORMATION: AT33 Light chain CDR3

<400> SEQUENCE: 237
caatcaacag acaccagtgg tcctttA                                  27

<210> SEQ ID NO 238
<211> LENGTH: 21
<212> TYPE: DNA
<213> ORGANISM: Artificial
<220> FEATURE:
<223> OTHER INFORMATION: AT34 Light chain CDR3

<400> SEQUENCE: 238
caacaataca atagtcacac g                                        21

<210> SEQ ID NO 239
<211> LENGTH: 21
<212> TYPE: DNA
<213> ORGANISM: Artificial
<220> FEATURE:
<223> OTHER INFORMATION: AT35 Light chain CDR3

<400> SEQUENCE: 239
caacagagcc actcttcccc c                                        21

<210> SEQ ID NO 240
<211> LENGTH: 24
<212> TYPE: DNA
<213> ORGANISM: Artificial
<220> FEATURE:
<223> OTHER INFORMATION: AT36 Light chain CDR3

<400> SEQUENCE: 240
```
cagcaatatt atactactca tccc                                            24

<210> SEQ ID NO 241
<211> LENGTH: 21
<212> TYPE: DNA
<213> ORGANISM: Artificial
<220> FEATURE:
<223> OTHER INFORMATION: AT37 Light chain CDR3

<400> SEQUENCE: 241
caacagtatg gtagctcacc g                                               21

<210> SEQ ID NO 242
<211> LENGTH: 21
<212> TYPE: DNA
<213> ORGANISM: Artificial
<220> FEATURE:
<223> OTHER INFORMATION: AT39 Light chain CDR3

<400> SEQUENCE: 242
caaaagtttg ataatctcct t                                               21

<210> SEQ ID NO 243
<211> LENGTH: 21
<212> TYPE: DNA
<213> ORGANISM: Artificial
<220> FEATURE:
<223> OTHER INFORMATION: AT40 Light chain CDR3

<400> SEQUENCE: 243
caacaggcta acactttccc c                                               21

<210> SEQ ID NO 244
<211> LENGTH: 21
<212> TYPE: DNA
<213> ORGANISM: Artificial
<220> FEATURE:
<223> OTHER INFORMATION: AT42 Light chain CDR3

<400> SEQUENCE: 244
cagtactatg gtgactcacc c                                               21

<210> SEQ ID NO 245
<211> LENGTH: 24
<212> TYPE: DNA
<213> ORGANISM: Artificial
<220> FEATURE:
<223> OTHER INFORMATION: AT43 Light chain CDR3

<400> SEQUENCE: 245
tgtcagcagt atactatctt ccct                                            24

<210> SEQ ID NO 246
<211> LENGTH: 21
<212> TYPE: DNA
<213> ORGANISM: Artificial
<220> FEATURE:
<223> OTHER INFORMATION: AT44 Light chain CDR3

<400> SEQUENCE: 246
cagcagtata ataagtggcc c                                               21

<210> SEQ ID NO 247
<211> LENGTH: 21
<212> TYPE: DNA
<213> ORGANISM: Artificial

```
<220> FEATURE:
<223> OTHER INFORMATION: AT45 Light chain CDR3

<400> SEQUENCE: 247
atgcaagctc tacaaactcc t                                              21

<210> SEQ ID NO 248
<211> LENGTH: 21
<212> TYPE: DNA
<213> ORGANISM: Artificial
<220> FEATURE:
<223> OTHER INFORMATION: AT47 Light chain CDR3

<400> SEQUENCE: 248
caacagtata aaagttaccc g                                              21

<210> SEQ ID NO 249
<211> LENGTH: 21
<212> TYPE: DNA
<213> ORGANISM: Artificial
<220> FEATURE:
<223> OTHER INFORMATION: AT49 Light chain CDR3

<400> SEQUENCE: 249
atgcaagctc tacaaagtcc g                                              21

<210> SEQ ID NO 250
<211> LENGTH: 21
<212> TYPE: DNA
<213> ORGANISM: Artificial
<220> FEATURE:
<223> OTHER INFORMATION: AT50 Light chain CDR3

<400> SEQUENCE: 250
caacagctta atacttaccc c                                              21

<210> SEQ ID NO 251
<211> LENGTH: 21
<212> TYPE: DNA
<213> ORGANISM: Artificial
<220> FEATURE:
<223> OTHER INFORMATION: AT51 Light chain CDR3

<400> SEQUENCE: 251
caacagtttc atacttaccc g                                              21

<210> SEQ ID NO 252
<211> LENGTH: 21
<212> TYPE: DNA
<213> ORGANISM: Artificial
<220> FEATURE:
<223> OTHER INFORMATION: AM22 Light chain CDR3

<400> SEQUENCE: 252
ctgtcctctg attcctccat a                                              21

<210> SEQ ID NO 253
<211> LENGTH: 357
<212> TYPE: DNA
<213> ORGANISM: Artificial
<220> FEATURE:
<223> OTHER INFORMATION: AT46 Heavy chain

<400> SEQUENCE: 253
gaggtgcagc tggtggagtc tgggggaggc ttggtacagc ctggggggtc cctgcgactc    60
```

| | |
|---|---|
| tcctgtgcag cctctggatt cacctttagt agatatgtca tgagttgggt ccgccaggct | 120 |
| ccagggaggg gcctggagtg ggtctcaagc attactggaa gtggtgctac gacatactat | 180 |
| gcagactccg tgaagggccg cttcaccatc tccagagaca attccaagaa cacggtgtat | 240 |
| ctgcaaatga acaggctgag agccgaggac acggccatat attactgtgc gaattgtggt | 300 |
| agggcgggcc aaattttga cgactggggc cagggaaccc tggtcaccgt ctcctca | 357 |

```
<210> SEQ ID NO 254
<211> LENGTH: 374
<212> TYPE: DNA
<213> ORGANISM: Artificial
<220> FEATURE:
<223> OTHER INFORMATION: AT32 Heavy chain

<400> SEQUENCE: 254
```

| | |
|---|---|
| caggtccagc tggtacaatc tggggctgag atgaagaagc ctggggcctc agtgaaggtc | 60 |
| tcctgccagg ttgccggata caccctcact gaattatcca tacactgggt gcgacagact | 120 |
| cctggaaacg ggcttgagtg gatgggaggt tttgagcctg aggatggtga gtacatctac | 180 |
| ccacagaaat cccagggcag agtcaccatg accgaggaca catctacagg cacagcctac | 240 |
| atggaactga ggagcctgag atctgacgac acggccgtgt attactgtgc agccgaggca | 300 |
| agatattgtg ataacagcag atgttcccct aactttgaca ctggggccag ggaaccctgg | 360 |
| tcgccgtctc ctca | 374 |

```
<210> SEQ ID NO 255
<211> LENGTH: 369
<212> TYPE: DNA
<213> ORGANISM: Artificial
<220> FEATURE:
<223> OTHER INFORMATION: AT33 Heavy chain

<400> SEQUENCE: 255
```

| | |
|---|---|
| caggtgcagt tggtgcagtc tggggctgag gtgaagaagc ctgggtcctc ggtgaaggtc | 60 |
| tcctgcaagg cttctggaga ctccttcaac agtcttgcca tcagttgggt gcgacaggcc | 120 |
| cctggacaag gactcgagtg gatgggaggg atcatcccta gttcaatag aagagactac | 180 |
| gcacagaagt tcagggcag agtcacgatt accgcggacg actccgcgag cacagcctac | 240 |
| atagagttga gcagcctgac atctgacgac acagccctgt attactgtgc gagagacgcc | 300 |
| gagtgggcag ctggctcgga ttacttcttt gactactggg gccagggaac cctggtcatc | 360 |
| gtctcctca | 369 |

```
<210> SEQ ID NO 256
<211> LENGTH: 378
<212> TYPE: DNA
<213> ORGANISM: Artificial
<220> FEATURE:
<223> OTHER INFORMATION: AT34 Heavy chain

<400> SEQUENCE: 256
```

| | |
|---|---|
| caggtgcaat tgatggagtc tgggggaggc gtggtccagc ctgggaagtc cctgagactc | 60 |
| tcctgtgcag cctctggatt caccttcagt cattatggca tgcactgggt ccgccaggct | 120 |
| ccaggcaagg ggctggagtg ggtggcagtc atatcctatg atggcgataa aaatattat | 180 |
| gcagactcag tgaagggccg attcaccatc tccagagaca attccaagaa cacgctgcat | 240 |
| ctccacatga atagcctgag acatgaggac acggctgtct atttctgtgc ctcccagggg | 300 |
| gcaaagggcg gtcacgaact ttctttctac tgtgctttgg acgtctgggg ccaagggacc | 360 |

```
acggtcgccg tctcctca                                              378

<210> SEQ ID NO 257
<211> LENGTH: 369
<212> TYPE: DNA
<213> ORGANISM: Artificial
<220> FEATURE:
<223> OTHER INFORMATION: AT35 Heavy chain

<400> SEQUENCE: 257
gaggtgcagc tggtggagtc tgggggaggc ttggtccagc cggggggggtc cctgagactc     60 tcctgtgcag cctctggatt cacctttagt acctattggg tgagctgggt ccgccagact    120
ccagggaagg gactggagtg ggtggccaac attaaccaag atggaagtga aagtcctat     180 gtggactctg tggagggccg attcaccatc tccagagaca acgctaagaa ctcgctgtat    240
ctgcaaatga acagcctgag agccgacgac acggctgtat attattgtgc gagagaagtc    300
ttcgtgactc aggtggagcc cgcgcagtgg ggcttctggg gccagggaac cccggtcatc    360
gtctcctcc                                                            369

<210> SEQ ID NO 258
<211> LENGTH: 369
<212> TYPE: DNA
<213> ORGANISM: Artificial
<220> FEATURE:
<223> OTHER INFORMATION: AT36 Heavy chain

<400> SEQUENCE: 258
caggttcagg tggtgcagtc tggagccgag gtgaagaagc ctggggcctc agtcaaggtc     60
tcttgcaaga cttctggtta caactttatc gaccatagtg tcagctgggt gcgacaggcc    120
cccggccaag ggcttgagtg gatgggatgg atcagccctt acaaccacag aacagtatat    180
gcagagaagt tccagggcag agtcaccatg accacagaca catcgacgag acagtctcc     240 atggagttga ggaggctgac atctgacgac acggccgtct acttctgtgc gcgagatcga    300
gtacaacagg gcgagggaaa cttctttgac cactggggcc agggaacccc ggtcaccgtc    360
acctcagcc                                                            369

<210> SEQ ID NO 259
<211> LENGTH: 378
<212> TYPE: DNA
<213> ORGANISM: Artificial
<220> FEATURE:
<223> OTHER INFORMATION: AT37 Heavy chain

<400> SEQUENCE: 259
cagctgcagc tgcaggagtc cggctccaga ctggtgaagc cttcacagac cctgtccctc     60
acctgcggtg tctctggtgg ctccatcagc agtggtggtt actcctggaa ctggatccgg    120
cagccaccag ggaagggcct ggagtgggtt gggtacatct atcagaatga catcacctac    180
tacaacccgt ccctcatgag tcgagtcacc atatcagcag acacgtccaa gaaccagttc    240
tccctgaagt tgagctctgt gaccgccgcg gacacggccg tgtattactg tgcccgaggg    300
gcctatggtt cggaaactta ttattccgct gatgctcttg atatatgggg ccaagggaca    360
atggtcaccg tctcttca                                                  378

<210> SEQ ID NO 260
<211> LENGTH: 345
<212> TYPE: DNA
```

```
<213> ORGANISM: Artificial
<220> FEATURE:
<223> OTHER INFORMATION: AT39 Heavy chain

<400> SEQUENCE: 260
caggtccagc ttgtgcagtc tgggcctgag gtgaagaagc ctggggcctc agtgaggctt      60
tcctgtacgg cctctggaaa caccttccgt acctatgctg tacattgggt gcgccaggcc     120
tccggacaaa gacttgagtg gatgggatgg atcaaccctg acaatggtga cacaaaatat     180
tcacagaggt tccagggtag agtcgtcatt accagggaca catccgcgag ataatctac      240 ttggacctga gcagcctgac atctgaagac acggctgtgt ctattgtttt cagcgggaga     300
atttttgata tgggggcca aggacaacg atcaccgtct cttca                       345

<210> SEQ ID NO 261
<211> LENGTH: 378
<212> TYPE: DNA
<213> ORGANISM: Artificial
<220> FEATURE:
<223> OTHER INFORMATION: AT40 Heavy chain

<400> SEQUENCE: 261
caggtgcagc tggtggagtc cggggggaggc gtggtccagc ctgggatgtc ccacagactc      60
tcctgtgcag cctctacatt gatcttcgat agacatgctc tccactgggt ccgccaggct     120
ccaggcgcgg gcctggagtg ggtggcgatt ctctcttatg atgggaccac agactactac     180
gcagactccg tgaagggccg attcaccgtc tccagagaca cctccaagaa cacagtgttt     240
ctacaaatga acgcctgag acctcaagac acggctgttt attactgtgc gagaggaagg     300
gccctagatg acttcgctga ctacggggga tactactttg actactgggg ccagggaatc     360
ctggtcaccg tctcctca                                                    378

<210> SEQ ID NO 262
<211> LENGTH: 357
<212> TYPE: DNA
<213> ORGANISM: Artificial
<220> FEATURE:
<223> OTHER INFORMATION: AT42 Heavy chain

<400> SEQUENCE: 262
caggtgcagc tgcaggagtc cggcccagga ctggtgcagc cttcggagac cctgtccctc      60
acttgcactg tttctggtga ctccatcacc agtaatgttt actactgggg ctggatccgc     120
cagcccccag ggaagggct ggagtggatt gggagtatct ttcatagtgg gatcaccac       180 tatacccgt ccctcaatag tcgagtcacc atatccgtcg acacgtccaa gaaccagttc     240
tccctgagac tgagttctgc gaccgccgca gacacggctg tatattattg tgcgaggcat     300
tgggctggcc tctactttga ctcttgggc cagggagccc tggtcgccgt ctcctca        357

<210> SEQ ID NO 263
<211> LENGTH: 372
<212> TYPE: DNA
<213> ORGANISM: Artificial
<220> FEATURE:
<223> OTHER INFORMATION: AT43 Heavy chain

<400> SEQUENCE: 263
caggttcagg tggtgcagtc tggacctgag gtgaagaagc ctggggcctc agtgagggtc      60
tcctgcaagg cttctggtta caccttacc aactatggtg tcagctgggt gacacaggcc      120
cctggacaag ggcttgagtg gatgggatgg atcagcactt acaatggtaa cacatggtat     180
```

```
tcacagaagt tccaggccag agtcaccatg accacagaca cttccacgag cacagcctac      240
atggaggtga ggagcctgag atctgacgac acggccatat attactgtgc gtgccacggg      300
agtggcaatt actacggcga agcgaactac tttgaccact ggggccaggg aaccctggtc      360
accgtctcct cc                                                         372
```

```
<210> SEQ ID NO 264
<211> LENGTH: 369
<212> TYPE: DNA
<213> ORGANISM: Artificial
<220> FEATURE:
<223> OTHER INFORMATION: AT44 Heavy chain

<400> SEQUENCE: 264
caggtgcagc tgcaggcgtc gggcccagga ctggtgaagc cttcggagac cctgtccctc      60
acctgtaatg tctctggcta ctccgtcagt agcggtcact actgggcctg gtccggcag       120 tccccaggga aggggctgga gtggattggg ggtatccatc atagtgggag tacctacacc      180
aatccgcccc tcaagagccg agtctccata tcaatagaca cgtccaagaa ccagttctct      240
ttgaggttga cctctgtgac cgccgcagac acggccgtgt atttctgtgc gagagatctg      300
tacgatcttt cgacggggcc ttttggttc gaccctggg gccagggaac cctggtcacc      360
gtctcctca                                                            369
```

```
<210> SEQ ID NO 265
<211> LENGTH: 363
<212> TYPE: DNA
<213> ORGANISM: Artificial
<220> FEATURE:
<223> OTHER INFORMATION: AT45 Heavy chain

<400> SEQUENCE: 265
caggtgcacc tggtgcagtc tggggctgag gtgaagaagc ctgggtcctc ggtgaaggtc      60
tcctgcaagg cttctggagg caccttcaac ggccatgcta tcagctggat acgacaggcc      120
cctggacaag gacttgagtg gaagggaggg atcatccctg ccttggtac aacaaggtac      180 gcacggaagt tccaggacag agtcacgatt accgcggacg aatccacgag acagcctac      240 atggagctga gcagcctgag atctgaggac acggccgtct attactgtgc gagagtggcc      300
gggggatact tcgatagtgc tactcgaggc tggggccagg gaaccctggt caccgtctcc      360
tca                                                                  363
```

```
<210> SEQ ID NO 266
<211> LENGTH: 369
<212> TYPE: DNA
<213> ORGANISM: Artificial
<220> FEATURE:
<223> OTHER INFORMATION: AT47 Heavy chain

<400> SEQUENCE: 266
caggttcagc tggtgcagtc tggaggtgag gtgaagaagc ctggggcctc agtgaaggtc      60
tcctgtaagg cttctggtta caccttcacc aactacggta tctgttgggt gcgacaggcc      120
cctggacaag gcttgaatg gatgggatgg atcagcggtt acaatggtaa cacatactat      180
gcacagaact tccagggcag agtcaccatg accacagaca catccacgag cacagcctac      240
atggagctga ggagcctgag atctgacgac acggccgtat attactgtgc gagagggttt      300
cactatcata gtgctgatca gagaatattc gacccctggg gccagggaac cctggtcacc      360
``` gtctcctca                                                              369

<210> SEQ ID NO 267
<211> LENGTH: 372
<212> TYPE: DNA
<213> ORGANISM: Artificial
<220> FEATURE:
<223> OTHER INFORMATION: AT49 Heavy chain

<400> SEQUENCE: 267
caggtgcttc tggtgcagtc tggggctgag ataaagaagc ctgggtcctc ggtgaaaatc     60
tcctgcaagg cctctggagg gaccttcagc agccttgctc tcaattgggt gcgacaggcc    120
cctggacagg ggcttcagtg gatgggaggg atcatccctc tctttggcac tcaaaactac    180
gcacagaagt tccagggcag agtcaccatt accgcggacg aatccacgag cacagcctac    240
atggagctga gcggcctgcg acccgaggac acggccgtct attactgtgc cctatttctt    300
tggttcgggg accaaacgag tgatgatggt tttgatgtct ggggccaagg gacagtggtc    360
accgtgtctt ca                                                        372

<210> SEQ ID NO 268
<211> LENGTH: 381
<212> TYPE: DNA
<213> ORGANISM: Artificial
<220> FEATURE:
<223> OTHER INFORMATION: AT50 Heavy chain

<400> SEQUENCE: 268
caggttcagc tggtgcagtc tggaactgag gtgaagaagc ctggggcctc agtgaaggtc     60
tcctgcaagg cttctggtta cacctttagc aactatggta tcagttgggt gcgacaggcc    120
cctggacaag gcttgagtg gatgggatgg atcagcgctt acaatggtaa cacatactat    180
agacaggagc tccagggcag agtcaccatg accacagaca catccacgag cacagcctac    240
atggagctga ggagcctgag atctgacgac acggccgtgt attactgtgc gagagggggt    300
gcccaagaga tggttagaat acactactac tactacggaa tggacgtctg ggggccaaggg    360 accacggtca ccgtctcctc a                                              381

<210> SEQ ID NO 269
<211> LENGTH: 381
<212> TYPE: DNA
<213> ORGANISM: Artificial
<220> FEATURE:
<223> OTHER INFORMATION: AT51 Heavy chain

<400> SEQUENCE: 269
caggttcagc tggtgcagtc tggagctgag gtgaagaagc ctggggcctc aatgacggtc     60
tcctgcaagg cctctggtta cacctttttcc aagtatggca tcaactgggt gcgacaggcc    120
cctggacaag gcttgagtg gctgggttgg atcagcgcat acaatggcaa cacatactat    180
gcacagaagt tccagggcag agtcaccatg accacagaca cagccacgag cacagcctac    240
atggacgtga ggaacctgag atctgacgac acggccatgt attactgtgc gaggcccgca    300
acctcatatg acgatcttcg gagtggttat ttgaactact gtgactactg gggccaggga    360
accctggtca ccgtctcctc a                                              381

<210> SEQ ID NO 270
<211> LENGTH: 372
<212> TYPE: DNA
<213> ORGANISM: Artificial

```
<220> FEATURE:
<223> OTHER INFORMATION: AM22 Heavy chain

<400> SEQUENCE: 270
caggtccagc tggtacagtc tggggctgag gtgaagaagc ccggggccac agtgaaagtc      60
tcctgcaaga tttccggaca caccctcatt aaattatcca ttcactgggt gcgacaggct     120
cctggaaagg ggcttgagtg gatgggaggt tatgagggtg aggtcgatga gattttctac     180
gcacagaagt tccagcacag actcaccgtg atcgccgaca cagcgacaga cacagtctac     240
atggaactgg gcaggctcac ctctgacgac acggccgtct atttctgtgg aacactaggt     300
gtgacagtga ctgaggctgg actggggatc gatgactact ggggccaggg aaccctggtc     360
accgtctcct ca                                                         372

<210> SEQ ID NO 271
<211> LENGTH: 345
<212> TYPE: DNA
<213> ORGANISM: Artificial
<220> FEATURE:
<223> OTHER INFORMATION: AT46 Light chain

<400> SEQUENCE: 271
cagcctgtgc tgactcaatc gccctctgcc tctgcctccc tgggagcctc ggtcaagctc      60
acctgcactc tgagcagtgg gcacaggaac tacgccatcg catggcatca gcagcgacca     120
gagaagggcc ctcgttactt gatgaagatt tatactaatg cagccacta cccgggggac      180 gggaccctg atcgcttctc aggctccagc tctggggctg agcgctacct caccatctcc      240
agcctccaat ctgaggatga ggctgactat tactgtcaga cctggggcgc tggcatttgg     300
gttttcggcg agggaccaa gctgaccgtc ctaggtcagc ccaag                      345

<210> SEQ ID NO 272
<211> LENGTH: 348
<212> TYPE: DNA
<213> ORGANISM: Artificial
<220> FEATURE:
<223> OTHER INFORMATION: AT32 Light chain

<400> SEQUENCE: 272
gacatcgtga tgacccagtc tccagactcc ctggctgtgt ctctgggcga gagggccacc      60
ttcagctgca gtccagcca gagtgtttta tacgactcca acaataagaa ctacttagct     120
tggtaccagc agagaccagg acagcctcct aagttgctca tttactgggc gtctacccgg     180
gaatccgggg tccctgaccg attcagtggc agcgggtctg ggacagattt cactctcacc     240
atcagcagtc tgcagcctga agatgtggca gtttattact gtcaacaata ttatgatcct     300
ctcatcacct tcggccaagg gacacgactg gagattaaac gaactgtg                  348

<210> SEQ ID NO 273
<211> LENGTH: 330
<212> TYPE: DNA
<213> ORGANISM: Artificial
<220> FEATURE:
<223> OTHER INFORMATION: AT33 Light chain

<400> SEQUENCE: 273
tcctatgagc tgactcagcc accctcggtg tcagtgtccc caggacagac ggccaggatc      60
acctgctctg cagatgcatt ttcagaccaa tatgcttatt ggtaccagca gaagccaggc     120
caggcccctg tgttggtgat atataaagac actgagaggc cctcagggat ccctgagcga     180
```

```
atctctggct ccagctcagg acaacagcc acgttgagca tcagtggagt ccaggcagaa    240
gacgaggctg actattactg tcaatcaaca gacaccagtg gtcctttatt cggcggaggg    300
acgaagctga ccctcctagg tcagcccaag                                     330

<210> SEQ ID NO 274
<211> LENGTH: 330
<212> TYPE: DNA
<213> ORGANISM: Artificial
<220> FEATURE:
<223> OTHER INFORMATION: AT34 Light chain

<400> SEQUENCE: 274
gacatccaga tgacccagtc tccttccacc ctgtctgcat ctgtgggaga cagagtcacc     60
atcacttgtc gggccagtca gggtattggt agttggttgg cctggtatca gcagaaacca   120
gggaaagccc caaaactcct gatctataac gcgtctggct tagaaagtgg cgtcccatca   180
gggttcagcg gcagtggatc tgggacagag ttcactctca ccatcagcag cctgcagcct   240
gatgattctg cgacgtatta ctgccaacaa tacaatagtc acacgtggac attcggccaa   300
gggaccaagg tggaattcaa gcgaactgtg                                     330

<210> SEQ ID NO 275
<211> LENGTH: 330
<212> TYPE: DNA
<213> ORGANISM: Artificial
<220> FEATURE:
<223> OTHER INFORMATION: AT35 Light chain

<400> SEQUENCE: 275
gccatccaga tgacccagtc tccatcctcc ctgtctgcat ctgtaggaga cagagtcacc     60
atctcttgcc gggcaagtca gagcattgac aactatttaa attggtatca gcagaaaccg   120
gggaaagccc ctaaactcct gctctttctt gcgtccactt tgcaaagtgg tgtcccttca   180
aggttcactg gcagtggatc tgggacagat ttcactctca ccatcagcag tcttcaacct   240
gaagattttg cgacttacta ctgtcaacag agccactctt cccctacag ttttggccag    300 gggaccaagc ttgagatcaa acgaactgtg                                     330

<210> SEQ ID NO 276
<211> LENGTH: 348
<212> TYPE: DNA
<213> ORGANISM: Artificial
<220> FEATURE:
<223> OTHER INFORMATION: AT36 Light chain

<400> SEQUENCE: 276
gacatcgtga tgacccagtc tccagactct ctggctgtgt ctctgggcga gagggccacc     60
atcaactgca gtccagcca gagtctttta cacagctcca acaataagat ctacttagct   120
tggtaccagc agaaaccagg acagcctcct aagttactcc tttactgggc atctacccgg   180
gagtccgggg tccctgaccg cttcactggc agcgggtctg ggacagattt cactctcacc   240
atcaacagcc tgcaggctga ggatgtggct gtttattact gtcagcaata ttatactact   300
catcccactt ttggccaggg gaccaggctg gagatcaaac gaactgtg                 348

<210> SEQ ID NO 277
<211> LENGTH: 333
<212> TYPE: DNA
<213> ORGANISM: Artificial
<220> FEATURE:
<223> OTHER INFORMATION: AT37 Light chain
```

<400> SEQUENCE: 277

| aaaattgtgt tgacgcagtc tccaggcacc ctgtctttgt ctccagggga aagagccacc | 60 |
| ctctcctgca gggccagtca gagtgttagc gccagcaact tagcctggta ccagcagaaa | 120 |
| cctggccagg ctcccaggct cctcatctat ggtgcatcca ggacggccac tggcatccca | 180 |
| gacaggttca gtggcagtgg gtctgggaca gacttcactc tctccatcag cagactggag | 240 |
| cctgaagatt ttgcagtgta ttactgtcaa cagtatggta gctcaccgct cactttcggc | 300 |
| ggagggacca aggtggagat caaacgaact gtg | 333 |

<210> SEQ ID NO 278
<211> LENGTH: 330
<212> TYPE: DNA
<213> ORGANISM: Artificial
<220> FEATURE:
<223> OTHER INFORMATION: AT39 Light chain

<400> SEQUENCE: 278

| gacatccaga tgacccagtc tccatcctcc ctgtcagcat ctgtgggaga cagagtcacc | 60 |
| atcacttgcc aggcgagtca ggacattagc aacttttaa attggtatca gcagaaaccg | 120 |
| ggccaagccc ctaaactcct gatctatgat gcgtccaaat tgcaaacagg ggtcccgtca | 180 |
| aggttcagtg gaagtggttc tgagacagac tttactttca ccatcagcag cctgcagcct | 240 |
| gaagatgttg caacatatta ctgtcaaaag tttgataatc tccttctcac tttcggcgga | 300 |
| gggaccaagg tggagctcaa gcgaactgtg | 330 |

<210> SEQ ID NO 279
<211> LENGTH: 330
<212> TYPE: DNA
<213> ORGANISM: Artificial
<220> FEATURE:
<223> OTHER INFORMATION: AT40 Light chain

<400> SEQUENCE: 279

| gacatccaga tgacccagtc tccatcttcc gtatctgcgt ctgtgggaga caaagtcacc | 60 |
| atcacctgtc gggcgagtca gggtattagt acctggttag cctggtatca gcagaaacct | 120 |
| gggaaagctc ctgccctcct gatatattct gcatccagat tgcagagtgg ggtcccctca | 180 |
| aggtttagcg gcagtggatc tgggacagat ttcactctca ccatcagcag cctgcagcct | 240 |
| gaagattatg caacctatta ttgtcaacag gctaacactt tccccttcac tttcggccct | 300 |
| gggaccaaag tggacatcaa acgaactgtg | 330 |

<210> SEQ ID NO 280
<211> LENGTH: 333
<212> TYPE: DNA
<213> ORGANISM: Artificial
<220> FEATURE:
<223> OTHER INFORMATION: AT42 Light chain

<400> SEQUENCE: 280

| gaaatcgtgt tgacgcagtc tccaggcacc ctgtctctgt ctccagggga aagagccacc | 60 |
| ctctcctgca gggccagtca gactgtaagc agcagccact tagcctggta ccagcagaaa | 120 |
| cctggccagg ctcccaggct cctcatccat ggttcatcta gcagggccac aggcatccca | 180 |
| gagaggttca gtggcagtgg gtctgggcca gacttcactc tcaccatctc cagactgaag | 240 |
| cctgaagatt ttgctgtgta ttactgtcag tactatggtg actcacccgg ctctttcggc | 300 |

```
gaagggacca aggtggagat caaacgaact gtg                                333
```

```
<210> SEQ ID NO 281
<211> LENGTH: 333
<212> TYPE: DNA
<213> ORGANISM: Artificial
<220> FEATURE:
<223> OTHER INFORMATION: AT43 Light chain

<400> SEQUENCE: 281
gacattgtgt tgacgcagtc tccaggcacc ctgtctttgt ctccagggga aggagccacc      60
ctctcctgca gggccagtga gagtgttagc cgcaactact tagcctggta ccagcaaaaa     120
cctggccagg ctcccaggct cctcatctat ggtgcatcca gcagggccat ggcatccca     180 gacaggttca gtggcagtgg gtctgggaca gacttcactc tcaccatcag cagactggag     240
cctgaagatt ttgcagtata ctgctgtcag cagtatacta tcttccctct cactttcggc    300
ggagggacca aggtggagat caaacgaact gtg                                  333
```

```
<210> SEQ ID NO 282
<211> LENGTH: 333
<212> TYPE: DNA
<213> ORGANISM: Artificial
<220> FEATURE:
<223> OTHER INFORMATION: AT44 Light chain

<400> SEQUENCE: 282
gaaatcgtga tgacgcagtc accagccacc ctgtctgtgt ctccaggga gagagtcacc       60 ctctcctgta gggccagtca gagtgtcagc accaaggtag tctggtacca gcagaaattt    120
ggccaggctc ccaggctcct catctatggt gcatccacca gggccactgg tatcccagtc     180
aggttcagtg gcagtgggtc tgggacagag ttcactctca ccatcagcag cctgcagtct    240
gaagatcttg cagtttattt ctgtcagcag tataataagt ggcccatgta cacttttggc    300
caggggacca gttggaaat caaacgaact gtg                                   333
```

```
<210> SEQ ID NO 283
<211> LENGTH: 342
<212> TYPE: DNA
<213> ORGANISM: Artificial
<220> FEATURE:
<223> OTHER INFORMATION: AT45 Light chain

<400> SEQUENCE: 283
gatattgtga tgactcagtc tccactctcc ctgcccgtca cccctggaga gtcggcctcc      60
atctcctgca ggtctagtca gagcctcctg catagtaatg gatacaacta tttggattgg    120
tacctgcaga agccagggca gtctccacag ctcctgatct atttgggttc taatcgggcc     180
cccggggtcc ctgacaggtt tagtggcagt ggatcaggca cagatttac actgaaaatc     240 agcagagtgg aggctgagga tgttggggtt tattactgca tgcaagctct acaaactcct    300
acgttcggcc aagggaccaa ggtggaaatc aaacgaactg tg                        342
```

```
<210> SEQ ID NO 284
<211> LENGTH: 330
<212> TYPE: DNA
<213> ORGANISM: Artificial
<220> FEATURE:
<223> OTHER INFORMATION: AT47 Light chain

<400> SEQUENCE: 284
gacatccaga tgacccagtc tccttccacc ctgtctgcat ctgtaggaga cagagtcacc      60
```

```
atcacttgcc gggccagtga gagtattagt acctggttgg cctggtatca gcagaaacca    120
gggaaagccc ctaacctcct gatctataag gcgtctagtt tagaaagtgg ggtcccatca    180
aggttcagcg gcagtggatc tgggacagaa ttcactctcg ccatcagcag cctgcagcct    240
gatgattttg caacttatta ctgccaacag tataaaagtt acccgtacac ttttggccag    300
gggaccaagc tggagctgaa acgaactgtg                                     330
```

<210> SEQ ID NO 285
<211> LENGTH: 342
<212> TYPE: DNA
<213> ORGANISM: Artificial
<220> FEATURE:
<223> OTHER INFORMATION: AT49 Light chain

<400> SEQUENCE: 285

```
gatattgtga tgactcagtc accgctctcc ctgaccgtca ccccgggaga gccggcctcc    60
atctcatgca ggtctagtca gagcctcctg catggtaatg gatacaaata tctgcactgg    120
tacctgcaga agccagggca gtctccacag ctcctgatct atttgggttc taatcgggcc    180
tccggggtcc ctgccaggtt cagtggcagt ggatcagaca cagattttac tctgaaaatc    240
agcaccgtgg agactgagga tgttggggtt tattactgca tgcaagctct acaaagtccg    300
acgttcggcc aagggactaa ggtggaaatc aaacgaactg tg                       342
```

<210> SEQ ID NO 286
<211> LENGTH: 330
<212> TYPE: DNA
<213> ORGANISM: Artificial
<220> FEATURE:
<223> OTHER INFORMATION: AT50 Light chain

<400> SEQUENCE: 286

```
gacatccagt tgacccagtc tccatccttc ctgtctgcat ctgtaggaga cagagtcacc    60
atcacttgcc gggcaagcca ggtcattagc agttatttag cctggtatca gcaaacacca    120
gggagagccc ctaagctcct gatctatggt gcatccacgt tacaaactgg ggtcccatca    180
aggttcagcg gcagtggatc tgggacagaa ttcactctca caatcagcag cctgcagcct    240
gaagatttcg caacttattt ctgtcaacag cttaatactt accccctcac tttcggccct    300
gggaccaaag tggagatcaa acgaactgtg                                     330
```

<210> SEQ ID NO 287
<211> LENGTH: 330
<212> TYPE: DNA
<213> ORGANISM: Artificial
<220> FEATURE:
<223> OTHER INFORMATION: AT51 Light chain

<400> SEQUENCE: 287

```
gacatccagt tgacccagtc tccatccttc ctgtctgcat ctgtaggaga cagagtcacc    60
atcacttgcc gggcaagtca ggcattacc agttatttag cctggtatca gcaaaaacca    120
gggagagccc ctaagctcct gatctatgct gcatccactt tgcaaagtgg ggtcgcatca    180
aggttcagcg gcagtggatc tgggacagaa ttcactctca caatcagcag cctgcagcct    240
gaagattttg caacttatta ctgtcaacag tttcatactt acccgctcac tttcggcgga    300
gggaccaagg tggagatcaa acgaactgtg                                     330
```

<210> SEQ ID NO 288

<211> LENGTH: 324
<212> TYPE: DNA
<213> ORGANISM: Artificial
<220> FEATURE:
<223> OTHER INFORMATION: AM22 Light chain

<400> SEQUENCE: 288

```
gaaattgtgt tgacacagtc tccaggcacc ctgtctttgt ctccaggaga aagagccacc      60
ctctcctgca gggccagtca gattgttagc aggaaccact tagcctggta ccagcaaaaa     120
cctggccagg ctcccaggct cctcatcttt ggtgcgtcca gtcgggccac tggcatccca     180
gtccggttca gtggcagtgg gtctgggaca gacttcactc tcaccatcaa cggactggcg     240
cctgaagatt ttgcagttta ctactgtctg tcctctgatt cctccatatt cacattcggc     300
cctgggacca aggtggattt caaa                                            324
```

<210> SEQ ID NO 289
<211> LENGTH: 298
<212> TYPE: PRT
<213> ORGANISM: respiratory syncytial virus

<400> SEQUENCE: 289

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Met
            35                  40                  45

Ile Ile Ser Thr Ser Leu Ile Ile Ala Ala Ile Ile Phe Ile Ala Ser
        50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Gly Asn Pro
                245                 250                 255

Glu Leu Thr Ser Gln Met Glu Thr Phe His Ser Thr Ser Ser Glu Gly
            260                 265                 270

```
Asn Pro Ser Pro Ser Gln Val Ser Thr Thr Ser Glu Tyr Pro Ser Gln
            275                 280                 285

Pro Ser Ser Pro Pro Asn Thr Pro Arg Gln
    290                 295

<210> SEQ ID NO 290
<211> LENGTH: 298
<212> TYPE: PRT
<213> ORGANISM: respiratory syncytial virus

<400> SEQUENCE: 290

Met Ser Lys Asn Lys Asp Gln Arg Thr Ala Lys Thr Leu Glu Lys Thr
1               5                   10                  15

Trp Asp Thr Leu Asn His Leu Leu Phe Ile Ser Ser Gly Leu Tyr Lys
            20                  25                  30

Leu Asn Leu Lys Ser Ile Ala Gln Ile Thr Leu Ser Ile Leu Ala Met
        35                  40                  45

Ile Ile Ser Thr Ser Leu Ile Ile Thr Ala Ile Ile Phe Ile Ala Ser
    50                  55                  60

Ala Asn His Lys Val Thr Leu Thr Thr Ala Ile Ile Gln Asp Ala Thr
65                  70                  75                  80

Ser Gln Ile Lys Asn Thr Thr Pro Thr Tyr Leu Thr Gln Asp Pro Gln
                85                  90                  95

Leu Gly Ile Ser Phe Ser Asn Leu Ser Glu Ile Thr Ser Gln Thr Thr
            100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Phe
        195                 200                 205

Lys Thr Thr Lys Lys Asp His Lys Pro Gln Thr Thr Lys Pro Lys Glu
210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
            260                 265                 270

Asn Leu Ser Pro Ser Gln Val Ser Thr Thr Ser Glu His Pro Ser Gln
        275                 280                 285

Pro Ser Ser Pro Pro Asn Thr Thr Arg Gln
290                 295

<210> SEQ ID NO 291
<211> LENGTH: 299
<212> TYPE: PRT
<213> ORGANISM: respiratory syncytial virus

<400> SEQUENCE: 291
```

-continued

```
Met Ser Lys His Lys Asn Gln Arg Thr Ala Arg Thr Leu Glu Lys Thr
1               5                   10                  15

Trp Asp Thr Leu Asn His Leu Ile Val Ile Ser Ser Cys Leu Tyr Arg
            20                  25                  30

Leu Asn Leu Lys Ser Ile Ala Gln Ile Ala Leu Ser Val Leu Ala Met
        35                  40                  45

Ile Ile Ser Thr Ser Leu Ile Ile Ala Ala Ile Ile Phe Ile Ile Ser
    50                  55                  60

Ala Asn His Lys Val Thr Leu Thr Thr Val Thr Val Gln Thr Ile Lys
65                  70                  75                  80

Asn His Thr Glu Lys Asn Ile Thr Thr Tyr Leu Thr Gln Val Pro Pro
                85                  90                  95

Glu Arg Val Ser Ser Ser Lys Gln Pro Thr Thr Thr Ser Pro Ile His
            100                 105                 110

Thr Asn Ser Ala Thr Thr Ser Pro Asn Thr Lys Ser Glu Thr His His
        115                 120                 125

Thr Thr Ala Gln Thr Lys Gly Arg Thr Thr Thr Ser Thr Gln Thr Asn
    130                 135                 140

Lys Pro Ser Thr Lys Pro Arg Leu Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
        195                 200                 205

Lys Thr Thr Asn Lys Arg Asp Pro Lys Thr Pro Ala Lys Thr Thr Lys
    210                 215                 220

Lys Glu Thr Thr Thr Asn Pro Thr Lys Lys Pro Thr Leu Thr Thr Thr
225                 230                 235                 240

Glu Arg Asp Thr Ser Thr Ser Gln Ser Thr Val Leu Asp Thr Thr Thr
                245                 250                 255

Leu Glu His Thr Ile Gln Gln Gln Ser Leu His Ser Thr Thr Pro Glu
            260                 265                 270

Asn Thr Pro Asn Ser Thr Gln Thr Pro Thr Ala Ser Glu Pro Ser Thr
        275                 280                 285

Ser Asn Ser Thr Gln Asn Thr Gln Ser His Ala
    290                 295

<210> SEQ ID NO 292
<211> LENGTH: 283
<212> TYPE: PRT
<213> ORGANISM: respiratory syncytial virus

<400> SEQUENCE: 292

Trp Asp Thr Leu Asn His Leu Ile Val Ile Ser Ser Cys Leu Tyr Lys
1               5                   10                  15

Leu Asn Leu Lys Ser Ile Ala Gln Ile Ala Leu Ser Ile Leu Ala Met
            20                  25                  30

Ile Ile Ser Thr Ser Leu Ile Ile Ala Ala Ile Val Phe Ile Ile Ser
        35                  40                  45

Ala Asn His Lys Val Thr Pro Thr Thr Val Thr Val Gln Thr Ile Lys
    50                  55                  60

Asn His Thr Glu Lys Asn Ile Thr Thr Tyr Leu Thr His Val Ser Pro
65                  70                  75                  80
```

```
Asp Arg Val Ser Pro Ser Lys Gln Pro Thr Thr Pro Pro Ile His
                85                  90                  95

Thr Asn Ser Thr Thr Ile Ser Pro Asn Thr Lys Ser Glu Lys His His
            100                 105                 110

Thr Thr Ala Gln Thr Lys Gly Arg Thr Thr Thr Ser Thr Gln Thr Asn
        115                 120                 125

Lys Pro Ser Thr Lys Pro Arg Pro Lys Asn Pro Pro Lys Lys Pro Lys
    130                 135                 140

Asp Asp Tyr His Phe Glu Val Phe Asn Phe Val Pro Cys Ser Ile Cys
145                 150                 155                 160

Gly Asn Asn Gln Leu Cys Lys Ser Ile Cys Lys Thr Ile Pro Ser Asn
                165                 170                 175

Lys Pro Lys Lys Lys Pro Thr Ile Lys Pro Thr Asn Lys Pro Thr Thr
            180                 185                 190

Lys Thr Thr Asn Lys Lys Asp Pro Lys Thr Pro Ala Lys Thr Leu Lys
        195                 200                 205

Lys Glu Thr Thr Thr Asn Pro Thr Lys Lys Leu Thr Leu Lys Thr Thr
    210                 215                 220

Glu Arg Asp Thr Ser Thr Leu Gln Ser Thr Val Leu Asp Thr Thr Thr
225                 230                 235                 240

Ser Lys His Thr Thr Leu Gln Gln Ser Leu His Ser Thr Thr Pro Glu
                245                 250                 255

Asn Thr Pro Asn Phe Thr Gln Thr Pro Thr Ala Ser Glu Pro Ser Thr
            260                 265                 270

Ser Asn Ser Thr Gln Glu Ala Gln Ser Tyr Ala
        275                 280

<210> SEQ ID NO 293
<211> LENGTH: 284
<212> TYPE: PRT
<213> ORGANISM: respiratory syncytial virus

<400> SEQUENCE: 293

Thr Leu Glu Lys Thr Trp Asp Thr Leu Asn His Leu Ile Val Ile Ser
1               5                   10                  15

Ser Cys Leu Tyr Arg Leu Asn Leu Lys Ser Ile Ala Gln Ile Ala Leu
            20                  25                  30

Ser Val Leu Ala Met Ile Ile Ser Thr Ser Leu Ile Ile Ala Ala Ile
        35                  40                  45

Ile Phe Ile Ile Ser Ala Asn His Lys Val Thr Leu Thr Thr Val Thr
    50                  55                  60

Val Gln Thr Ile Lys Asn His Thr Glu Lys Asn Ile Thr Thr Tyr Leu
65                  70                  75                  80

Thr Gln Val Ser Pro Glu Arg Val Ser Pro Ser Lys Gln Pro Thr Thr
                85                  90                  95

Thr Pro Pro Ile His Thr Asn Ser Ala Thr Ile Ser Pro Asn Thr Lys
            100                 105                 110

Ser Glu Thr His His Thr Thr Ala Gln Thr Lys Gly Arg Thr Thr Thr
        115                 120                 125

Pro Thr Gln Asn Asn Lys Pro Ser Thr Lys Pro Arg Pro Lys Asn Pro
    130                 135                 140

Pro Lys Lys Pro Lys Asp Asp Tyr His Phe Glu Val Phe Asn Phe Val
145                 150                 155                 160

Pro Cys Ser Ile Cys Gly Asn Asn Gln Leu Cys Lys Ser Ile Cys Lys
```

```
                165                 170                 175

Thr Ile Pro Ser Asn Lys Pro Lys Lys Pro Thr Ile Lys Pro Thr
            180                 185                 190

Asn Lys Pro Pro Thr Lys Thr Thr Asn Lys Arg Asp Pro Lys Thr Leu
        195                 200                 205

Ala Lys Ile Leu Glu Lys Glu Thr Thr Thr Asn Pro Thr Lys Lys Pro
    210                 215                 220

Thr Pro Lys Thr Thr Glu Arg Asp Thr Ser Thr Ser Gln Ser Thr Val
225                 230                 235                 240

Leu Asp Thr Thr Thr Ser Lys His Thr Ile Gln Gln Gln Ser Leu His
                245                 250                 255

Ser Thr Thr Pro Glu Asn Thr Pro Asn Ser Thr Gln Thr Pro Thr Ala
            260                 265                 270

Ser Glu Pro Ser Thr Ser Asn Ser Thr Gln Lys Leu
        275                 280
```

<210> SEQ ID NO 294
<211> LENGTH: 15
<212> TYPE: PRT
<213> ORGANISM: Artificial
<220> FEATURE:
<223> OTHER INFORMATION: RSV Ga sequence

<400> SEQUENCE: 294

```
Asn Asp Phe His Phe Glu Val Phe Asn Phe Val Pro Cys Ser Ile
1               5                   10                  15
```

<210> SEQ ID NO 295
<211> LENGTH: 13
<212> TYPE: PRT
<213> ORGANISM: Artificial
<220> FEATURE:
<223> OTHER INFORMATION: RSV Ga sequence

<400> SEQUENCE: 295

```
Cys Lys Arg Ile Pro Asn Lys Lys Pro Gly Lys Lys Thr
1               5                   10
```

<210> SEQ ID NO 296
<211> LENGTH: 6
<212> TYPE: PRT
<213> ORGANISM: Artificial
<220> FEATURE:
<223> OTHER INFORMATION: RSV epitope

<400> SEQUENCE: 296

```
Phe Glu Val Phe Asn Phe
1               5
```

<210> SEQ ID NO 297
<211> LENGTH: 5
<212> TYPE: PRT
<213> ORGANISM: Artificial
<220> FEATURE:
<223> OTHER INFORMATION: RSV CX3C binding domain

<400> SEQUENCE: 297

```
Cys Trp Ala Ile Cys
1               5
```

<210> SEQ ID NO 298
<211> LENGTH: 5
<212> TYPE: PRT

<213> ORGANISM: Artificial
<220> FEATURE:
<223> OTHER INFORMATION: RSV epitope

<400> SEQUENCE: 298

Glu Val Phe Asn Phe
1               5

<210> SEQ ID NO 299
<211> LENGTH: 6
<212> TYPE: PRT
<213> ORGANISM: Artificial
<220> FEATURE:
<223> OTHER INFORMATION: sortase recognition site

<400> SEQUENCE: 299

Leu Pro Glu Thr Gly Gly
1               5

<210> SEQ ID NO 300
<211> LENGTH: 5
<212> TYPE: PRT
<213> ORGANISM: Artificial
<220> FEATURE:
<223> OTHER INFORMATION: sequence for RSV antibody

<400> SEQUENCE: 300

Gly Gly Gly Gly Ser
1               5

<210> SEQ ID NO 301
<211> LENGTH: 9
<212> TYPE: PRT
<213> ORGANISM: Artificial
<220> FEATURE:
<223> OTHER INFORMATION: RSV epitope

<400> SEQUENCE: 301

His Phe Glu Val Phe Asn Phe Val Pro
1               5

<210> SEQ ID NO 302
<211> LENGTH: 5
<212> TYPE: PRT
<213> ORGANISM: Artificial
<220> FEATURE:
<223> OTHER INFORMATION: RSV epitope

<400> SEQUENCE: 302

His Phe Glu Val Phe
1               5

<210> SEQ ID NO 303
<211> LENGTH: 9
<212> TYPE: PRT
<213> ORGANISM: Artificial
<220> FEATURE:
<223> OTHER INFORMATION: RSV epitope

<400> SEQUENCE: 303

Phe His Phe Glu Val Phe Asn Phe Val
1               5

<210> SEQ ID NO 304
<211> LENGTH: 9
<212> TYPE: PRT
<213> ORGANISM: Artificial

-continued

```
<220> FEATURE:
<223> OTHER INFORMATION: RSV epitope

<400> SEQUENCE: 304

His Phe Glu Val Phe Asn Phe Val Pro
1               5

<210> SEQ ID NO 305
<211> LENGTH: 12
<212> TYPE: PRT
<213> ORGANISM: Artificial
<220> FEATURE:
<223> OTHER INFORMATION: RSV epitope

<400> SEQUENCE: 305

Lys Gln Arg Gln Asn Lys Pro Pro Ser Lys Pro Asn
1               5                   10

<210> SEQ ID NO 306
<211> LENGTH: 12
<212> TYPE: PRT
<213> ORGANISM: Artificial
<220> FEATURE:
<223> OTHER INFORMATION: RSV epitope

<400> SEQUENCE: 306

Gln Arg Gln Asn Lys Pro Pro Ser Lys Pro Asn Asn
1               5                   10

<210> SEQ ID NO 307
<211> LENGTH: 12
<212> TYPE: PRT
<213> ORGANISM: Artificial
<220> FEATURE:
<223> OTHER INFORMATION: RSV epitope

<400> SEQUENCE: 307

Arg Gln Asn Lys Pro Pro Ser Lys Pro Asn Asn Asp
1               5                   10

<210> SEQ ID NO 308
<211> LENGTH: 12
<212> TYPE: PRT
<213> ORGANISM: Artificial
<220> FEATURE:
<223> OTHER INFORMATION: RSV epitope

<400> SEQUENCE: 308

Gln Asn Lys Pro Pro Ser Lys Pro Asn Asn Asp Phe
1               5                   10

<210> SEQ ID NO 309
<211> LENGTH: 12
<212> TYPE: PRT
<213> ORGANISM: Artificial
<220> FEATURE:
<223> OTHER INFORMATION: RSV epitope

<400> SEQUENCE: 309

Asn Lys Pro Pro Ser Lys Pro Asn Asn Asp Phe His
1               5                   10

<210> SEQ ID NO 310
<211> LENGTH: 12
<212> TYPE: PRT
<213> ORGANISM: Artificial
<220> FEATURE:
```

<223> OTHER INFORMATION: RSV epitope

<400> SEQUENCE: 310

Lys Pro Pro Ser Lys Pro Asn Asn Asp Phe His Phe
1               5                   10

<210> SEQ ID NO 311
<211> LENGTH: 12
<212> TYPE: PRT
<213> ORGANISM: Artificial
<220> FEATURE:
<223> OTHER INFORMATION: RSV epitope

<400> SEQUENCE: 311

Pro Pro Ser Lys Pro Asn Asn Asp Phe His Phe Glu
1               5                   10

<210> SEQ ID NO 312
<211> LENGTH: 12
<212> TYPE: PRT
<213> ORGANISM: Artificial
<220> FEATURE:
<223> OTHER INFORMATION: RSV epitope

<400> SEQUENCE: 312

Pro Ser Lys Pro Asn Asn Asp Phe His Phe Glu Val
1               5                   10

<210> SEQ ID NO 313
<211> LENGTH: 12
<212> TYPE: PRT
<213> ORGANISM: Artificial
<220> FEATURE:
<223> OTHER INFORMATION: RSV epitope

<400> SEQUENCE: 313

Ser Lys Pro Asn Asn Asp Phe His Phe Glu Val Phe
1               5                   10

<210> SEQ ID NO 314
<211> LENGTH: 12
<212> TYPE: PRT
<213> ORGANISM: Artificial
<220> FEATURE:
<223> OTHER INFORMATION: RSV epitope

<400> SEQUENCE: 314

Lys Pro Asn Asn Asp Phe His Phe Glu Val Phe Asn
1               5                   10

<210> SEQ ID NO 315
<211> LENGTH: 12
<212> TYPE: PRT
<213> ORGANISM: Artificial
<220> FEATURE:
<223> OTHER INFORMATION: RSV epitope

<400> SEQUENCE: 315

Pro Asn Asn Asp Phe His Phe Glu Val Phe Asn Phe
1               5                   10

<210> SEQ ID NO 316
<211> LENGTH: 12
<212> TYPE: PRT
<213> ORGANISM: Artificial
<220> FEATURE:
<223> OTHER INFORMATION: RSV epitope

```
<400> SEQUENCE: 316

Asn Asn Asp Phe His Phe Glu Val Phe Asn Phe Val
 1               5                  10

<210> SEQ ID NO 317
<211> LENGTH: 12
<212> TYPE: PRT
<213> ORGANISM: Artificial
<220> FEATURE:
<223> OTHER INFORMATION: RSV epitope

<400> SEQUENCE: 317

Asn Asp Phe His Phe Glu Val Phe Asn Phe Val Pro
 1               5                  10

<210> SEQ ID NO 318
<211> LENGTH: 12
<212> TYPE: PRT
<213> ORGANISM: Artificial
<220> FEATURE:
<223> OTHER INFORMATION: RSV epitope

<400> SEQUENCE: 318

Asp Phe His Phe Glu Val Phe Asn Phe Val Pro Cys
 1               5                  10

<210> SEQ ID NO 319
<211> LENGTH: 12
<212> TYPE: PRT
<213> ORGANISM: Artificial
<220> FEATURE:
<223> OTHER INFORMATION: RSV epitope

<400> SEQUENCE: 319

Phe His Phe Glu Val Phe Asn Phe Val Pro Cys Ser
 1               5                  10

<210> SEQ ID NO 320
<211> LENGTH: 12
<212> TYPE: PRT
<213> ORGANISM: Artificial
<220> FEATURE:
<223> OTHER INFORMATION: RSV epitope

<400> SEQUENCE: 320

His Phe Glu Val Phe Asn Phe Val Pro Cys Ser Ile
 1               5                  10

<210> SEQ ID NO 321
<211> LENGTH: 12
<212> TYPE: PRT
<213> ORGANISM: Artificial
<220> FEATURE:
<223> OTHER INFORMATION: RSV epitope

<400> SEQUENCE: 321

Phe Glu Val Phe Asn Phe Val Pro Cys Ser Ile Cys
 1               5                  10

<210> SEQ ID NO 322
<211> LENGTH: 12
<212> TYPE: PRT
<213> ORGANISM: Artificial
<220> FEATURE:
<223> OTHER INFORMATION: RSV epitope
```

<400> SEQUENCE: 322

Glu Val Phe Asn Phe Val Pro Cys Ser Ile Cys Ser
1               5                   10

<210> SEQ ID NO 323
<211> LENGTH: 12
<212> TYPE: PRT
<213> ORGANISM: Artificial
<220> FEATURE:
<223> OTHER INFORMATION: RSV epitope

<400> SEQUENCE: 323

Val Phe Asn Phe Val Pro Cys Ser Ile Cys Ser Asn
1               5                   10

<210> SEQ ID NO 324
<211> LENGTH: 12
<212> TYPE: PRT
<213> ORGANISM: Artificial
<220> FEATURE:
<223> OTHER INFORMATION: RSV epitope

<400> SEQUENCE: 324

Phe Asn Phe Val Pro Cys Ser Ile Cys Ser Asn Asn
1               5                   10

<210> SEQ ID NO 325
<211> LENGTH: 12
<212> TYPE: PRT
<213> ORGANISM: Artificial
<220> FEATURE:
<223> OTHER INFORMATION: RSV epitope

<400> SEQUENCE: 325

Asn Phe Val Pro Cys Ser Ile Cys Ser Asn Asn Pro
1               5                   10

<210> SEQ ID NO 326
<211> LENGTH: 12
<212> TYPE: PRT
<213> ORGANISM: Artificial
<220> FEATURE:
<223> OTHER INFORMATION: RSV epitope

<400> SEQUENCE: 326

Phe Val Pro Cys Ser Ile Cys Ser Asn Asn Pro Thr
1               5                   10

<210> SEQ ID NO 327
<211> LENGTH: 12
<212> TYPE: PRT
<213> ORGANISM: Artificial
<220> FEATURE:
<223> OTHER INFORMATION: RSV epitope

<400> SEQUENCE: 327

Val Pro Cys Ser Ile Cys Ser Asn Asn Pro Thr Cys
1               5                   10

<210> SEQ ID NO 328
<211> LENGTH: 12
<212> TYPE: PRT
<213> ORGANISM: Artificial
<220> FEATURE:
<223> OTHER INFORMATION: RSV epitope

<400> SEQUENCE: 328

```
Pro Cys Ser Ile Cys Ser Asn Asn Pro Thr Cys Trp
1               5                   10
```

<210> SEQ ID NO 329
<211> LENGTH: 12
<212> TYPE: PRT
<213> ORGANISM: Artificial
<220> FEATURE:
<223> OTHER INFORMATION: RSV epitope

<400> SEQUENCE: 329

```
Cys Ser Ile Cys Ser Asn Asn Pro Thr Cys Trp Ala
1               5                   10
```

<210> SEQ ID NO 330
<211> LENGTH: 12
<212> TYPE: PRT
<213> ORGANISM: Artificial
<220> FEATURE:
<223> OTHER INFORMATION: RSV epitope

<400> SEQUENCE: 330

```
Ser Ile Cys Ser Asn Asn Pro Thr Cys Trp Ala Ile
1               5                   10
```

<210> SEQ ID NO 331
<211> LENGTH: 12
<212> TYPE: PRT
<213> ORGANISM: Artificial
<220> FEATURE:
<223> OTHER INFORMATION: RSV epitope

<400> SEQUENCE: 331

```
Ile Cys Ser Asn Asn Pro Thr Cys Trp Ala Ile Cys
1               5                   10
```

<210> SEQ ID NO 332
<211> LENGTH: 12
<212> TYPE: PRT
<213> ORGANISM: Artificial
<220> FEATURE:
<223> OTHER INFORMATION: RSV epitope

<400> SEQUENCE: 332

```
Cys Ser Asn Asn Pro Thr Cys Trp Ala Ile Cys Lys
1               5                   10
```

<210> SEQ ID NO 333
<211> LENGTH: 12
<212> TYPE: PRT
<213> ORGANISM: Artificial
<220> FEATURE:
<223> OTHER INFORMATION: RSV epitope

<400> SEQUENCE: 333

```
Ser Asn Asn Pro Thr Cys Trp Ala Ile Cys Lys Arg
1               5                   10
```

<210> SEQ ID NO 334
<211> LENGTH: 12
<212> TYPE: PRT
<213> ORGANISM: Artificial
<220> FEATURE:
<223> OTHER INFORMATION: RSV epitope

<400> SEQUENCE: 334

Asn Asn Pro Thr Cys Trp Ala Ile Cys Lys Arg Ile
1               5                   10

<210> SEQ ID NO 335
<211> LENGTH: 12
<212> TYPE: PRT
<213> ORGANISM: Artificial
<220> FEATURE:
<223> OTHER INFORMATION: RSV epitope

<400> SEQUENCE: 335

Asn Pro Thr Cys Trp Ala Ile Cys Lys Arg Ile Pro
1               5                   10

<210> SEQ ID NO 336
<211> LENGTH: 12
<212> TYPE: PRT
<213> ORGANISM: Artificial
<220> FEATURE:
<223> OTHER INFORMATION: RSV epitope

<400> SEQUENCE: 336

Pro Thr Cys Trp Ala Ile Cys Lys Arg Ile Pro Asn
1               5                   10

<210> SEQ ID NO 337
<211> LENGTH: 12
<212> TYPE: PRT
<213> ORGANISM: Artificial
<220> FEATURE:
<223> OTHER INFORMATION: RSV epitope

<400> SEQUENCE: 337

Thr Cys Trp Ala Ile Cys Lys Arg Ile Pro Asn Lys
1               5                   10

<210> SEQ ID NO 338
<211> LENGTH: 12
<212> TYPE: PRT
<213> ORGANISM: Artificial
<220> FEATURE:
<223> OTHER INFORMATION: RSV epitope

<400> SEQUENCE: 338

Cys Trp Ala Ile Cys Lys Arg Ile Pro Asn Lys Lys
1               5                   10

<210> SEQ ID NO 339
<211> LENGTH: 12
<212> TYPE: PRT
<213> ORGANISM: Artificial
<220> FEATURE:
<223> OTHER INFORMATION: RSV epitope

<400> SEQUENCE: 339

Trp Ala Ile Cys Lys Arg Ile Pro Asn Lys Lys Pro
1               5                   10

<210> SEQ ID NO 340
<211> LENGTH: 12
<212> TYPE: PRT

```
<213> ORGANISM: Artificial
<220> FEATURE:
<223> OTHER INFORMATION: RSV epitope

<400> SEQUENCE: 340

Ala Ile Cys Lys Arg Ile Pro Asn Lys Lys Pro Gly
1               5                   10

<210> SEQ ID NO 341
<211> LENGTH: 12
<212> TYPE: PRT
<213> ORGANISM: Artificial
<220> FEATURE:
<223> OTHER INFORMATION: RSV epitope

<400> SEQUENCE: 341

Ile Cys Lys Arg Ile Pro Asn Lys Lys Pro Gly Lys
1               5                   10

<210> SEQ ID NO 342
<211> LENGTH: 12
<212> TYPE: PRT
<213> ORGANISM: Artificial
<220> FEATURE:
<223> OTHER INFORMATION: RSV epitope

<400> SEQUENCE: 342

Cys Lys Arg Ile Pro Asn Lys Lys Pro Gly Lys Lys
1               5                   10

<210> SEQ ID NO 343
<211> LENGTH: 12
<212> TYPE: PRT
<213> ORGANISM: Artificial
<220> FEATURE:
<223> OTHER INFORMATION: RSV epitope

<400> SEQUENCE: 343

Lys Arg Ile Pro Asn Lys Lys Pro Gly Lys Lys Thr
1               5                   10

<210> SEQ ID NO 344
<211> LENGTH: 12
<212> TYPE: PRT
<213> ORGANISM: Artificial
<220> FEATURE:
<223> OTHER INFORMATION: RSV epitope

<400> SEQUENCE: 344

Arg Ile Pro Asn Lys Lys Pro Gly Lys Lys Thr Thr
1               5                   10

<210> SEQ ID NO 345
<211> LENGTH: 5
<212> TYPE: PRT
<213> ORGANISM: Artificial Sequence
<220> FEATURE:
<223> OTHER INFORMATION: RSV epitope

<400> SEQUENCE: 345

Arg Ile Pro Asn Lys
1               5

<210> SEQ ID NO 346
<211> LENGTH: 8
<212> TYPE: PRT
<213> ORGANISM: Artificial Sequence
```

```
<220> FEATURE:
<223> OTHER INFORMATION: RSV epitope

<400> SEQUENCE: 346

Phe His Phe Glu Val Phe Asn Phe
1               5
```